US008771688B2

(12) United States Patent
Morimoto et al.

(10) Patent No.: US 8,771,688 B2
(45) Date of Patent: Jul. 8, 2014

(54) METHOD OF TREATING MALIGNANT MESOTHELIOMA

(75) Inventors: Chikao Morimoto, Tokyo (JP); Kei Ohnuma, Tokyo (JP); Teruo Inamoto, Tokyo (JP)

(73) Assignee: The University of Tokyo, Tokyo (JP)

(*) Notice: Subject to any disclaimer, the term of this patent is extended or adjusted under 35 U.S.C. 154(b) by 225 days.

(21) Appl. No.: 13/385,206

(22) Filed: Feb. 7, 2012

(65) Prior Publication Data

US 2014/0004103 A1 Jan. 2, 2014

Related U.S. Application Data

(62) Division of application No. 12/450,223, filed as application No. PCT/JP2008/055344 on Mar. 14, 2008, now abandoned.

(60) Provisional application No. 60/894,786, filed on Mar. 14, 2007.

(51) Int. Cl.
*A61K 39/395* (2006.01)

(52) U.S. Cl.
USPC .................................... 424/133.1; 424/138.1

(58) Field of Classification Search
None
See application file for complete search history.

(56) References Cited

U.S. PATENT DOCUMENTS

| | | | |
|---|---|---|---|
| 7,198,788 | B2 | 4/2007 | Dang et al. |
| 7,462,698 | B2 | 12/2008 | Aoyagi et al. |
| 7,658,923 | B2 | 2/2010 | Dang et al. |
| 2003/0031665 | A1 | 2/2003 | Dang et al. |
| 2003/0138429 | A1 | 7/2003 | Pizzo et al. |
| 2007/0207143 | A1 | 9/2007 | Dang et al. |

FOREIGN PATENT DOCUMENTS

| | | | |
|---|---|---|---|
| JP | 2004533449 | A | 11/2004 |
| WO | 02/092127 | A1 | 11/2002 |
| WO | 2007/014169 | A2 | 2/2007 |

OTHER PUBLICATIONS

Berghmans et al., "Activity of Chemotherapy and Immunotherapy on Malignant Mesothelioma: A Systemic Review of the Literature With Meta-Analysis", Lung Cancer 2002; 38:111-121.
Carbone et al., "The Expression of CD26 and CD40 Ligand is Mutually Exclusive in Human T-Cell Non-Hodgkin's Lymphomas/Leukemias", Blood 1995; 86:4617-4626.
Kajiyama et al., "Dipeptidyl Peptidase IV Overexpression Induces Up-Regulation of E-Cadherin and Tissue Inhibitors of Matrix Metalloproteinases, Resulting in Decreased Invasive Potential in Ovarian Carcinoma Cells", Cancer Res. 2003; 63:2278-83.
Kobayashi et al., Association of CD26 With CD45RA Outside Lipid Rafts Attenuates Cord Blood T-cell Activation. Blood 2004; 103:1002-10.
Levenberg et al., "p27 is Involved in N-cadherin-mediated Contact Inhibition of Cell Growth and S-phase Entry", Oncogene 1999; 18:869-76.
Morimoto et al., "1F7, A Novel Cell Surface Molecule, Involved in Helper Function of CD4 Cells", J Immunol 1989; 143:3430-9.
Prang et al., "Cellular and Complement-dependent Cytotoxicity of Ep-CAM-specific Monoclonal Antibody MT201 Against Breast Cancer Cell Lines", Br J Cancer 2005; 92:342-9.
Rusch, "Pemetrexed and Cisplatin for Malignant Pleural Mesothelioma: A New Standard of Care?", J Clin Onco 2003, 21:2629-2630.
Sato et al., "CD26/Dipeptidyl Peptidase IV Enhances Expression of Topoisomerase II Alpha and Sensitivity to Apoptosis Induced by Topoisomerase N Inhibitors", Br J Cancer 2003; 89:1366-74.
Shultz et al., "Multiple Defects in Innate and Adaptive Immunologic Function in NOD/LtSz-scid Mice", J Immunol 1995; 154:180-91.
Suzuki et al., "Reentry Into the Cell Cycle of Contact-inhibited Vascular Endothelial Cells by a Phosphatase Inhibitor, Possible Involvement of Extracellular Signal-regulated Kinase and Phosphatidylinositol 3-kinase", J Biol Chem 2000; 275:3637-44.
Tanaka et al., "Construction of Epstein-Barr Virus-Based Expression Vector Containing Mini-OriP", Biochem Biophys Res Commun 1999; 264:938-43.
Vogelzang et al. "Phase III Study of Pemetrexed in Combination With Cisplatin Versus Cisplatin Alone in Patients With Malignant Pleural Mesothelioma", J Clin Onco 2003; 21:2636-2644.
Wesley et al., "Role for Dipeptidyl Peptidase IV in Tumor Suppression of Human Non Small Cell Lung Carcinoma Cells", Int J Cancer 2004; 109:855-66.
Wesley et al., "Dipeptidyl Peptidase Inhibits Malignant Phenotype of Prostate Cancer Cells by Blocking Basic Fibroblast Growth Factor Signaling Pathway", Cancer Res. 2005; 65:1325-1334.
Dang et al., T-large Granular Lymphocyte Lymphoproliferative Disorder: Expression of CD26 as a Marker of Clinically Aggressive Disease and Characterization of Marrow Inhibition, Br. J. Haematology 2003; 121:857-865.
Britton M, "The epidemiology of mesothelioma. Semin Surg Oncol", 2002; 29: 18-25.
Connelly et al., "Demographic patterns for mesothelioma in the United States" J. Natl Cancer Inst. 1987; 78: 1053-1060.
Cheng et al., "A novel consensus motif in fibronectin mediates dipeptidyl peptidase IV adhesion and metastasis", J Biol Chem 2003; 278: 24600-24607.
Dang et al., "Human CD4 Helper T Cell Activation: Functional Involvement of Two Distinct Collagen Receptors, 1F7 and VLA Integrin Family", J. Exp. Med., V.172, 649-652, 1990.
Inamoto et al., "Humanized Anti-CD26 Monoclonal Antibody as a Treatment for Malignant Mesothelioma Tumors", Clin Cancer Res 2007, 13(14) 4191-4200; Jul. 15, 2007.

(Continued)

*Primary Examiner* — Sheela J Huff
(74) *Attorney, Agent, or Firm* — McDermott Will & Emery LLP

(57) ABSTRACT

The present invention relates to a therapeutic agent for malignant mesothelioma comprising a substance which inhibits binding of CD26 to extracellular matrix such as an siRNA targeting CD26 cDNA or an anti-CD26 antibody. The present invention also relates to a method of treating malignant mesothelioma, which comprises administering the substance to a patient in need thereof.

12 Claims, 8 Drawing Sheets
(2 of 8 Drawing Sheet(s) Filed in Color)

(56) References Cited

OTHER PUBLICATIONS

Inamoto et al., "Anti-CD26 Monoclonal Antibody-Mediated G1-S Arrest of Human Renal Clear Cell Carcinoma Caki-2 is Associated with Retinoblastoma Substrate Dphosphorylation, Cyclin-Dependent Kinase 2 Reduction, p27kip1 Enhancement, and Disruption of Binding to the Extracellular Matrix", Clin Cancer Res 2006; 12(11), 3470-3477, Jun. 1, 2006.

Ishii et al., "CD26-mediated signaling for Tcell activation occurs in lipid rafts through its association with CD45RO", PNAS 2001; 98: 12138-12143.

Ho et al., "In vitro and in vivo antitumor effect of the anti-CD26 monoclonal antibody 1F7 on human CD30+ anaplastic large cell T-cell lymphoma Karpas 299", Clinical Cancer Research 2001; 7: 2031-2040.

Ismail-Khan et al., "Malignant Pleural Mesothelioma: A comprehensive review." Cancer Control 2006; vol. 13 No. 4, 255-263.

Iwata S, Morimoto C., "CD26/dipeptidyl peptidase IV in context. The different roles of a multifunctional ectoenzyme in malignant transformation", J Exp Med 1999; 190: 301-305.

Johnson et al., "Lung endothelial dipeptidyl peptidase IV is an adhesion molecule for lung-metastatic rat breast and prostate carcinoma cells", J Cell Bioi 1993; 121: 1423-1432.

Kajiyama et al., "Expression of dipeptidyl peptidase IV (DPPIV/CD26) in human mesothelial cells", p. 161-166, 2001.

Kajiyama et al, "Increased expression of dipeptidyl peptidase IV in human mesothelial cells by malignant ascites from ovarian carcinoma patients," Oncology, 2002, Vo1.63, No. 2, 158-165.

Kajiyama et al., "Prolonged survival and decreased invasive activity attributable to dipeptidyl peptidase IV overexpression in ovarian carcinoma", Cancer Res 2002; 62: 2753-2757.

Kehlen et al., "Biological significance of aminopeptidase N/CD13 in thyroid carcinomas", Cancer Res 2003; 63: 8500-8506.

Morimoto C, Schlossman SF, "The structure and function of CD26 in the T-cell immune response", Immunol Rev 1998; 161: 55-70.

John Nemunaitis et al., Phase I Trial of PT-100 (PT-100), A Cytokine-Inducing Small Molecule, Following Chemotherapy for Solid Tumor Malignancy, Cancer Investigation, 24: 553-561, 2006.

Ohnuma et al. "CD26 up-regulates expression of CD86 on antigen-presenting cells by means of caveolin-1", PNAS 2004; 101: 14186-14191.

Ohnuma et al., "G1/S cell cycle arrest provoked in human T cells by antibody to CD26", Immunology 2002; 107: 325-333.

Pass H., "Malignant pleural mesothelioma, surgical roles and novel therapies" Clinical Lung Cancer Nov. 2001; 3: 102-117.

Pro B, Dang NH., "CD26/dipeptidyl peptidase IV and its role in cancer", Histol Histopathol (2004); 19: 1345-1351.

Usami et al., "Establishment and characterization of four malignant pleural mesothelioma cell lines from Japanese patients", Cancer Sci 2006; 97: 387-394.

Yamochi T et al., "Regulation of p38 phosphorylation and topoisomerase IIa expression in the B-cell lymphoma line Jiyoye by CD26/dipeptidyl peptidase IV is associated with enhanced in vitro and in vivo sensitivity to doxorubicin", Cancer Res 2005; 65: 1973-1983.

U. Aytac, et al., CD26/Dipeptidyl Peptidase IV: A Regulator of Immune Function and a Potential Molecular Target for Therapy, Current Drug Targets—Immune, Endocrine and Metabolic Disorders, Bentham Science Publishers, vol. 4, No. 1, Mar. 1, 2004, pp. 11-18.

F. Kikkawa, et al., Increased Adhesion Potency of Ovarian Carcinoma Cells to Mesothelial Cells by Overexpression of Dipeptidyl Peptidase IV, International Journal of Cancer, vol. 105, No. 6, Jul. 20, 2003, pp. 779-783.

O.J. Cordero, et al., Preoperative serum CD26 levels: diagnostic efficiency and predictive value for colorectal cancer, vol. 83, No. 9, Nov. 1, 2000, pp. 1139-1146.

A

Fig. 1B - D
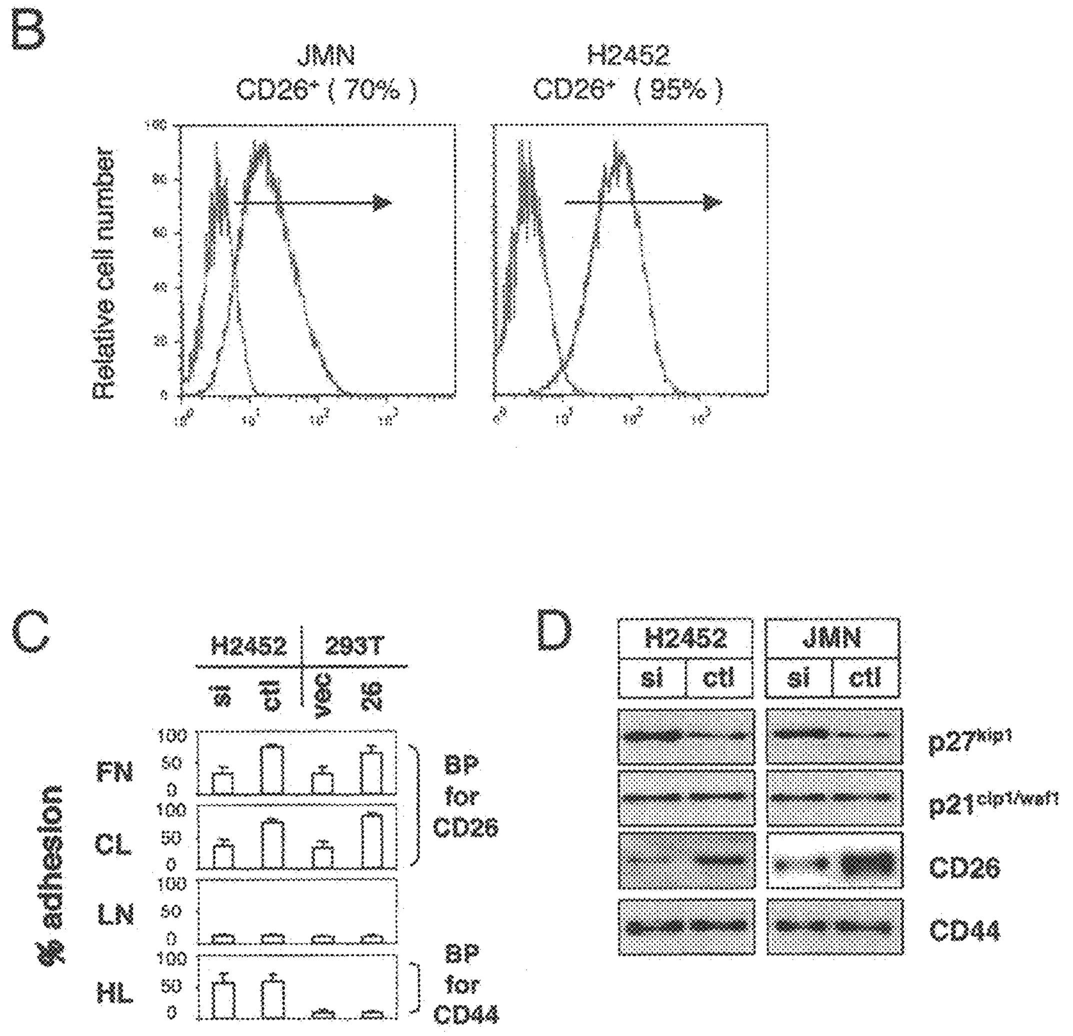

Fig. 5 A - B
A
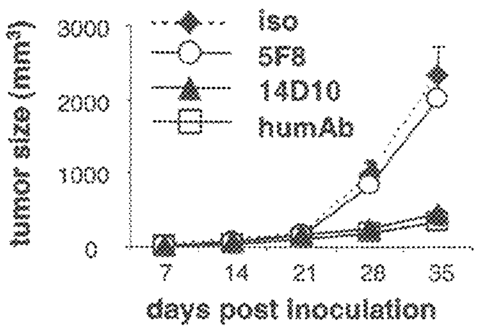
B
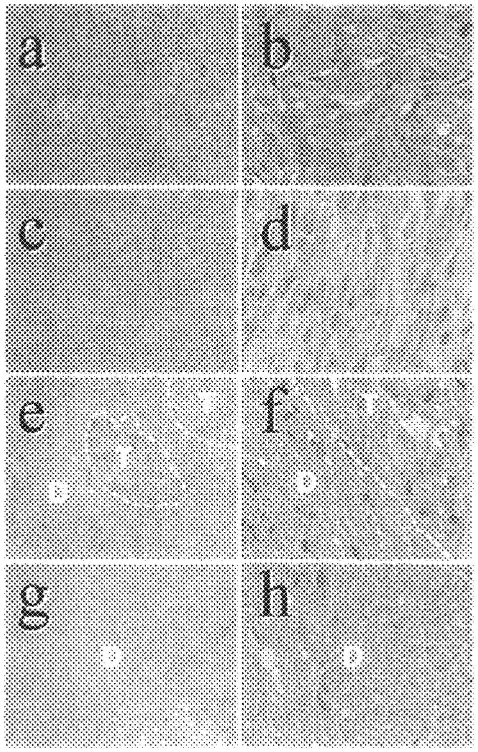

Fig. 5C - D
C
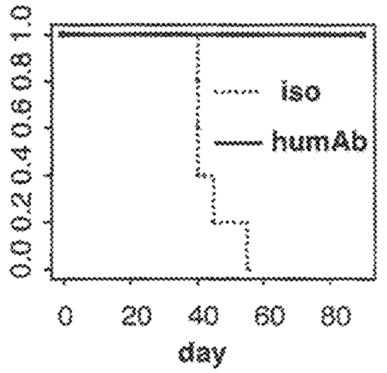
D
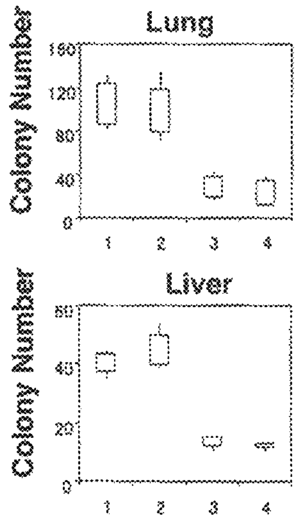

METHOD OF TREATING MALIGNANT MESOTHELIOMA

CROSS REFERENCE TO RELATED APPLICATIONS

This is a divisional application of application Ser. No. 12/450,223, filed Sep. 25, 2009, which is the national stage entry of PCT/JP2008/055344, filed Mar. 14, 2008, which claims priority to U.S. Provisional Application No. 60/894, 786, filed Mar. 14, 2007. The contents of these applications are hereby incorporated by reference in their entirety.

FIELD OF THE INVENTION

The present invention relates to a therapeutic agent for malignant mesothelioma and a method of treating malignant mesothelioma.

BACKGROUND

Malignant mesothelioma (MM) is an aggressive cancer arising from the mesothelial cells lining the pleura. MM is usually associated with history of chronic asbestos exposure (1). Because of the long latency period between asbestos exposure and tumor development, the annual incidence of 2500 new cases in US is expected to increase by more than 50% in the coming decade (2). Moreover incidence world wide is projected to rise substantially in the next decades (3). The prognosis is very poor with a mediam survival of 4-12 months despite the therapies currently used, including surgery, radiotherapy and chemotherapy (4). Because of the inefficacy of the conventional treatments, development of novel therapeutic strategies is urgently needed.

CD26 is 110 kDa surface glycoprotein with dipeptidyl peptidase IV (DPPIV) activity, able to cleave selected biological factors to alter their functions (5). CD26/DPPIV is involved in T-lymphocyte costimulation and signal transduction processes (6, 7), and regulates topoisomerase II alpha levels in hematologic malignancies, affecting sensitivity to doxorubicin and etoposide (8). Expressed in various tissues (4, 9), CD26 is involved in the development of certain human cancers (9-12). CD26 is also known to serve as a binding motif for ECM in human and rodents (13, 14). Previously, we reported that CD26 is a collagen binding protein utilizing a CD26-positive JMN cell line derived from malignant mesothelioma (15). Moreover, our previous works have shown that anti-CD26 monoclonal antibody (mAb) inhibits growth of CD26-positive T-cell malignancies (16, 17) and renal cell carcinoma (18).

CD26 structure consists of three regions—an extracellular region, a 22 residue hydrophobic transmembrane domain, and a 6 amino acid cytoplasmic region, with its extracellular region containing a membrane-proximal glycosylated domain, a cysteine-rich domain, and a 260 amino acid C-terminal domain containing DPP IV enzyme activity. Our previous report shows that the murine anti-CD26 mAb 14D10, which recognizes the cell membrane-proximal glycosylated region starting with the 20 amino acid flexible stalk region of human CD26, has a direct anti-tumor effect by inducing GVS arrest while concomitantly blocking the adhesion of cancer cells to the ECM. However, another murine anti-CD26 mAb termed 5F8, which detects the cysteine-rich domain of CD26, lacks this biological activity (18).

Since human malignant mesothelioma (MM) is a highly malignant tumor resistant to apparent conventional treatment, the detection of novel target and development of new treatment strategies for MM is urgently needed (4,19).

SUMMARY OF THE INVENTION

CD26 is a 110 kDa cell surface antigen with a role in tumor development through its association with key intracellular proteins. In the present invention, we analyzed the expression of CD26 in the tissues of patients with malignant mesothelioma and validated the anti-tumor effect of a novel humanized anti-CD26 mAb (humab) which was constructed from a high affinity Fab clone to the 14D10 variable region, by targeting MM, hence concomitantly showing the functional role of CD26 in this neoplasm. Specifically, in the present invention, we show that CD26 is highly expressed on the cell surface of malignant mesothelioma but not benign mesothelium, indicating that CD26 may be a marker of malignancy. Importantly, depletion of CD26 by siRNA oligo transfection results in the loss of adhesive property, suggesting that CD26 is an extracellular matrix (ECM) binding protein. We previously showed that binding of the mouse anti-CD26 monoclonal antibody (mAb) 14D10 induces a direct anti-tumor effect associated with enhanced $p27^{kip1}$ expression, down regulation of CDK2, and dephosphorylation of retinoblastoma substrate. Given these data, we now analyze the function of a newly developed humanized anti-CD26 mAb (humAb) which consists of the high binding affinity Fab clone to the 14D10 variable region. Our in vitro data indicate that humAb induces cell lysis of malignant mesothelioma cells via antibody-dependent cell-mediated cytotoxicity (ADCC) in addition to its direct anti-tumor effect via $p27^{kip1}$ accumulation and disruption of binding to the ECM. In vivo experiments with mouse xenograft models involving human malignant mesothelioma cells demonstrated that humAb treatment drastically inhibits tumor growth in tumor-bearing mice, resulting in enhanced survival. Taken together, our data show that anti-CD26-humAb treatment may have potential clinical use as a novel cancer therapeutic agent in CD26-positive malignant mesothelioma.

Namely, the present invention is directed to the following.

(1) A pharmaceutical composition for treating malignant mesothelioma, lung cancer, renal cancer, liver cancer, or other malignancies associated with CD26 expression, comprising a substance which inhibits binding of CD26 to extracellular matrix.

(2) The pharmaceutical composition according to (1), which is a growth-inhibitory agent for malignant mesothelioma, lung cancer, renal cancer, liver cancer, or other malignancies associated with CD26 expression.

(3) The pharmaceutical composition according to (1), wherein the substance is an siRNA targeting CD26 cDNA.

(4) The pharmaceutical composition according to (1), wherein the substance is an anti-CD26 antibody.

(5) The pharmaceutical composition according to (4), wherein the anti-CD26 antibody is a monoclonal antibody.

(6) The pharmaceutical composition according to (4), wherein the anti-CD26 antibody is 14D10.

(7) The pharmaceutical composition according to (4), wherein the anti-CD26 antibody is humanized.

(8) The pharmaceutical composition according to (7), wherein the humanized antibody comprises a variable region derived from 14D10.

(9) The pharmaceutical composition according to (7), wherein the humanized antibody is produced by the strain designated s604069.YST-pABMC148 (x411) with American Type Culture Collection (ATCC) accession number PTA-7695.

The deposit was made with the ATCC on Jun. 30, 2006, under the provisions of the Budapest Treaty on the International Recognition of the Deposit of Microorganisms for the Purposes of a Patent Procedure, and the deposit was designated with accession number PTA-7695. The sample deposited was "DH5α *Escherichia coli* with a plasmid having insert of heavy and light chain of a humanized monoclonal antibody against human CD26 cDNA," having the strain designation s604069.YST-pABMC148 (x411).

(10) The pharmaceutical composition according to (4), further comprising an effector cell specific to the antibody.

(11) A kit for treating malignant mesothelioma, lung cancer, renal cancer, liver cancer, or other malignancies associated with CD26 expression, comprising an anti-CD26 antibody and an effector cell specific to the antibody.

(12) A method of inhibiting growth of a malignant mesothelioma cell, lung cancer cell, renal cancer cell, liver cancer cell or other malignant cell expressing CD26, which comprises contacting a malignant mesothelioma cell, lung cancer cell, renal cancer cell, liver cancer cell or other malignant cell expressing CD26 with a substance which inhibits binding of CD26 to extracellular matrix.

(13) The method according to (12), wherein the substance is an anti-CD26 antibody or an siRNA targeting CD26 cDNA.

(14) A method of inhibiting growth of a malignant mesothelioma cell, lung cancer cell, renal cancer cell, liver cancer cell, or other malignant cell that expressing CD26, which comprises contacting a malignant mesothelioma cell, lung cancer cell, renal cancer cell, liver cancer cell, or other malignant cell, and an effector cell with an anti-CD26 antibody, wherein the effector cell is the cell specific to the antibody.

(15) The method according to (14), wherein the substance is an anti-CD26 antibody or an siRNA targeting CD26 cDNA.

(16) A method of lysing a malignant mesothelioma cell, lung cancer cell, renal cancer cell, liver cancer cell, or other malignant cell expressing CD26, which comprises contacting the mesothelioma cell, lung cancer cell, renal cancer cell, liver cancer cell, or other malignant cell expressing CD26, and an effector cell with an anti-CD26 antibody, wherein the lysis of the cell is caused by antibody-dependent cell-mediated cytotoxicity and wherein the effector cell is the cell specific to the antibody.

(17) A method of detecting malignant transformation of mesothelioma, lung cancer, renal cancer, liver cancer, or other malignancies associated with CD26 expression, which comprises collecting a sample from a patient with mesothelioma, lung cancer, renal cancer, liver cancer, or other malignancies associated with CD26 expression, and measuring the expression level of CD26 in the sample.

(18) A diagnostic agent for malignant mesothelioma, lung cancer, renal cancer, liver cancer, or other malignancies associated with CD26 expression, comprising an anti-CD26 antibody.

(19) A kit for diagnosing malignant mesothelioma, lung cancer, renal cancer, liver cancer, or other malignancies associated with CD26 expression comprising an anti-CD26 antibody.

(20) A method of screening a substance for treating malignant mesothelioma, lung cancer, renal cancer, liver cancer, or other malignancies associated with CD26 expression, which comprises contacting a CD26-positive cell with a test substance, and measuring the expression level of p27 in the cell.

(21) Use of a substance as defined in (1) to (10) for producing a pharmaceutical composition in a treatment of malignant mesothelioma, lung cancer, renal cancer, liver cancer, or other malignancies associated with CD26 expression.

(22) A substance as defined in (1) to (10) in a treatment of malignant mesothelioma, lung cancer, renal cancer, liver cancer, or other malignancies associated with CD26 expression.

(23) A method of treating malignant mesothelioma, lung cancer, renal cancer, liver cancer, or other malignancies associated with CD26 expression, which comprises administering to a patient an anti-CD26 antibody and an effector cell specific to the antibody.

(24) A method of diagnosing malignant mesothelioma, which comprises collecting a sample from a patient, and measuring the expression level of CD26 in the sample.

The method according to (24) is useful for differential diagnosis of malignant mesothelioma, lung cancer, renal cancer, liver cancer, or other malignancies associated with CD26 expression from primary lung cancer.

The adminstered substance may enhance $p27^{kip1}$ expression and/or disrupt binding of CD26 to ECM to exhibit anti-tumor effects on the malignant mesothelioma. When the administered substance is the anti-CD26 antibody, the antibody may utilize an effector cell to cause ADCC-induced malignant mesothelioma cell lysis.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

A. Immunohistochemical localization of CD26 in adenomatoid tumor, reactive mesothelial cells, and MM. a, CD26 in adenomatoid tumor; b, CD26 in reactive mesothelial cells; c, CD26 in localized MM; d, CD26 in well-differentiated papillary MM; e and f, H&E stain in diffuse MM; g and h, CD26 in diffuse MM. Diffuse MM specimens showing biphasic features of sarcomatous MM (f, h) and epithelial MM (g, i). Indicated panels are representative of 12 consecutive specimens. Original magnification×100.

FIG. 1B-D. Expression and functional role of CD26 in MM.

B. Surface expression of CD26 on mesothelioma cell lines was analyzed by flow cytometry. Right lines, CD26 histograms were obtained by staining with mouse anti-CD26 mAb (14D10) followed by staining with rabbit anti-mouse Igb FITC conjugate. Left lines, control histograms represent background fluorescence obtained by staining of isotype-matched control mAb (2H4).

C. Adhesive property of CD26 to ECM. CD26-depleted NCI-H2452 (si), scrambled control oligo-transfected NCI-H2452 (ctl), pEB6 vector-transfected 293T (vec), or pEB6-CD26-transfected 293T (26) were plated onto 60 mm dishes ($2\times10^6$ cells per dish) coated with fibronectin (FN), collagen I (CL), laminin (LN), or hyaluronan (HL) and cultured for 18 h. FN and CL are binding proteins (BP) to the extracellular region of CD26, and HL is a CD44 binding protein. The adhesive ability of cancer cells was expressed as the mean number of cells that had attached to the bottom surface of the dish, and the results are presented as mean±SE number of cells per field of view. Values for adhesion were determined by calculating the average number of adhesive cells per $mm^2$ over three fields per assay and expressed as an average of triplicate determinations. Adhesive cells (%): adhesive cells/adhesive cells+nonadhesive cells.

D. Depletion of CD26 elicits upregulation of $p27^{kip1}$. NCI-H2452 cells and JMN cells were transfected with siRNA-oligo of CD26 (si), or control-oligo (ctl). At 48 h after transfection, cells were harvested, lysed, and subjected to SDS-PAGE and probed with antibodies to $p27^{kip1}$, $p21^{cip1/waf1}$, CD26, and CD44.

Figure 2:
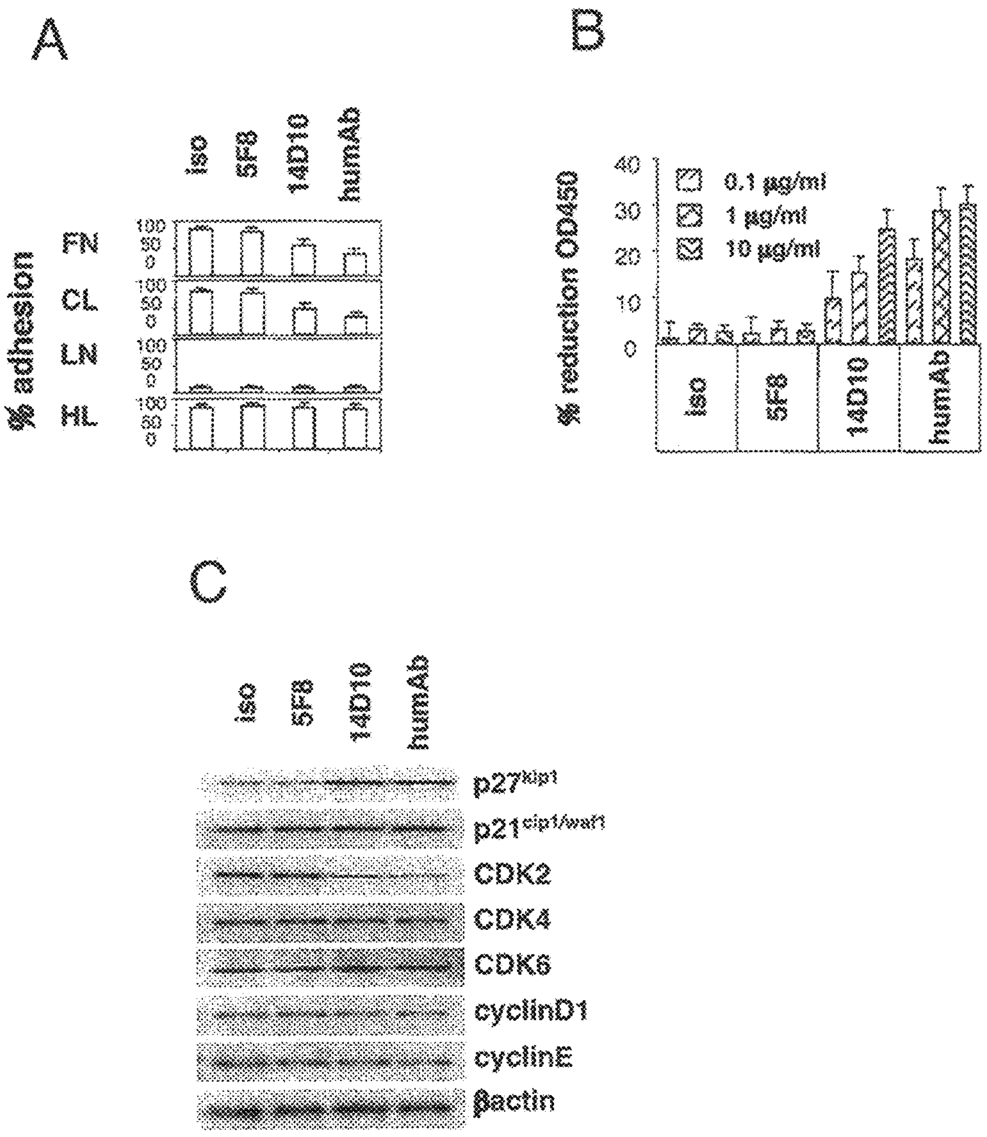

FIG. 2. Inhibitory effect of anti-CD26 mAbs on MM proliferation.

A. Effect of anti-CD26 mAb on cell adhesion to ECM. JMN cells treated with isotype matched control mAb (iso), 5F8, 14D10, or humanized anti-CD26 mAb (humAb) were plated onto 60 mm dishes ($2\times10^6$ cells per dish) coated with fibronectin (FN), collagen (CL), laminin (LN), or hyaluronan (HL) and cultured for 18 h. Adhesive cells (%): adhesive cells/adhesive cells+nonadhesive cells.

B. $5\times10^3$ cells/well of JMN were incubated in 96-well plates in the presence of either isotype matched control mAb (iso), 5F8, 14D10, or humanized anti-CD26 mAb (humAb). After 24 h of antibody treatment, water soluble formazan dye upon bioreduction in the presence of an electron carrier, 1-methoxy-5-methylphenazinium, was measured at 450 nm using a microplate reader as described in Materials and Methods, and growth inhibitory ratio was calculated as % reduction of OD 450 nm.

C. JMN cells were treated with isotype matched control mAb (iso), 5F8, 14D10, or humanized anti-CD26 mAb (humAb). At 18 h after antibody administration, cells were harvested, lysed, and subjected to SDS-PAGE and probed by antibodies to $p27^{kip1}$, $p21^{cip1/waf1}$, CDK2, CDK4, CDK6, cyclinD1, cyclinE, and β-actin.

Figure 3:
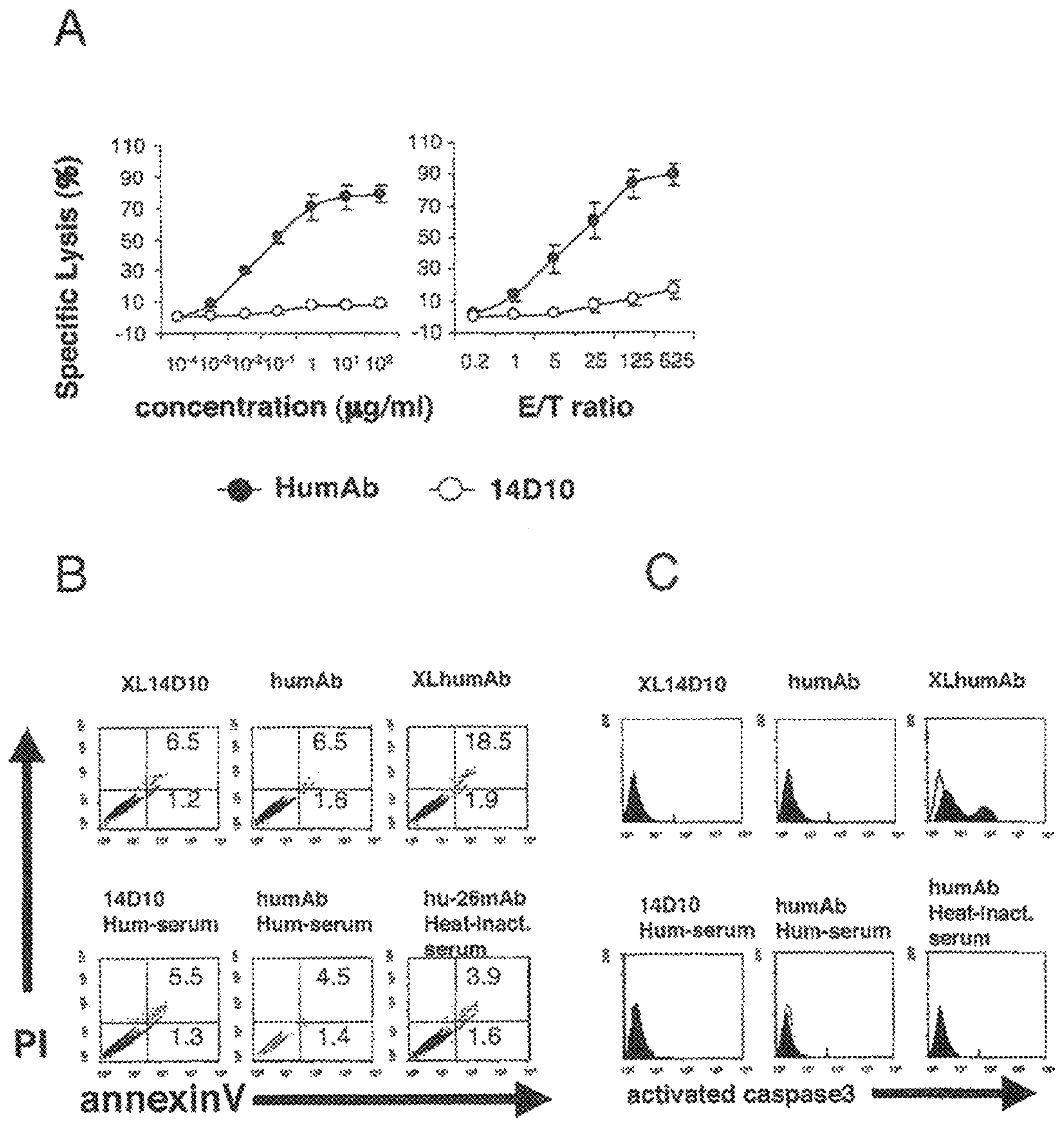

FIG. 3. Antibody-dependent cell-mediated cytotoxicity (ADCC) specific lysis of JMN cells by humanized anti-CD26 mAb.

A. Left panel; ADCC of humanized anti-CD26 mAb (humAb) and 14D10 at the indicated concentrations on the X-axis were examined. Effector/Target (E/T) ratio was held constant at 50. Right panel; ADCC of humanized anti-CD26 mAb (humAb) and 14D10 in the presence of varying E/T ratios were examined. Concentrations of mAbs were held constant at 5 μg/ml. NK cells from a healthy donor were used as effector cells.

B. To mimic effector cells in ADCC effects, cross-linking (XL) method of humanized anti-CD26 mAb (humAb) and 14D10 was utilized. Upper three panels indicate the cross-linked 14D10, intact humAb, cross-linked humAb, respectively. To examine the complementary-dependent cytotoxicity (CDC), human-serum was utilized. Lower three panels indicate 14D10 with serum, humAb with serum, and humAb with heat-inactivated serum. X-axis indicates the annexinV. Y-axis indicates the propidium iodide (PI).

C. Activated caspase 3 was evaluated in JMN cells pre-treated with the cross-linked 14D10, intact humAb, cross-linked humAb, respectively (upper three panels), or in JMN cells pre-treated with the 14D10 plus serum, humAb plus serum, and humAb plus heat-inactivated serum, respectively (lower three panels).

Figure 4:
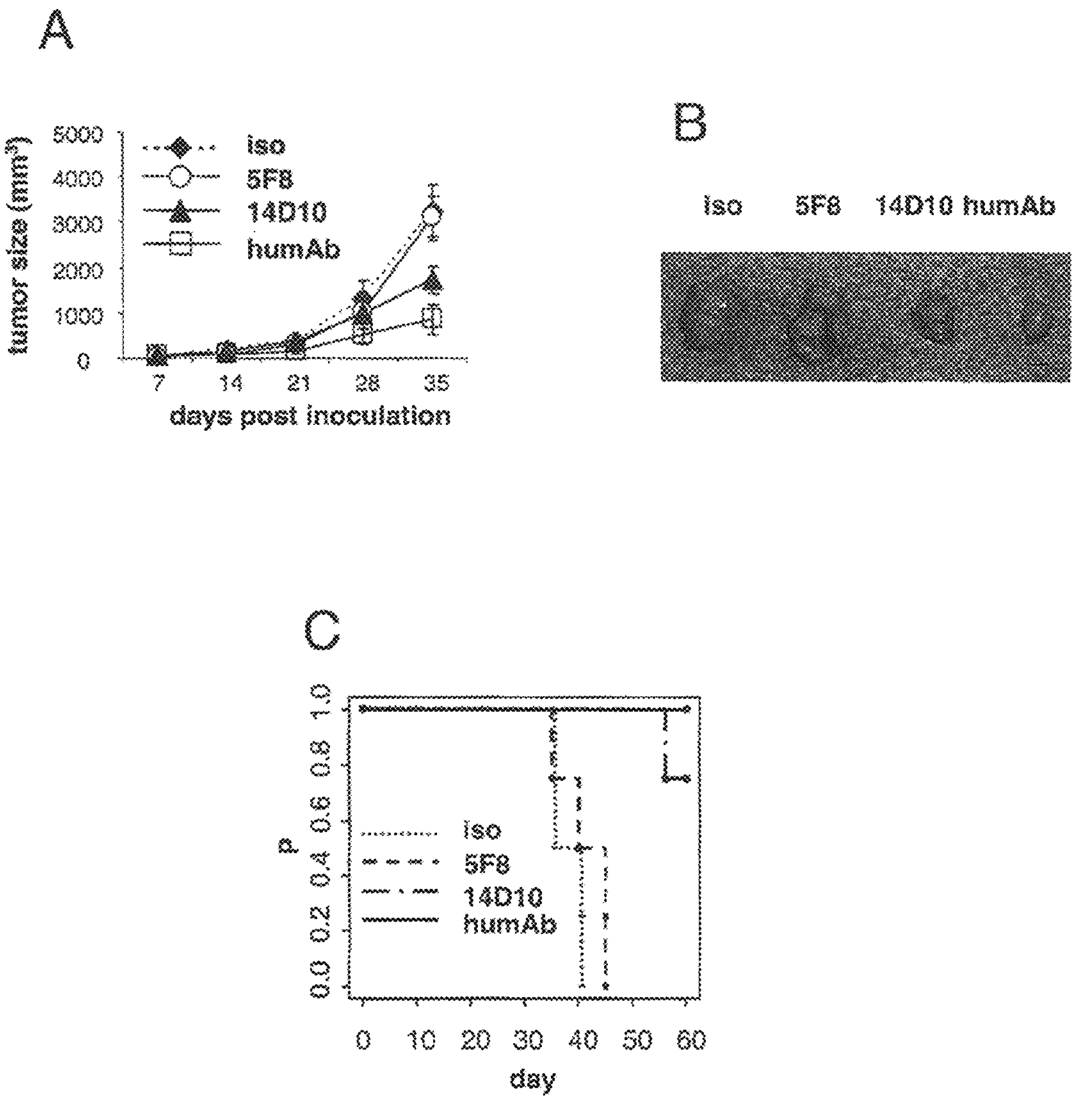

FIG. 4. In vivo direct effect of humanized anti-CD26 mAb: ADCC depletion model. 6 week old female NOD SCID mice were pre-treated with anti-asialo-GM1 polyclonal antisera 1 day before treatment.

A. Effect of humanized anti-CD26 mAb in subcutaneous tumorigenicity was evaluated. JMN cells ($1\times10^6$) were inoculated subcutaneously into the left flank of mice. Mice were treated with intra-tumoral injection of isotype matched control mAb (iso, n=4), 5F8 (n=4), 14D10 (n=4), or humanized anti-CD26 mAb (humAb, n=4) on the 14th day after cancer cell inoculation when the tumor mass became visible (5 mm in size). Each mAb was administered at 10 μg/injection three times per week.

B. Representative resected specimens in subcutaneous tumorigenicity model on 35th day after first mAb treatment.

C. Effect of humanized anti-CD26 mAb in tumor dissemination model was evaluated. JMN cells ($1\times10^5$) were injected intra-venously into mice in each group. Mice were treated with intra-venous injection of isotype matched control mAb (iso, n=4), 5F8 (n=4), 14D10 (n=4), or humanized anti-CD26 mAb (humAb, n=4) on the day of cancer cell injection. Each mAb was administered at 10 μg/injection three times per week.

FIG. 5A-B. In vivo direct and indirect effects of humanized anti-CD26 mAb: mouse ADCC presence model.

6 week old female Balb mice were used in this experiment.

A. Effect of humanized anti-CD26 mAb in subcutaneous tumorigenicity was evaluated. JMN cells ($1\times10^6$) were inoculated subcutaneously into the left flank of mice. Mice were treated with intra-tumoral injection of isotype matched control mAb (iso, n=4), 5F8 (n=4), 14D10 (n=4), or humanized anti-CD26 mAb (humAb, n=4) on the 14th day after cancer cell inoculation when the tumor mass became visible (5 mm in size). Each mAb was administered at 10 μg/injection three times per week.

B. Representative H&E stain of resected specimens in subcutaneous tumorigenicity model on 35th day after first mAb treatment. a, isotype matched control mAb (×100); b, isotype matched control mAb (×600); c, 5F8 (×100); d, 5F8 (×600); e, 14D10 (×100); f, 14D10 (×600); g, humanized anti-CD26 mAb (×100); and h, humanized anti-CD26 mAb (×600). White broken line indicates the boundary between tumor (T) and dead tissue (D).

FIG. 5C-D. In vivo direct and indirect effect of humanized anti-CD26 mAb: mouse ADCC presence model.

C. Effect of humanized anti-CD26 mAb in tumor dissemination model was evaluated. JMN cells ($1\times10^5$) were injected intra-venously into mice in each group. Mice were treated with intra-venous injection of isotype matched control mAb (iso, n=5), or humanized anti-CD26 mAb (humAb, n=5) on the day of cancer cell injection. Each mAb was administered at 10 μg/injection three times per week.

D. Effect of humanized anti-CD26 mAb on distant metastasis formation in the tumor dissemination model was evaluated. JMN cells ($1\times10^5$) were injected intra-venously into mice in each group. Mice were treated with intra-venous injection of isotype matched control mAb (lane 1, n=4), 5F8 (lane 2, n=4), 14D10 (lane 3, n=4), or humanized anti-CD26 mAb (lane 4, n=4) on the day of cancer cell injection. Each mAb was administered at 10 μg/injection three times per week. On 35th day after cancer cell injection, mice were euthanized and multiple metastasis formation in the lung and liver was calculated.

Figure 6:
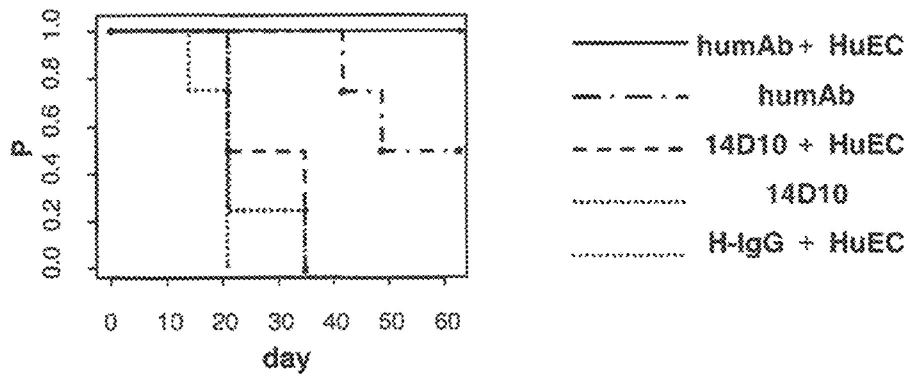

FIG. 6. In vivo direct and indirect effect of humanized anti-CD26 mAb: human ADCC presence model.

6 week old female NOG SCID mice were used in this experiment. Mice were divided into two groups, human effector cells (HuEC)-implanted group and HuEC-negative group, respectively. All mice were pre-treated with anti-asialo-GM1 polyclonal antisera intra-peritoneally 2 days before HuEC implantation. HuEC were implanted intra-peritoneally with effector:target ratio=10:1. JMN cells ($1\times10^6$) were implanted 1 day after HuEC implantation into the peritoneal cavity of mice. The latter group was left untreated. All mice were treated with human normal IgG+HuEC(H-IgG+HuEC, n=4), 14D10 (n=4), 14D10+HuEC (n=4), humanized anti-CD26 mAb (humAb, n=4), or humanized anti-CD26 mAb+HuEC (humAb+HuEC, n=4). Each mAb was i.p. administered at 10 μg/injection, 1, 3, and 5 days after cancer cells implantation.

All publications, patents, patent applications, internet sites, and accession numbers/database sequences (including both polynucleotide and polypeptide sequences) cited herein are hereby incorporated by reference herein in their entirety for all purposes to the same extent as if each individual publication, patent, patent application, internet site, or accession number/database sequence were specifically and individually indicated to be so incorporated by reference.

DETAILED DESCRIPTION

The present invention provides a pharmaceutical composition for treating malignant mesothelioma comprising a substance which inhibits binding of CD26 to extracellular matrix. Examples of the substance include novel polypeptides such as anti-CD26 antibodies and an siRNA targeting CD26 mRNA and/or cDNA.

The present invention provides novel polypeptides such as anti-CD26 antibodies, fragments of anti-CD26 antibodies, and other polypeptides related to anti-CD26 antibodies. In some embodiments, the anti-CD26 antibodies are humanized anti-CD26 antibodies. Polynucleotides comprising nucleic acid sequences encoding the polypeptides are also provided. Vectors and host cells comprising the polynucleotides are also provided. Compositions, such as pharmaceutical compositions, comprising the polypeptides of the invention are also provided. Methods of making the polypeptides are also provided. In addition, methods of using the polypeptides or compositions comprising the polypeptides to inhibit proliferation of cells expressing CD26 or in the treatment or diagnosis of conditions associated with CD26 expression are further provided.

It is understood that wherever embodiments are described herein with the language "comprising," otherwise analogous embodiments described in terms of "consisting of" and/or "consisting essentially of" are also provided.

General Techniques

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

DEFINITIONS

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')2, Fv), single chain (ScFv), mutants thereof, fusion proteins comprising an antibody portion, and any other modified configuration of the immunoglobulin molecule that comprises an antigen recognition site. An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

As used herein, "monoclonal antibody" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by recombinant DNA methods such as described in U.S. Pat. No. 4,816,567. The monoclonal antibodies may also be isolated from phage libraries generated using the techniques described in McCafferty et al., 1990, Nature, 348:552-554, for example.

As used herein, "humanized" antibodies refers to forms of non-human (e.g. murine) antibodies that are specific chimeric immunoglobulins, immunoglobulin chains, or fragments thereof (such as Fv, Fab, Fab', $F(ab')_2$, or other antigen-binding subsequences of antibodies) that contain minimal sequence derived from non-human immunoglobulin. Some humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Some humanized antibodies comprise at least one, and typically two, variable domains that are generally derived from a non-human species (donor antibody) such as a mouse, rat, or rabbit having the desired specificity, affinity, and/or capacity, but in which one or more Fv framework region residues and/or one or more Fv CDR residues have been replaced by a corresponding human residue (i.e., a residue derived from a human antibody sequence). Most typically, at least a plurality of Fv framework region residues will have been replaced in one or more of the variable domains of the humanized antibody. Furthermore, the humanized antibody may comprise residues that are found neither in the recipient antibody nor in the imported CDR or framework sequences, but are included to further refine and optimize antibody performance. Some humanized antibodies will comprise substantially all of at least one, and typically two, variable domains, in which all or substantially all of the CDRs correspond to those of a non-human immunoglobulin and all or substantially all of the FRs are those of a human immunoglobulin consensus sequence. Some humanized antibodies will comprise substantially all of at least one, and typically two, variable domains, in which the majority of the amino acid residues of the CDRs correspond to those of a non-human immunoglobulin and one or more of the amino acid residues of the FRs are those of a human immunoglobulin consensus sequence. A humanized antibody optimally also will comprise at least a portion of an immunoglobulin constant region or domain (Fc), typically that of a human immunoglobulin. Some humanized antibodies have Fc regions modified as described in WO 99/58572. Some forms of humanized antibodies have one or more (e.g., one, two, three, four, five, six) CDRs which are altered with respect to the original antibody, which are also termed one or more CDRs "derived from" one or more CDRs from the original antibody.

As used herein, "human antibody" means an antibody having an amino acid sequence corresponding to that of an antibody produced by a human and/or has been made using any of the techniques for making human antibodies known in the art or disclosed herein. This definition of a human antibody includes antibodies comprising at least one human heavy chain polypeptide or at least one human light chain polypeptide. One such example is an antibody comprising murine light chain and human heavy chain polypeptides. Human antibodies can be produced using various techniques known in the art. In one embodiment, the human antibody is selected from a phage library, where that phage library expresses human antibodies (Vaughan et al., 1996, Nature Biotechnology, 14:309-314; Sheets et al., 1998, PNAS, (USA) 95:6157-6162; Hoogenboom and Winter, 1991, J. Mol. Biol., 227:381; Marks et al., 1991, J. Mol. Biol., 222:581). Human antibodies can also be made by introducing human immunoglobulin loci into transgenic animals, e.g., mice in which the endogenous immunoglobulin genes have been partially or completely inactivated. This approach is described in U.S. Pat. Nos. 5,545,807; 5,545,806; 5,569,825; 5,625,126; 5,633,425; and 5,661,016. Alternatively, the human antibody may be prepared by immortalizing human B lymphocytes that produce an antibody directed against a target antigen (such B lymphocytes may be recovered from an individual or may have been immunized in vitro). See, e.g., Cole et al., Monoclonal Antibodies and Cancer Therapy, Alan R. Liss, p. 77 (1985); Boemer et al., 1991, J. Immunol., 147 (1):86-95; and U.S. Pat. No. 5,750,373. In some embodiments, a human antibody is "fully human," meaning the antibody contains human heavy chain and light chain polypeptides.

The terms "polypeptide", "oligopeptide", "peptide", and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon an antibody, the polypeptides can occur as single chains or associated chains.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), "(O)$NR_2$ ("amidate"), P(O)R, P(O)OR', CO or $CH_2$ ("formacetal"), in which each R or R' is independently H or substituted or unsubstituted alkyl (1-20 C) optionally containing an ether (—O—) linkage, aryl, alkenyl, cycloalkyl, cycloalkenyl, or araldyl. Not all linkages in a polynucleotide need be identical. The preceding description applies to all polynucleotides referred to herein, including RNA and DNA.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al (1997) J. Molec. Biol. 273:927-948)). In addition, combinations of these two approaches are sometimes used in the art to determine CDRs.

A "constant region" of an antibody refers to the constant region of the antibody light chain or the constant region of the antibody heavy chain, either alone or in combination.

An epitope that "preferentially binds" or "specifically binds" (used interchangeably herein) to an antibody or a polypeptide is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a CD26 epitope is an antibody that binds this CD26 epitope with greater affinity, avidity, more readily, and/or with greater duration than it binds to other CD26 epitopes or non-CD26 epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cell, or compositions include those which have been purified to a degree that they are no longer in a form in which they are found in nature. In some embodiments, an antibody, polynucleotide, vector, cell, or composition which is isolated is substantially pure.

As used herein, "treatment" is an approach for obtaining beneficial or desired clinical results. For purposes of this invention, beneficial or desired clinical results include, but are not limited to, alleviation of one or more symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment.

An "effective amount" is an amount sufficient to effect beneficial or desired clinical results including clinical results. An effective amount can be administered in one or more administrations. For purposes of this invention, an effective amount of a polypeptide, such as an anti-CD26 antibody, described herein is an amount sufficient to ameliorate, stabilize, reverse, slow and/or delay progression of a condition associated with CD26 expression. As is understood in the art, an effective amount of, for example, an anti-CD26 antibody may vary, depending on, inter alia, patient history as well as other factors such as the type (and/or dosage) of an anti-CD26 antibody used. As evident by this disclosure to one skilled in the art, these principles apply to polypeptide embodiments.

An "individual," also referred to herein as a "subject," is a vertebrate, preferably a mammal, more preferably a human. Mammals include, but are not limited to, farm animals (such as cows), sport animals, pets (such as cats, dogs, and horses), primates, mice and rats.

As used herein, "vector" means a construct, which is capable of delivering, and preferably expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "pharmaceutically acceptable carrier" or "pharmaceutically acceptable excipient" includes any material which, when combined with an active ingredient, allows the ingredient to retain biological activity and is non-reactive with the subject's immune system and non-toxic to the subject when delivered. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline. Compositions comprising such carriers are formulated by well known conventional methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000).

Anti-CD26 Antibody

In some embodiments, the polypeptides described herein preferentially bind to the one or more peptides. These peptides are regions of human CD26. In some embodiments, the polypeptides described herein bind to the same epitope as the mouse monoclonal antibody 14D10. In some embodiments, the polypeptides described herein are capable of blocking the binding of mouse monoclonal antibody 14D10 to human CD26 in a competition assay. In some embodiments, the polypeptides described herein are capable of blocking the binding of mouse monoclonal antibody 1F7 to human CD26 in a competition assay.

Methods of determining affinity are known in the art. For instance, binding affinity may be determined using a BIAcore biosensor, a KinExA biosensor, scintillation proximity assays, ELISA, ORIGEN immunoassay (IGEN), fluorescence quenching, fluorescence transfer, and/or yeast display. Binding affinity may also be screened using a suitable bioassay.

One way of determining binding affinity of antibodies to CD26 is by measuring affinity of monofunctional Fab fragments of the antibodies. To obtain monofunctional Fab fragments, antibodies, for example, IgGs can be cleaved with papain or expressed recombinantly. Affinities of anti-CD26 Fab fragments of monoclonal antibodies can be determined by Surface Plasmon Resonance (SPR) system (BIAcore 3000™, BIAcore, Inc., Piscaway, N.J.). SA chips (streptavidin) are used according to the supplier's instructions. Biotinylated CD26 can be diluted into HBS-EP (100 mM HEPES pH 7.4, 150 mM NaCl, 3 mM EDTA, 0.005% P20) and injected over the chip at a concentration of 0.005 mg/mL. Using variable flow time across the individual chip channels, two ranges of antigen density are achieved: 10-20 response units (RU) for detailed kinetic studies and 500-600 RU for concentration. A mixture of Pierce elution buffer and 4 M NaCl (2:1) effectively removes the bound Fab while keeping the activity of CD26 on the chip for over 200 injections. HBS-EP buffer can be used as running buffer for all the BIAcore assays. Serial dilutions (0.1-10× estimated $K_D$) of purified Fab samples are injected for 2 min at 100 μL/min and dissociation times of up to 30 min are generally allowed. The concentrations of the Fab proteins can be determined by ELISA and/or SDS-PAGE electrophoresis using a standard Fab of known concentration (determined by amino acid analysis). Kinetic association rates ($k_{on}$) and dissociation rates ($k_{off}$) are obtained simultaneously by fitting the data to a 1:1 Langmuir binding model (Lofas & Johnsson, 1990) using the BIAevaluation program. Equilibrium dissociation constant ($K_D$) values are calculated as $k_{off}/k_{on}$.

In some embodiments, the invention encompasses polypeptides, such as antibodies, which inhibit proliferation of cells expressing CD26. The invention also encompasses embodiments where the polypeptides are useful in the treatment of a condition (such as a disease or disorder) associated with CD26 expression (e.g., a malignant mesothelioma). In some embodiments, the polypeptides (e.g., antibodies) of the invention may have one or more of the following characteristics: (a) bind CD26; (b) modulate CD26 activity, (c) cause cell cycle arrest of CD26+ cells at the G1/S checkpoint; (d) inhibit proliferation of cells expressing CD26 (e.g., malignant mesothelioma), (e) inhibit binding of CD26 to extracellular matrix, and/or (f) are useful in the treatment of a condition associated with CD26 expression. In some embodiments, the condition associated with CD26 expression is a disease or disorder associated with CD26 overexpression. In some embodiments, the condition associated with CD26 expression is mediated, at least in part, by CD26. In some embodiments, the condition associated with CD26 expression is a condition associated with the proliferation of cells expressing CD26. In some embodiments, the disease or disorder is a cancer (e.g., malignant mesothelioma, lung cancer, renal cancer, liver cancer, or other malignancies associated with CD26 expression), an autoimmune disease or disorder, graft versus host disease (GVHD), or an inflammatory disease or disorder.

In some embodiments, the antibody comprises both a heavy chain variable region comprising an amino acid sequence having at least about 80% identity to an amino acid sequence selected from the group consisting of SEQ ID NOS: 8-14 and a light chain variable region comprising an amino acid sequence having at least about 80% identity to an amino acid sequence selected from the group consisting of SEQ ID NOS:1-7. In some embodiments, the antibody comprises a light chain variable region comprising an amino acid sequence selected from the group consisting of SEQ ID NOS: 1-7 and a heavy chain variable region comprising an amino acid sequence selected from the group consisting of SEQ ID NOS:8-14.

In some embodiments, the polypeptide comprises at least 5 contiguous amino acids, at least 8 contiguous amino acids, at least about 10 contiguous amino acids, at least about 15 contiguous amino acids, at least about 20 contiguous amino acids, at least about 30 contiguous amino acids, or at least about 50 contiguous amino acids of an amino acid sequence of any one of SEQ ID NOS:1-14.

The invention further provides polypeptides comprising fragments of the polypeptide sequences described herein (e.g., any one of SEQ ID NOS:1-7, SEQ IDS NOS:8-14, SEQ IDS NO:15, or SEQ IDS NO:16). In some embodiments, the polypeptide comprises a fragment of a polypeptide sequence described herein, wherein the fragment is at least about 10 amino acids in length, at least about 25 amino acids in length, at least about 50 amino acids in length, at least about 75 amino acids in length, or at least about 100 amino acids in length.

SEQ ID NO: 15

EVQLV$X_1$SG$X_2X_3X_4X_5$QPG$X_6X_7$LRL$X_8$C$X_9$ASG$X_{10}X_{11}$L$X_{12}$TYGVHWVRQAPGKGLEW$X_{13}$GVIWG$X_{14}$GRTDYD$X_{15}X_{16}$FMSRVTIS$X_{17}$D$X_{18}$SK$X_{19}$T$X_{20}$YLQ$X_{21}$NSLRAEDTAVYYC$X_{22}$R$X_{23}$RHDWFDYWGQGTTVTVSS, wherein $X_1$ is E or Q, $X_2$ is A or G, $X_3$ is G or E, $X_4$ is L or V, $X_5$ is V, K, or E, $X_6$ is G or E, $X_7$ is T or S, $X_8$ is T or S, $X_9$ is T or K, $X_{10}$ is F or Y, $X_{11}$ is S or T, $X_{12}$ is T, N, or S, $X_{13}$ is V or M, $X_{14}$ is G or D, $X_{15}$ is A or S, $X_{16}$ is A or S, $X_{17}$ is K or R, $X_{18}$ is N or T, $X_{19}$ is S or N, $X_{20}$ is V or A, $X_{21}$ is M or L, $X_{22}$ is V, M, or T, and $X_{23}$ is N or S.

SEQ ID NO: 16

$X_1$I$X_2X_3$TQSPSSLS$X_4X_5X_6$G$X_7$R$X_8$TI$X_9$C$X_{10}$ASQ$X_{11}$IRN$X_{12}$LNWYQQKPGQAPRLLIYYSSNL$X_{13}X_{14}$GVP$X_{15}$RFSGSGSGTDFTLTISRL$X_{16}X_{17}$ED$X_{18}$A$X_{19}$YYCQQS$X_{20}$KLP$X_{21}$TFGSGTKVEIK, wherein $X_1$ is D or E, $X_2$ is L or E, $X_3$ is M or L, $X_4$ is A or V, $X_5$ is S or T, $X_6$ is L, P, or A, $X_7$ is D or E, $X_8$ is V or A, $X_9$ is T or S, $X_{10}$ is S or R, $X_{11}$ is G or D, $X_{12}$ is S or N, $X_{13}$ is H or Q, $X_{14}$ is S or T, $X_{15}$ is S, D, or A, $X_{16}$ is E or Q, $X_{17}$ is P or A, $X_{18}$ is F or V, $X_{19}$ is T, A, or I, $X_{20}$ is I or N and $X_{21}$ is F or L.

Table 1 shows the amino acid sequences of humanized VL variants X376 (SEQ ID NO:1), X377 (SEQ ID NO:2), X378 (SEQ ID NO:3), X379 (SEQ ID NO:4), X380 (SEQ ID NO:5), X381 (SEQ ID NO:6), and X394 (SEQ ID NO:7). Kabat and sequential numbering schemes are identical for the light chain variable regions.

Table 2 shows the amino acid sequences of humanized VH variants X384 (SEQ ID NO:8), X385 (SEQ ID NO:9), X386 (SEQ ID NO:10), X387 (SEQ ID NO:11) and X388 (SEQ ID NO:12), X399 (SEQ ID NO:13) and X420 (SEQ ID NO:14). Both the sequential and Kabat numbering schemes are shown. The Kabat numbering scheme includes 82a, 82b, and 82c.

TABLE 1

| | |
|---|---|
| | 10 20 30 40 50 |
| Sequential | 12345678901234567890123456789012345678901234567890123456 |
| Numbering | <---------FR1---------><--CDR1---><-----FR2-----><CDR2-> |

TABLE 1-continued

| | |
|---|---|
| Cm03 VL | DIQMTQSPSSLSASLGDRVTITCSASQGIRNSLNWYQQKPDGAVKLLIYYSSNLHS |
| X376 | DILMTQSPSSLSASPGDRVTISCRASQDIRNNLNWYQQKPGQAPRLLIYYSSNLHS |
| X377 | EIELTQSPSSLSVSLGDRVTISCSASQDIRNNLNWYQQKPGQAPRLLIYYSSNLQT |
| X378 | DIEMTQSPSSLSASAGERVTISCRASQGIRNSLNWYQQKPGQAPRLLIYYSSNLQT |
| X379 | DILLTQSPSSLSATPGERATITCRASQGIRNNLNWYQQKPGQAPRLLIYYSSNLQS |
| X380 | EIEMTQSPSSLSVSAGERATISCSASQDIRNSLNWYQQKPGQAPRLLIYYSSNLHT |
| X381 | EIELTQSPSSLSVSPGDRVTISCSASQGIRNSLNWYQQKPGQAPRLLIYYSSNLHT |
| X394 | DILMTQSPSSLSASPGDRVTISCRASQDIRNNLNWYQQKPGQAPRLLIYYSSNLQT |
| Kabat Numbering | 24 34 50 56 |
| (same as sequential numbering; no insertion) | |
| | 60 70 80 90 100 |
| Sequential Numbering | 789012345678901234567890123456789012345678901234567 |
| | <-------------FR3-------------><-CDR3--><--FR4---> |
| Cm03 VL | GVPSRFSGSGSGTDFSLTISNLEPEDIATYYCQQSIKLPFTFGSGTKLEIK |
| X376 | GVPDRFSGSGSGTDFTLTISRLEPEDFAAYYCQQSIKLPLTFGSGTKVEIK |
| X377 | GVPARFSGSGSGTDFTLTISRLEPEDVAAYYCQQSIKLPFTFGSGTKVEIK |
| X378 | GVPSRFSGSGSGTDFTLTISRLQAEDFATYYCQQSNKLPFTFGSGTKVEIK |
| X379 | GVPSRFSGSGSGTDFTLTISRLQPEDVAAYYCQQSIKLPFTFGSGTKVEIK |
| X380 | GVPARFSGSGSGTDFTLTISRLEPEDVAIYYCQQSNKLPLTFGSGTKVEIK |
| X381 | GVPARFSGSGSGTDFTLTISRLQAEDFATYYCQQSIKLPLTFGSGTKVEIK |
| X394 | GVPARFSGSGSGTDFTLTISRLEPEDFAAYYCQQSIKLPLTFGSGTKVEIK |
| Kabat Numbering | 89 97 |
| (same as sequential numbering; no insertion) | |

TABLE 2

| | |
|---|---|
| | 10 20 30 40 50 60 |
| Sequential Numbering | 12345678901234567890123456789012345678901234567890123456789012345 |
| | <----------FR1----------><--CDR1--><----FR2-----><----CDR2------> |
| CM03 VH | QVKLQESGPGLVQPSQTLSITCTVSGFSLTTYGVHWVRQSPGKGLEWLGVIWGGGRTDYDAAFIS |
| X384 | EVQLVESGAGVKQPGGTLRLTCTASGFSLTTYGVHWVRQAPGKGLEWVGVIWGDGRTDYDAAFMS |
| X385 | EVQLVQSGGGVKQPGETLRLTCTASGFSLTTYGVHWVRQAPGKGLEWVGVIWGDGRTDYDAAFMS |
| X386 | EVQLVESGAGVEQPGGTLRLTCTASGFSLTTYGVHWVRQAPGKGLEWMGVIWGDGRTDYDAAFMS |
| X387 | EVQLVESGAELVQPGGSLRLTCKASGFTLNTYGVHWVRQAPGKGLEWMGVIWGGGRTDYDASFMS |
| X388 | EVQLVQSGGGLKQPGETLRLSCTASGYSLTTYGVHWVRQAPGKGLEWMGVIWGDGRTDYDSSFMS |
| X399 | EVQLVQSGGGVKQPGETLRLTCTASGFSLSTYGVHWVRQAPGKGLEWVGVIWGDGRTDYDAAFMS |
| X420 | EVQLVESGGGVKQPGETLRLTCTASGFSLSTYGVHWVRQAPGKGLEWVGVIWGDGRTDYDAAFMS |
| Kabat Numbering | 26 35 50 65 |
| | 70 80 90 100 110 |
| Sequential Numbering | 678901234567890123456789012345678901234567890123456 |
| | <-------------FR3-------------><-CDR3-><--FR4----> |
| CM03 VH | RLSISKDNSKSQYFFKMNSLQANDTAIYYCVRNRHDWFDYWGQGTTVTVSS |
| X384 | RVTISKDTSKSTVYLQMNSLRAEDTAVYYCMRNRHDWFDYWGQGTTVTVSS |
| X385 | RVTISKDTSKSTAYLQMNSLRAEDTAVYYCMRNRHDWFDYWGQGTTVTVSS |
| X386 | RVTISRDTSKSTAYLQLNSLRAEDTAVYYCVRNRHDWFDYWGQGTTVTVSS |
| X387 | RVTISKDNSKNTAYLQLNSLRAEDTAVYYCTRSRHDWFDYWGQGTTVTVSS |
| X388 | RVTISKDTSKSTAYLQLNSLRAEDTAVYYCTRNRHDWFDYWGQGTTVTVSS |
| X399 | RVTISKDTSKSTVYLQMNSLRAEDTAVYYCMRNRHDWFDYWGQGTTVTVSS |
| X420 | RVTISKDTSKSTVYLQMNSLRAEDTAVYYCMRNRHDWFDYWGQGTTVTVSS |
| Kabat Numbering | abc3456789012345678901234567890123 |
| | 82 90 100 110 |
| | 95 102 |

The invention further provides a polypeptide (e.g., an antibody) comprising SEQ ID NO:17, or a fragment or variant thereof. In some embodiments, the polypeptide comprises SEQ ID NO: 17. In some embodiments, the polypeptide comprises SEQ ID NO:17 except for the signal sequence. (One of ordinary skill in the art will readily appreciate that in some embodiments, the signal sequence of a polypeptide is cleaved off of the polypeptide.) In some embodiments, the polypeptide comprises the variable region of SEQ ID NO:17. In some embodiments, the polypeptide comprises a polypeptide having at least about 80%, at least about 85%, at least about 90%, at least about 95%, or at least about 98% identity to SEQ ID NO:17 (or a fragment thereof). In some embodiments, the polypeptide comprises a fragment of SEQ ID NO:17, wherein the fragment is at least about 10 amino acids in length, at least about 25 amino acids in length, at least about 50 amino acids in length, at least about 75 amino acids in length, or at least about 100 amino acids in length. In some embodiments, the polypeptide binds human CD26.

Heavy chain (SEQ ID NO: 17):
MEWSWVFLFFLSVTTGVHS*EVQLVESGAGVKQPGGTLRLTCTASG*

*FSLTTYGVHWVRQAPGKGLEWVGVIW*

*GDGRTDYDAAFMSRVTISKDTSKSTVYLQMNSLRAEDTAV*

*YYCMRNRHDWFDYWGQGTTVTVSS*

-continued

ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK

The invention further provides a polypeptide (e.g., an antibody) comprising SEQ ID NO:18, or a fragment or variant thereof. In some embodiments, the polypeptide comprises SEQ ID NO:18. In some embodiments, the polypeptide comprises SEQ ID NO:18 except for the signal sequence. (One of ordinary skill in the art will readily appreciate that in some embodiments, the signal sequence of a polypeptide is cleaved off of the polypeptide.) In some embodiments, the polypeptide comprises the variable region of SEQ ID NO:18. In some embodiments, the polypeptide comprises a polypeptide having at least about 80%, at least about 85%, at least about 90%, at least about 95%, or at least about 98% identity to SEQ ID NO:18 (or a fragment thereof). In some embodiments, the polypeptide comprises a fragment of SEQ ID NO:18, wherein the fragment is at least about 10 amino acids in length, at least about 25 amino acids in length, at least about 50 amino acids in length, at least about 75 amino acids in length, or at least about 100 amino acids in length. In some embodiments, the polypeptide further comprises SEQ ID NO:18, or a fragment or variant thereof. In some embodiments, the polypeptide binds human CD26. For instance, in some embodiments, the polypeptide is an antibody comprising at least one heavy chain (e.g., two heavy chains), each of which comprises SEQ ID NO:17 without the signal sequence, and at least one light chain (e.g., two light chains), each of which comprises SEQ ID NO:18 without the signal sequence.

Light chain (SEQ ID NO: 18):
MSVPTQVLGLLLLWLTDARC*DILLTQSPSSLSATPGE*

*RATITCRASQGIRNNLNWYQQKPGQAPRLLIYYSSNL*

*QSGVPSRFSGSGSGTDFTLTISRLQPEDVAAYYC*

*QQSIKLPFTFGSGTKVEIK*RTVAAPSVFIFPPSDEQL

KSGTASVVCLLNNFYPREAKVQWKVDNALQSGNSQESVTEQDSKD

STYSLSSTLTLSKADYEKHKVYACEVTHQGLSSPVTKSFNRGEC

In another aspect, the invention provides a polypeptide, such as an antibody, that binds to one or more peptides selected from the group consisting of YSLRWISDHEYLY (SEQ ID NO:19; peptide 6), LEYNYVKQWRHSY (SEQ ID NO:20; peptide 35), TWSPVGHKLAYVW (SEQ ID NO:21; peptide 55), LWWSPNGTFLAYA (SEQ ID NO:22; peptide 84), RISLQWLRRIQNY (SEQ ID NO:23; peptide 132), YVKQWRHSYTASY (SEQ ID NO:24; peptide 37), EEEVFSAYSALWW (SEQ ID NO:25; peptide 79), DYSISPDGQFILL (SEQ ID NO:26; peptide 29), SISPDGQFILLEY (SEQ ID NO:27; peptide 30), and IYVKIEPNLPSYR (SEQ ID NO:28; peptide 63). In some embodiments, the polypeptide preferentially binds to the one or more peptides. These peptides are regions of human CD26. In some embodiments, the polypeptide preferentially binds to one or more peptides selected from the group consisting of YSLRWISDHEYLY (SEQ ID NO:19; peptide 6), LEYNYVKQWRHSY (SEQ ID NO:20; peptide 35), TWSPVGHKLAYVW (SEQ ID NO:21; peptide 55), LWWSPNGTFLAYA (SEQ ID NO:22; peptide 84), RISLQWLRRIQNY (SEQ ID NO:23; peptide 132), YVKQWRHSYTASY (SEQ ID NO:24; peptide 37), EEEVFSAYSALWW (SEQ ID NO:25; peptide 79), DYSISPDGQFILL (SEQ ID NO:26; peptide 29), SISPDGQFILLEY (SEQ ID NO:27; peptide 30), and IYVKIEPNLPSYR (SEQ ID NO:28; peptide 63), relative to one or more peptides corresponding to other regions of human CD26.

In some embodiments, the polypeptide (e.g., antibody) binds to each of the following peptides: YSLRWISDHEYLY (SEQ ID NO:19; peptide 6); LEYNYVKQWRHSY (SEQ ID NO:20; peptide 35); TWSPVGHKLAYVW (SEQ ID NO:21; peptide 55); LWWSPNGTFLAYA (SEQ ID NO:22; peptide 84); and RISLQWLRRIQNY (SEQ ID NO:23; peptide 132). In some other embodiments, the polypeptide binds to each of the following peptides: YSLRWISDHEYLY (SEQ ID NO:19; peptide 6); TWSPVGHKLAYVW (SEQ ID NO:21; peptide 55); RISLQWLRRIQNY (SEQ ID NO:23; peptide 132); YVKQWRHSYTASY (SEQ ID NO:24; peptide 37); and EEEVFSAYSALWW (SEQ ID NO:25; peptide 79). In some embodiments, the polypeptide binds to each of the following peptides: DYSISPDGQFILL (SEQ ID NO:26; peptide 29); SISPDGQFILLEY (SEQ ID NO:27; peptide 30); and TWSPVGHKLAYVW (SEQ ID NO:21; peptide 55). In some other embodiments, the polypeptide binds to each of the following peptides: DYSISPDGQFILL (SEQ ID NO:26; peptide 29); SISPDGQFILLEY (SEQ ID NO:27; peptide 30); TWSPVGHKLAYVW (SEQ ID NO:21; peptide 55); and IYVKIEPNLPSYR (SEQ ID NO:28; peptide 63). In some embodiments, the polypeptides preferentially bind to the specified peptides.

Competition assays can be used to determine whether two antibodies bind the same epitope by recognizing identical or sterically overlapping epitopes. Typically, antigen is immobilized on a multi-well plate and the ability of unlabeled antibodies to block the binding of labeled antibodies is measured. Common labels for such competition assays are radioactive labels or enzyme labels. In addition, epitope mapping techniques known to those in the art can be used to determine the epitopes to which antibodies bind.

In some embodiments, a polypeptide described herein comprises one or more constant regions. In some embodiments, a polypeptide described herein comprises a human constant region. In some embodiments, the constant region is a constant region of the heavy chain. In other embodiments, the constant region is a constant region of the light chain. In some embodiments, the polypeptide comprises a constant region which has at least about 80%, at least about 85%, at least about 90%, at least about 95%, at least about 98%, or 100% identity to a human constant region. In some embodiments, a polypeptide (e.g., an antibody) described herein comprises an Fc region. In some embodiments, the polypeptide comprises a human Fc region. In some embodiments, a polypeptide described herein comprises an Fc region which has at least about 80%, at least about 85%, at least about 90%, at least about 95%, at least about 98%, or 100% identity to a human Fc region.

In some embodiments, an antibody described herein is an IgG antibody. In some embodiments, the antibody is an IgG1 antibody. In some other embodiments, the antibody is an IgG2 antibody. In some embodiments, the antibody is a human IgG antibody.

The invention provides antibodies in monomeric, dimeric, and multivalent forms. For example, bispecific antibodies, monoclonal antibodies that have binding specificities for at least two different antigens, can be prepared using the antibodies disclosed herein. Methods for making bispecific antibodies are known in the art (see, e.g., Suresh et al., 1986, Methods in Enzymology 121:210). Traditionally, the recombinant production of bispecific antibodies was based on the coexpression of two immunoglobulin heavy chain-light chain pairs, with the two heavy chains having different specificities (Millstein and Cuello, 1983, Nature 305, 537-539).

According to one approach to making bispecific antibodies, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2 and CH3 regions. It is preferred to have the first heavy chain constant region (CH1), containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one approach, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure, with an immunoglobulin light chain in only one half of the bispecific molecule, facilitates the separation of the desired bispecific compound from unwanted immunoglobulin chain combinations. This approach is described in PCT Publication No. WO 94/04690, published Mar. 3, 1994.

Heteroconjugate antibodies, comprising two covalently joined antibodies, are also within the scope of the invention. Such antibodies have been used to target immune system cells to unwanted cells (U.S. Pat. No. 4,676,980), and for treatment of HIV infection (PCT application publication Nos. WO 91/00360 and WO 92/200373; EP 03089). Heteroconjugate antibodies may be made using any convenient cross-linking methods. Suitable cross-linking agents and techniques are well known in the art, and are described in U.S. Pat. No. 4,676,980.

In certain embodiments, an antibody described herein is an antibody fragment. For instance, in some embodiments, the antibody is selected from the group consisting of Fab, Fab', Fab'-SH, Fv, scFv, and $F(ab')_2$. In some embodiments, the antibody is a Fab. Various techniques have been developed for the production of antibody fragments. These fragments can be derived via proteolytic digestion of intact antibodies (see, e.g., Morimoto et al., 1992, J. Biochem. Biophys. Methods 24:107-117 and Brennan et al., 1985, Science 229:81), or produced directly by recombinant host cells. For example, Fab'-SH fragments can be directly recovered from *E. coli* and chemically coupled to form $F(ab')_2$ fragments (Carter et al., 1992, Bio/Technology 10:163-167). In another embodiment, the $F(ab')_2$ is formed using the leucine zipper of GCN4 to promote assembly of the $F(ab')_2$ molecule. According to another approach, Fv, Fab, or $F(ab')_2$ fragments are isolated directly from recombinant host cell culture.

In some embodiments, the antibodies of the invention are single chain (ScFv), mutants thereof, fusion proteins comprising an antibody portion, humanized antibodies, chimeric antibodies, diabodies linear antibodies, single chain antibodies, and any other modified configuration of the immunoglobulin molecule.

Single chain variable region fragments are made by linking light and/or heavy chain variable regions by using a short linking peptide. Bird et al. (1988) Science 242:423-426. An example of a linking peptide is $(GGGGS)_3$ (SEQ ID NO:29), which bridges approximately 3.5 nm between the carboxy terminus of one variable region and the amino terminus of the other variable region. Linkers of other sequences have been designed and used. Bird et al. (1988). Linkers can in turn be modified for additional functions, such as attachment of drugs or attachment to solid supports. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as *E. coli*. Polynucleotides encoding the scFv of interest can be made by routine manipulations such as ligation of polynucleotides. The resultant scFv can be isolated using standard protein purification techniques known in the art.

Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90:6444-6448; Poljak, R. J., et al. (1994) Structure 2:1121-1123).

The invention encompasses modifications to antibodies or other polypeptides described herein, including functionally equivalent antibodies which do not significantly affect their properties and variants which have enhanced or decreased activity. It is understood that the principles of modification apply to polypeptides as well as antibodies. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or use of chemical analogs.

Amino acid sequence insertions or additions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the serum half-life of the antibody.

Substitution variants have at least one amino acid residue in the antibody or other polypeptide sequence removed and a different residue inserted in its place. The sites of greatest interest for substitutional mutagenesis include the CDRs, but FR alterations are also contemplated. Conservative substitutions are shown in Table 3 under the heading of "conservative substitutions". If such substitutions result in a change in biological activity, then more substantial changes, denominated "exemplary substitutions" in Table 3, or as further described below in reference to amino acid classes, may be introduced and the products screened.

TABLE 3

| Amino Acid Substitutions | | |
|---|---|---|
| Original Residue | Conservative Substitutions | Exemplary Substitutions |
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) Hydrophobic: Norleucine, Met, Ala, Val, Leu, Ile;

(2) Neutral hydrophilic: Cys, Ser, Thr;

(3) Acidic: Asp, Glu;

(4) Basic: Asn, Gln, H is, Lys, Arg;

(5) Residues that influence chain orientation: Gly, Pro; and (6) Aromatic: Tip, Tyr, Phe.

Non-conservative substitutions are made by exchanging a member of one of these classes for another class. More conservative substitutions involve exchanging one member of a class for another member of the same class.

Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

Amino acid modifications can range from changing or modifying one or more amino acids to complete redesign of a region, such as the variable region. Changes in the variable region can alter binding affinity and/or specificity. In some embodiments, no more than one to five conservative amino acid substitutions are made within a CDR domain. In other embodiments, no more than one to three conservative amino acid substitutions are made within a CDR3 domain. In still other embodiments, the CDR domain is CDRH3 and/or CDR L3.

Modifications also include glycosylated and nonglycosylated polypeptides, as well as polypeptides with other post-translational modifications, such as, for example, glycosylation with different sugars, acetylation, and phosphorylation. Antibodies are glycosylated at conserved positions in their constant regions (Jefferis and Lund, 1997, *Chem. Immunol.* 65:111-128; Wright and Morrison, 1997, *TibTECH* 15:26-32). The oligosaccharide side chains of the immunoglobulins affect the protein's function (Boyd et al., 1996, *Mol. Immunol.* 32:1311-1318; Wittwe and Howard, 1990, *Biochem.* 29:4175-4180) and the intramolecular interaction between portions of the glycoprotein, which can affect the conformation and presented three-dimensional surface of the glycoprotein (Hefferis and Lund, supra; Wyss and Wagner, 1996, *Current Opin. Biotech.* 7:409-416). Oligosaccharides may also serve to target a given glycoprotein to certain molecules based upon specific recognition structures. Glycosylation of antibodies has also been reported to affect antibody-dependent cellular cytotoxicity (ADCC). In particular, CHO cells with tetracycline-regulated expression of β(1,4)-N-acetylglucosaminyltransferase III (GnTIII), a glycosyltransferase catalyzing formation of bisecting GlcNAc, was reported to have improved ADCC activity (Umana et al., 1999, *Nature Biotech.* 17:176-180).

Glycosylation of antibodies is typically either N-linked or O-linked. N-linked refers to the attachment of the carbohydrate moiety to the side chain of an asparagine residue. The tripeptide sequences asparagine-X-serine, asparagine-X-threonine, and asparagine-X-cysteine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

The glycosylation pattern of antibodies may also be altered without altering the underlying nucleotide sequence. Glycosylation largely depends on the host cell used to express the antibody. Since the cell type used for expression of recombinant glycoproteins, e.g. antibodies, as potential therapeutics is rarely the native cell, variations in the glycosylation pattern of the antibodies can be expected (see, e.g. Hse et al., 1997, *J. Biol. Chem.* 272:9062-9070).

In addition to the choice of host cells, factors that affect glycosylation during recombinant production of antibodies include growth mode, media formulation, culture density, oxygenation, pH, purification schemes, and the like. Various methods have been proposed to alter the glycosylation pattern achieved in a particular host organism including introducing or overexpressing certain enzymes involved in oligosaccharide production (U.S. Pat. Nos. 5,047,335; 5,510,261 and 5,278,299). Glycosylation, or certain types of glycosylation, can be enzymatically removed from the glycoprotein, for example using endoglycosidase H (Endo H). In addition, the recombinant host cell can be genetically engineered to be defective in processing certain types of polysaccharides. These and similar techniques are well known in the art.

Other methods of modification include using coupling techniques known in the art, including, but not limited to, enzymatic means, oxidative substitution and chelation. Modifications can be used, for example, for attachment of labels for immunoassay. Modified polypeptides are made using established procedures in the art and can be screened using standard assays known in the art, some of which are described below and in the Examples.

Other antibody modifications include antibodies that have been modified as described in PCT Publication No. WO 99/58572, published Nov. 18, 1999. These antibodies comprise, in addition to a binding domain directed at the target molecule, an effector domain having an amino acid sequence substantially homologous to all or part of a constant domain of a human immunoglobulin heavy chain. These antibodies are capable of binding the target molecule without triggering significant complement dependent lysis, or cell-mediated destruction of the target. In some embodiments, the effector domain is capable of specifically binding FcRn and/or FcγRIIb. These are typically based on chimeric domains derived from two or more human immunoglobulin heavy chain $C_H2$ domains. Antibodies modified in this manner are particularly suitable for use in chronic antibody therapy, to avoid inflammatory and other adverse reactions to conventional antibody therapy.

In some embodiments, the polypeptides of the invention are conjugates. For instance, in some embodiments, the polypeptide is conjugated to another agent such as a chemotherapeutic agent, a radionuclide, an immunotherapeutic agent, a cytokine, a chemokine, an imaging agent, a toxin, a biological agent, an enzyme inhibitor, or an antibody.

In some embodiments the polypeptides, such as antibodies, are conjugated to water-soluble polymer moieties. The polypeptides may be conjugated to polyethylene glycol (PEG), monomethoxy-PEG, ethylene glycol/propylene glycol copolymers, carboxymethylcellulose, dextran, polyvinyl alcohol or the like. The polypeptides may be modified at random positions with the molecule, or at predetermined positions with the molecule and may include one, two, three or more attached moieties. The polymer may be of any molecular weight, and may be branched or unbranched. In some embodiments, the moiety is attached to the polypeptide via a linker. In some embodiments, the attached moiety increases the circulating half-life of the polypeptide in an animal. Methods of attaching polymers such as PEG to polypeptides including antibodies are well known in the art. In some embodiments, the polypeptides are PEGylated polypeptides, such as PEGylated antibodies.

The invention includes affinity matured embodiments. For example, affinity matured antibodies can be produced by procedures known in the art (Marks et al., 1992, Bio/Technology, 10:779-783; Barbas et al., 1994, Proc Nat. Acad. Sci, USA 91:3809-3813; Schier et al., 1995, Gene, 169:147-155; Yelton et al., 1995, J. Immunol., 155:1994-2004; Jackson et al., 1995, J. Immunol., 154(7):3310-9; Hawkins et al, 1992, J. Mol. Biol., 226:889-896; and WO2004/058184). Candidate affinity matured antibodies may be screened or selected for improved and/or altered binding affinity using any method known in the art, including screening using BIAcore surface plasmon resonance analysis, and selection using any method known in the art for selection, including phage display, yeast display, and ribosome display.

Monoclonal antibodies may be prepared using hybridoma methods, such as those described by Kohler and Milstein, 1975, Nature 256:495. In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The monoclonal antibodies (as well as other polypeptides) of the invention may also be made by recombinant DNA methods, such as those described in U.S. Pat. No. 4,816,567. DNA encoding the monoclonal antibodies is isolated and sequenced using conventional procedures, such as by using oligonucleotide probes that are capable of binding specifically to genes encoding the heavy and light chains of the monoclonal antibodies. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells.

In some embodiments, the polypeptides of the invention (e.g., antibodies) are expressed in any organism, or cells derived from any organism, including, but not limited to bacteria, yeast, plant, insect, and mammal. Particular types of cells include, but are not limited to, *Drosophila melanogaster* cells, *Saccharomyces cerevisiae* and other yeasts, *E. coli, Bacillus subtilis*, SF9 cells, HEK-293 cells, Neurospora, BHK cells, CHO cells, COS cells, HeLa cells, fibroblasts, Schwannoma cell lines, immortalized mammalian myeloid and lymphoid cell lines, Jurkat cells, mast cells and other endocrine and exocrine cells, and neuronal cells.

A variety of protein expression systems, vectors, and cell media useful in the production of polypeptides are known to those of ordinary skill in the art. See, e.g., international patent publications WO 03/054172, WO 04/009823, and WO 03/064630, each of which is incorporated herein by reference in its entirety. In some embodiments, a glutamine synthetase (GS) expression system is used for expression of the polypeptides (e.g., antibodies).

Preferably, the polypeptide is purified or isolated after expression according to methods known to those skilled in the art. Examples of purification methods include electrophoretic, molecular, immunological, and chromatographic techniques, including ion exchange, hydrophobic affinity, and reverse-phase HPLC chromatography, and chromatofocusing. The degree of purification necessary will vary depending on the use of the polypeptide. In some instances, no purification will be necessary.

The DNA can be modified, for example, by covalently joining to the immunoglobulin coding sequence all or part of the coding sequence for a non-immunoglobulin polypeptide. In that manner, "chimeric" or "hybrid" antibodies are prepared that have the binding specificity of a monoclonal antibody disclosed herein. Typically such non-immunoglobulin polypeptides are substituted for the constant domains of an antibody of the invention, or they are substituted for the variable domains of one antigen-combining site of an antibody of the invention to create a chimeric bivalent antibody comprising one antigen-combining site having specificity for one surface epitope CD26 and another antigen-combining site having specificity for a different antigen or CD26 epitope.

The invention also encompasses humanized antibodies. Therapeutic antibodies often elicit adverse effects, in part due to triggering of an immune response directed against the administered antibody. This can result in reduced drug efficacy, depletion of cells bearing the target antigen, and an undesirable inflammatory response. To circumvent the above, recombinant anti-CD26 humanized antibodies may be generated. The general principle in humanizing an antibody involves retaining the basic sequence of the antigen-binding portion of the antibody, while swapping at least portions of the non-human remainder of the antibody with human antibody sequences. Four traditional, but non-limiting, general steps to humanize a monoclonal antibody include: (1) determining the nucleotide and predicted amino acid sequence of the starting antibody light and heavy variable domains, (2) designing the humanized antibody, i.e., deciding which antibody framework region or residues and/or CDR residues to use during the humanizing process, (3) the actual humanizing methodologies/techniques, and (4) the transfection and expression of the humanized antibody. The constant region may also be engineered to more resemble human constant regions to avoid immune response if the antibody is used in clinical trials and treatments in humans. See, for example, U.S. Pat. Nos. 5,997,867 and 5,866,692.

In the recombinant humanized antibodies, the Fcγ portion can be modified to avoid interaction with Fcγ receptor and the complement immune system. Techniques for preparation of such antibodies are described in WO 99/58572.

A number of "humanized" antibody molecules comprising an antigen-binding site derived from a non-human immunoglobulin have been described, including chimeric antibodies having rodent V regions and their associated complementarity determining regions (CDRs) fused to human constant domains. See, for example, Winter et al. *Nature* 349:293-299 (1991); Lobuglio et al. *Proc. Nat. Acad. Sci. USA* 86:4220-4224 (1989); Shaw et al. *J Immunol.* 138:4534-4538 (1987); and Brown et al. *Cancer Res.* 47:3577-3583 (1987). Other references describe rodent CDRs grafted into a human supporting framework region (FR) prior to fusion with an appropriate human antibody constant domain. See, for example, Riechmann et al. *Nature* 332:323-327 (1988); Verhoeyen et al. *Science* 239:1534-1536 (1988); and Jones et al. *Nature* 321:522-525 (1986). Another reference describes rodent CDRs supported by recombinantly veneered rodent framework regions. See, for example, European Patent Publication No. 519,596. These types of "humanized" molecules are designed to minimize unwanted immunological response toward rodent antihuman antibody molecules which limits the duration and effectiveness of therapeutic applications of those moieties in human recipients. Other methods of humanizing antibodies that may also be utilized are disclosed by Daugherty et al., *Nucl. Acids Res.,* 19:2471-2476 (1991) and in U.S. Pat. Nos. 6,180,377; 6,054,297; 5,997,867; 5,866,692; 6,210,671; 6,350,861; and PCT WO 01/27160.

Additional exemplary methods of humanizing antibodies are described in International Publication No. WO 02/084277 and U.S. Publication No. US 2004/0133357, both of which are incorporated by reference herein in their entirety.

In yet another alternative, fully human antibodies may be obtained by using commercially available mice which have been engineered to express specific human immunoglobulin proteins. Transgenic animals which are designed to produce a more desirable (e.g., fully human antibodies) or more robust immune response may also be used for generation of humanized or human antibodies. Examples of such technology are Xenomouse™ from Abgenix, Inc. (Fremont, Calif.) and HuMAb-Mouse® and TC M™ from Medarex, Inc. (Princeton, N.J.).

In another alternative, antibodies may be made recombinantly by phage display technology. See, for example, U.S. Pat. Nos. 5,565,332; 5,580,717; 5,733,743 and 6,265,150; and Winter et al., *Annu. Rev. Immunol.* 12:433-455 (1994). Alternatively, the phage display technology (McCafferty et al., *Nature* 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for review see, e.g., Johnson, Kevin S, and Chiswell, David J., *Current Opinion in Structural Biology* 3, 564-571 (1993). Several sources of V-gene segments can be used for phage display. Clackson et al., *Nature* 352:624-628 (1991), isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Mark et al., *J. Mol. Biol.* 222:581-597 (1991), or Griffith et al., *EMBO J.* 12:725-734 (1993). In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling." Marks, et al., *Bio/Technol.* 10:779-783 (1992)). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the pM-nM range. A strategy for making very large phage antibody repertoires (also known as "the mother-of-all libraries") has been described by Waterhouse et al., *Nucl. Acids Res.* 21:2265-2266 (1993). Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable regions capable of restoring a functional antigen-binding site, i.e., the epitope governs (imprints) the choice of partner. When the process is repeated in order to replace the remaining rodent V domain, a human antibody is obtained (see PCT patent application PCT WO 9306213, published Apr. 1, 1993). Unlike traditional humanization of rodent antibodies by CDR grafting, this technique provides completely human antibodies, which have no framework or CDR residues of rodent origin. It is apparent that although the above discussion pertains to humanized antibodies, the general principles discussed are applicable to customizing antibodies for use, for example, in dogs, cats, primates, equines, and bovines.

Chimeric or hybrid antibodies also may be prepared in vitro using known methods of synthetic protein chemistry, including those involving cross-linking agents. For example, immunotoxins may be constructed using a disulfide exchange reaction or by forming a thioether bond. Examples of suitable reagents for this purpose include iminothiolate and methyl-4-mercaptobutyrimidate.

Single chain Fv fragments may also be produced, such as described in Iliades et al., 1997, FEBS Letters, 409:437-441. Coupling of such single chain fragments using various linkers is described in Kortt et al., 1997, Protein Engineering, 10:423-433. A variety of techniques for the recombinant production and manipulation of antibodies are well known in the art.

In one aspect, the invention provides methods of producing the polypeptides described herein. In some embodiments, the method comprises expressing a polynucleotide in a host cell, wherein the polynucleotide encodes the polypeptide. In some embodiments, the method is a method of producing an antibody and comprises expressing one or more polynucleotides in a host cell (e.g., in cell culture), wherein each chain of the antibody is encoded by at least one of the polynucleotides. In some embodiments, the one or more polynucleotides are on the same vector. In other embodiments, the one or more polynucleotides are located on separate vectors. In some embodiments, the methods of producing polypeptides described herein further comprise the step of isolating the polypeptides from the host cells in which they are expressed (e.g., isolated from the cell culture in which the host cells are grown).

siRNA Targeting CD26 mRNA and/or CD26 cDNA

Compositions and methods comprising siRNA targeted to CD26 are advantageously used to inhibit binding of CD26 to extracellular matrix, in particular for the treatment of tumorigenesis disease. The siRNA of the invention are believed to cause the RNAi-mediated degradation of these mRNAs, so that the protein product of the CD26 genes is not produced or is produced in reduced amounts.

The invention therefore provides isolated siRNA comprising short double-stranded RNA from about 17 nucleotides to about 29 nucleotides in length, preferably from about 19 to about 25 nucleotides in length, that are targeted to the target mRNA and/or target cDNA. The siRNA comprise a sense RNA strand and a complementary antisense RNA strand annealed together by standard Watson-Crick base-pairing interactions (hereinafter “base-paired”). As is described in more detail below, the sense strand comprises a nucleic acid sequence which is identical to a target sequence contained within the target mRNA and/or target cDNA.

The sense and antisense strands of the present siRNA can comprise two complementary, single-stranded RNA molecules or can comprise a single molecule in which two complementary portions are base-paired and are covalently linked by a single-stranded “hairpin” area. Without wishing to be bound by any theory, it is believed that the hairpin area of the latter type of siRNA molecule is cleaved intracellularly by the “Dicer” protein (or its equivalent) to form an siRNA of two individual base-paired RNA molecules.

As used herein, “isolated” means altered or removed from the natural state through human intervention. For example, an siRNA naturally present in a living animal is not “isolated,” but a synthetic siRNA, or an siRNA partially or completely separated from the coexisting materials of its natural state is “isolated.” An isolated siRNA can exist in substantially purified form, or can exist in a non-native environment such as, for example, a cell into which the siRNA has been delivered.

As used herein, “target mRNA” and “target cDNA” means human CD26 mRNA and human CD26 cDNA, respectively, mutant or alternative splice forms thereof.

RT-PCR can also be used to identify alternatively spliced CD26 mRNAs. In RT-PCR, mRNA from the diseased tissue is converted into cDNA by the enzyme reverse transcriptase, using methods well-known to those of ordinary skill in the art. The entire coding sequence of the cDNA is then amplified via PCR using a forward primer located in the 3' untranslated region, and a reverse primer located in the 5' untranslated region. The amplified products can be analyzed for alternative splice forms, for example by comparing the size of the amplified products with the size of the expected product from normally spliced mRNA, e.g., by agarose gel electrophoresis. Any change in the size of the amplified product can indicate alternative splicing.

The siRNA of the invention can comprise partially purified RNA, substantially pure RNA, synthetic RNA, or recombinantly produced RNA, as well as altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA, including modifications that make the siRNA resistant to nuclease digestion.

One or both strands of the siRNA of the invention can also comprise a 3' overhang. As used herein, a “3' overhang” refers to at least one unpaired nucleotide extending from the 3'-end of an RNA strand.

Thus in one embodiment, the siRNA of the invention comprises at least one 3' overhang of from 1 to about 6 nucleotides (which includes ribonucleotides or deoxynucleotides) in length, preferably from 1 to about 5 nucleotides in length, more preferably from 1 to about 4 nucleotides in length, and particularly preferably from about 2 to about 4 nucleotides in length.

In the embodiment in which both strands of the siRNA molecule comprise a 3' overhang, the length of the overhangs can be the same or different for each strand. In a most preferred embodiment, the 3' overhang is present on both strands of the siRNA, and is 2 nucleotides in length. For example, each strand of the siRNA of the invention can comprise 3' overhangs of dithymidylic acid (“TT”) or diuridylic acid (“uu”).

In order to enhance the stability of the present siRNA, the 3' overhangs can be also stabilized against degradation. In one embodiment, the overhangs are stabilized by including purine nucleotides, such as adenosine or guanosine nucleotides. Alternatively, substitution of pyrimidine nucleotides by modified analogues, e.g., substitution of uridine nucleotides in the 3' overhangs with 2'-deoxythymidine, is tolerated and does not affect the efficiency of RNAi degradation.

In certain embodiments, the siRNA of the invention comprises the sequence AA(N19)TT or NA(N21), where N is any nucleotide. These siRNA comprise approximately 30-70% GC, and preferably comprise approximately 50% G/C. The sequence of the sense siRNA strand corresponds to (N19)TT or N21 (i.e., positions 3 to 23), respectively. In the latter case, the 3' end of the sense siRNA is converted to TT. The rationale for this sequence conversion is to generate a symmetric duplex with respect to the sequence composition of the sense and antisense strand 3' overhangs. The antisense RNA strand is then synthesized as the complement to positions 1 to 21 of the sense strand.

Because position 1 of the 23-nt sense strand in these embodiments is not recognized in a sequence-specific manner by the antisense strand, the 3'-most nucleotide residue of the antisense strand can be chosen deliberately. However, the penultimate nucleotide of the antisense strand (complementary to position 2 of the 23-nt sense strand in either embodiment) is generally complementary to the targeted sequence.

The siRNA of the invention can be targeted to any stretch of approximately 19-25 contiguous nucleotides in any of the target mRNA and/or target cDNA sequences (the “target sequence”). Techniques for selecting target sequences for siRNA are given, for example, in Tuschl T et al., "The siRNA User Guide," revised Oct. 11, 2002, the entire disclosure of which is herein incorporated by reference. "The siRNA User Guide" is available on the world wide web at a website maintained by Dr. Thomas Tuschl, Department of Cellular Biochemistry, AG 105, Max-Planck-Institute for Biophysical Chemistry, 37077 Gottingen, Germany, and can be found by accessing the website of the Max Planck Institute and searching with the keyword "siRNA." Thus, the sense strand of the present siRNA comprises a nucleotide sequence identical to any contiguous stretch of about 19 to about 25 nucleotides in the target mRNA.

Generally, a target sequence on the target mRNA can be selected from a given cDNA sequence corresponding to the target mRNA, preferably beginning 50 to 100 nt downstream (i.e., in the 3' direction) from the start codon. The target sequence can, however, be located in the 5' or 3' untranslated regions, or in the region nearby the start codon.

For example, a suitable target sequence in the CD26 cDNA sequence can be obtained from accession No. NM_001935

Thus, an siRNA of the invention targeting this sequence, and which has 3' uu overhangs on each strand (overhangs shown in bold), is:

```
                                   (SEQ ID NO: 30)
sense:          5'-GAAAGGUGUCAGUACUAUU TT-3',

                                   (SEQ ID NO: 31)
antisense:      3'-TT CUUUCCACAGUCAUGAUAA-5'
```

The siRNA of the invention can be obtained using a number of techniques known to those of skill in the art. For example, the siRNA can be chemically synthesized or recombinantly produced using methods known in the art.

Preferably, the siRNA of the invention are chemically synthesized using appropriately protected ribonucleoside phosphoramidites and a conventional DNA/RNA synthesizer. The siRNA can be synthesized as two separate, complementary RNA molecules, or as a single RNA molecule with two complementary regions. Commercial suppliers of synthetic RNA molecules or synthesis reagents include Proligo (Hamburg, Germany), Pierce Chemical (part of Perbio Science, Rockford, Ill., USA), etc.

Alternatively, siRNA can also be expressed from recombinant circular or linear DNA plasmids using any suitable promoter. Suitable promoters for expressing siRNA of the invention from a plasmid include, for example, the U6 or H1 RNA pol III promoter sequences and the cytomegalovirus promoter. Selection of other suitable promoters is within the skill in the art. The recombinant plasmids of the invention can also comprise inducible or regulatable promoters for expression of the siRNA in a particular tissue or in a particular intracellular environment.

The siRNA expressed from recombinant plasmids can either be isolated from cultured cell expression systems by standard techniques, or can be expressed intracellularly at or near the area of neovascularization in vivo. The use of recombinant plasmids to deliver siRNA of the invention to cells in vivo is discussed in more detail below.

siRNA of the invention can be expressed from a recombinant plasmid either as two separate, complementary RNA molecules, or as a single RNA molecule with two complementary regions.

Selection of plasmids suitable for expressing siRNA of the invention, methods for inserting nucleic acid sequences for expressing the siRNA into the plasmid, and methods of delivering the recombinant plasmid to the cells of interest are within the skill in the art. See, for example Tuschl, T. (2002), Nat. Biotechnol, 20: 446 448; Brummelkamp T R et al. (2002), Science 296: 550 553; Miyagishi M et al. (2002), Nat. Biotechnol. 20: 497 500; Paddison P J et al. (2002), Genes Dev. 16: 948 958; Lee N S et al. (2002), Nat. Biotechnol. 20: 500 505; and Paul C P et al. (2002), Nat. Biotechnol. 20: 505 508, the entire disclosures of which are herein incorporated by reference.

The siRNA of the invention can also be expressed from recombinant viral vectors intracellularly at or near the area of neovascularization in vivo. The recombinant viral vectors of the invention comprise sequences encoding the siRNA of the invention and any suitable promoter for expressing the siRNA sequences. Suitable promoters include, for example, the U6 or H1 RNA pol III promoter sequences and the cytomegalovirus promoter. Selection of other suitable promoters is within the skill in the art. The recombinant viral vectors of the invention can also comprise inducible or regulatable promoters for expression of the siRNA in a particular tissue or in a particular intracellular environment. The use of recombinant viral vectors to deliver siRNA of the invention to cells in vivo is discussed in more detail below.

siRNA of the invention can be expressed from a recombinant viral vector either as two separate, complementary RNA molecules, or as a single RNA molecule with two complementary regions.

Any viral vector capable of accepting the coding sequences for the siRNA molecule(s) to be expressed can be used, for example vectors derived from adenovirus (AV); adeno-associated virus (AAV); retroviruses (e.g. lentiviruses (LV), Rhabdoviruses, murine leukemia virus); herpes virus, and the like. The tropism of the viral vectors can also be modified by pseudotyping the vectors with envelope proteins or other surface antigens from other viruses. For example, an AAV vector of the invention can be pseudotyped with surface proteins from vesicular stomatitis virus (VSV), rabies, Ebola, Mokola, and the like.

Selection of recombinant viral vectors suitable for use in the invention, methods for inserting nucleic acid sequences for expressing the siRNA into the vector, and methods of delivering the viral vector to the cells of interest are within the skill in the art. See, for example, Domburg R (1995), Gene Therap. 2: 301 310; Eglitis M A (1988), Biotechniques 6: 608 614; Miller A D (1990), Hum Gene Therap. 1: 5 14; and Anderson W F (1998), Nature 392: 25 30, the entire disclosures of which are herein incorporated by reference.

The ability of an siRNA containing a given target sequence to cause RNAi-mediated degradation of the target mRNA can be evaluated using standard techniques for measuring the levels of RNA or protein in cells. For example, siRNA of the invention can be delivered to cultured cells, and the levels of target mRNA can be measured by Northern blot or dot blotting techniques, or by quantitative RT-PCR. Alternatively, the levels of CD26 protein in the cultured cells can be measured by ELISA or Western blot.

RNAi-mediated degradation of target mRNA by an siRNA containing a given target sequence can also be evaluated with animal models of neovascularization, such as the ROP or CNV mouse models. For example, areas of neovascularization in an ROP or CNV mouse can be measured before and after administration of an siRNA.

As discussed above, the siRNA of the invention target and cause the RNAi-mediated degradation of CD26 mRNA and/or CD26 cDNA, or alternative splice forms, mutants or cognates thereof. Degradation of the target mRNA by the present siRNA reduces the production of a functional gene product from the CD26 genes. Thus, the invention provides a method of inhibiting expression of CD26 in a subject, comprising administering an effective amount of an siRNA of the invention to the subject, such that the target mRNA and/or target CD26 cDNA is degraded. As the products of the CD26 genes are required for initiating and maintaining angiogenesis, the invention also provides a method of inhibiting angiogenesis in a subject by the RNAi-mediated degradation of the target mRNA and/or target CD26 cDNA by the present siRNA.

As used herein, a "subject" includes a human being or non-human animal. Preferably, the subject is a human being.

As used herein, an "effective amount" of the siRNA is an amount sufficient to cause RNAi-mediated degradation of the target mRNA, or an amount sufficient to inhibit the progression of angiogenesis in a subject.

RNAi-mediated degradation of the target mRNA and/or target CD26 cDNA can be detected by measuring levels of the target mRNA or protein in the cells of a subject, using standard techniques for isolating and quantifying mRNA and/or cDNA or protein as described above.

Inhibition of tumorigenesis can be evaluated by directly measuring the progress of pathogenic or nonpathogenic tumorigenesis in a subject; for example, by observing the size of a tumor before and after treatment with the siRNA of the invention. An inhibition of tumorigenesis is indicated if the tumor size stays the same or is reduced. Techniques for observing and measuring the tumor size in a subject are within the skill in the art.

It is understood that the siRNA of the invention can degrade the target rnRNA and/or target cDNA (and thus inhibit tumorigenesis) in substoichiometric amounts. Without wishing to be bound by any theory, it is believed that the siRNA of the invention causes degradation of the target mRNA in a catalytic manner. Thus, compared to standard anti-tumor therapies, significantly less siRNA needs to be delivered at or near the tumor site to have a therapeutic effect.

One skilled in the art can readily determine an effective amount of the siRNA of the invention to be administered to a given subject, by taking into account factors such as the size and weight of the subject; the extent of the tumorigenesis or disease penetration; the age, health, and sex of the subject; the route of administration; and whether the administration is regional or systemic. Generally, an effective amount of the siRNA of the invention comprises an intercellular concentration at or near the tumorigenesis site of from about 1 nanomolar (nM) to about 100 nM, preferably from about 2 nM to about 50 nM, more preferably from about 2.5 nM to about 10 nM. It is contemplated that greater or lesser amounts of siRNA can be administered.

The present methods can also inhibit angiogenesis which is associated with an angiogenic disease; i.e., a disease in which pathogenicity is associated with inappropriate or uncontrolled angiogenesis. For example, most cancerous solid tumors generate an adequate blood supply for themselves by inducing angiogenesis in and around the tumor site. This tumor-induced angiogenesis is often required for tumor growth, and also allows metastatic cells to enter the bloodstream.

Preferably, an siRNA of the invention is used to inhibit the growth or metastasis of solid tumors associated with malignant mesothelioma; for example breast cancer, lung cancer, head and neck cancer, brain cancer, abdominal cancer, colon cancer, colorectal cancer, esophagus cancer, gastrointestinal cancer, glioma, liver cancer, tongue cancer, neuroblastoma, osteosarcoma, ovarian cancer, pancreatic cancer, prostate cancer, retinoblastoma, Wilm's tumor, multiple myeloma; skin cancer (e.g., melanoma), lymphomas, and blood cancer.

For treating angiogenic diseases, the siRNA of the invention can administered to a subject in combination with a pharmaceutical agent which is different from the present siRNA. Alternatively, the siRNA of the invention can be administered to a subject in combination with another therapeutic method designed to treat the angiogenic disease. For example, the siRNA of the invention can be administered in combination with therapeutic methods currently employed for treating mesothelioma or preventing tumor metastasis (e.g., radiation therapy, chemotherapy, and surgery). For treating tumors, the siRNA of the invention is preferably administered to a subject in combination with radiation therapy, or in combination with chemotherapeutic agents such as cisplatin, carboplatin, cyclophosphamide, 5-fluorouracil, adriamycin, daunorubicin, or tamoxifen.

In the present methods, the present siRNA can be administered to the subject either as naked siRNA, in conjunction with a delivery reagent, or as a recombinant plasmid or viral vector which expresses the siRNA.

Suitable delivery reagents for administration in conjunction with the present siRNA include the Minis Transit TKO lipophilic reagent; lipofectin; lipofectamine; cellfectin; or polycations (e.g., polylysine), or liposomes. A preferred delivery reagent is a liposome.

Liposomes can aid in the delivery of the siRNA to a particular tissue, such as tumor tissue, and can also increase the blood half-life of the siRNA. Liposomes suitable for use in the invention are formed from standard vesicle-forming lipids, which generally include neutral or negatively charged phospholipids and a sterol, such as cholesterol. The selection of lipids is generally guided by consideration of factors such as the desired liposome size and half-life of the liposomes in the blood stream. A variety of methods are known for preparing liposomes, for example as described in Szoka et al. (1980), Ann. Rev. Biophys. Bioeng. 9: 467; and U.S. Pat. Nos. 4,235,871, 4,501,728, 4,837,028, and 5,019,369, the entire disclosures of which are herein incorporated by reference.

Preferably, the liposomes encapsulating the present siRNA comprises a ligand molecule that can target the liposome to a malignant mesothelioma cell or tissue. Ligands which bind to receptors prevalent in tumor cells, such as monoclonal antibodies that bind to CD26 are preferred.

Particularly preferably, the liposomes encapsulating the present siRNA are modified so as to avoid clearance by the mononuclear macrophage and reticuloendothelial systems, for example by having opsonization-inhibition moieties bound to the surface of the structure. In one embodiment, a liposome of the invention can comprise both opsonization-inhibition moieties and a ligand.

Opsonization-inhibiting moieties for use in preparing the liposomes of the invention are typically large hydrophilic polymers that are bound to the liposome membrane. As used herein, an opsonization inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer which significantly decreases the uptake of the liposomes by the macrophage-monocyte system ("MMS") and reticuloendothelial system ("RES"); e.g., as described in U.S. Pat. No. 4,920,016, the entire disclosure of which is herein incorporated by reference. Liposomes modified with opsonization-inhibition moieties thus remain in the circulation much longer than unmodified liposomes. For this reason, such liposomes are sometimes called "stealth" liposomes.

Stealth liposomes are known to accumulate in tissues fed by porous or "leaky" microvasculature. Thus, target tissue characterized by such microvasculature defects, for example solid tumors, will efficiently accumulate these liposomes; see Gabizon, et al. (1988), P.N.A.S., USA, 18: 6949 53. In addition, the reduced uptake by the RES lowers the toxicity of stealth liposomes by preventing significant accumulation in the liver and spleen. Thus, liposomes of the invention that are modified with opsonization-inhibition moieties can deliver the present siRNA to tumor cells.

Opsonization inhibiting moieties suitable for modifying liposomes are preferably water-soluble polymers with a molecular weight from about 500 to about 40,000 daltons, and more preferably from about 2,000 to about 20,000 daltons. Such polymers include polyethylene glycol (PEG) or polypropylene glycol (PPG) derivatives; e.g., methoxy PEG or PPG, and PEG or PPG stearate; synthetic polymers such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside $GM_1$. Copolymers of PEG, methoxy PEG, or methoxy PPG, or derivatives thereof, are also suitable. In addition, the opsonization inhibiting polymer can be a block copolymer of PEG and either a polyamino acid, polysaccharide, polyamidoamine, polyethyleneamine, or polynucleotide. The opsonization inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups.

Preferably, the opsonization-inhibiting moiety is a PEG, PPG, or derivatives thereof. Liposomes modified with PEG or PEG-derivatives are sometimes called "PEGylated liposomes."

The opsonization inhibiting moiety can be bound to the liposome membrane by any one of numerous well-known techniques. For example, an N-hydroxysuccinimide ester of PEG can be bound to a phosphatidyl-ethanolamine lipid-soluble anchor, and then bound to a membrane. Similarly, a dextran polymer can be derivatized with a stearylamine lipid-soluble anchor via reductive amination using $Na(CN)BH_3$ and a solvent mixture such as tetrahydrofuran and water in a 30:12 ratio at 60° C.

Pharmaceutical Compositions and Kits

The present invention further provides compositions comprising the polypeptides (e.g., antibodies) and/or polynucleotides described herein. For instance, the invention provides pharmaceutical compositions comprising the polypeptides described herein. Kits comprising the polypeptides are also provided.

In some embodiments, the pharmaceutical composition comprises a polypeptide described herein and a pharmaceutically acceptable excipient (also referred to herein as a "pharmaceutically acceptable carrier"). In some embodiments, the polypeptide in the pharmaceutical composition is an antibody. In some embodiments, the polypeptide in the pharmaceutical composition is a humanized antibody.

Pharmaceutical compositions within the scope of the present invention may also contain other compounds that may be biologically active or inactive.

A pharmaceutical composition can contain DNA encoding one or more of the polypeptides as described above, such that the polypeptide is generated in situ. As noted above, the DNA may be present within any of a variety of delivery systems known to those of ordinary skill in the art, including nucleic acid expression systems, bacteria, and viral expression systems. Numerous gene delivery techniques are well known in the art, such as those described by Rolland, 1998, Crit. Rev. Therap. Drug Carrier Systems 15:143-198, and references cited therein. Appropriate nucleic acid expression systems contain the necessary DNA sequences for expression in the patient (such as a suitable promoter and terminating signal).

In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., 1989, Proc. Natl. Acad. Sci. USA 86:317-321; Flexner et al., 1989, Ann. N.Y. Acad. Sci. 569:86-103; Flexner et al., 1990, Vaccine 8:17-21; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner-Biotechniques 6:616-627, 1988; Rosenfeld et al., 1991, Science 252: 431-434; Kolls et al., 1994, Proc. Natl. Acad. Sci. USA 91:215-219; Kass-Eisler et al., 1993, Proc. Natl. Acad. Sci. USA 90:11498-11502; Guzman et al., 1993, Circulation 88:2838-2848; and Guzman et al., 1993, Cir. Res. 73:1202-1207. Techniques for incorporating DNA into such expression systems are well known to those of ordinary skill in the art. The DNA may also be "naked," as described, for example, in Ulmer et al., 1993, Science 259:1745-1749, and reviewed by Cohen, 1993, Science 259:1691-1692. The uptake of naked DNA may be increased by coating the DNA onto biodegradable beads, which are efficiently transported into the cells.

While any suitable carrier known to those of ordinary skill in the art may be employed in the pharmaceutical compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous, or intramuscular administration. For parenteral administration, such as subcutaneous injection, the carrier preferably comprises water, saline, alcohol, a fat, a wax, or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

Such compositions may also comprise buffers (e.g., neutral buffered saline or phosphate buffered saline), carbohydrates (e.g., glucose, mannose, sucrose or dextran), mannitol, proteins, polypeptides or amino acids such as glycine, antioxidants, chelating agents such as EDTA or glutathione, adjuvants (e.g., aluminum hydroxide), and/or preservatives. Alternatively, compositions of the present invention may be formulated as a lyophilizate. Compounds may also be encapsulated within liposomes using well known technology.

The compositions described herein may be administered as part of a sustained release formulation (i.e., a formulation such as a capsule or sponge that effects a slow release of compound following administration). Such formulations may generally be prepared using well known technology and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated.

In some embodiments, the polypeptide also may be entrapped in microcapsules prepared, for example, by coacervation techniques or by interfacial polymerization (for example, hydroxymethylcellulose or gelatin-microcapsules and poly(methylmethacylate) microcapsules, respectively), in colloidal drug delivery systems (for example, liposomes, albumin microspheres, microemulsions, nano-particles, and nanocapsules), or in macroemulsions. Such techniques are disclosed in *Remington's Pharmaceutical Sciences,* 18th edition, A. Gennaro, ed., Mack Publishing Co., Easton, Pa., 1990; and *Remington, The Science and Practice of Pharmacy* 20th Ed. Mack Publishing, 2000. To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

The antibodies disclosed herein may also be formulated as immunoliposomes. Liposomes containing the antibody are prepared by methods known in the art, such as described in Epstein et al., 1985, Proc. Natl. Acad. Sci. USA 82:3688; Hwang et al., 1980, Proc. Natl. Acad. Sci. USA 77:4030; and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. In addition, Fab' fragments of the antibody of the present invention can be conjugated to the liposomes as described in Martin et al., 1982, J. Biol. Chem. 257:286-288, via a disulfide interchange reaction.

Kits and articles of manufacture comprising the polypeptides, polynucleotides, vectors, or host cells described herein are also provided.

In some embodiments, the article of manufacture comprises a container with a label. Suitable containers include, for example, bottles, vials, and test tubes. The containers may be formed from a variety of materials such as glass or plastic. In some embodiments, the container holds a composition useful in the identification or quantitation of cells expressing CD26, the inhibition of proliferation of cells expressing CD26, or the treatment of a disease associated with expression of CD26. In some embodiments, the label on the container indicates the composition is useful for the identification or quantitation of cells expressing CD26, the inhibition of proliferation of cells expressing CD26, or the treatment of a disease associated with expression of CD26.

In some embodiments, the kit of the invention comprises the container described above. In other embodiments, the kit of the invention comprises the container described above and a second container comprising a buffer. In some embodiments, the kit comprises a package insert with instructions for use of a polypeptide, polynucleotide, vector or host cell contained therein.

Recombinant plasmids which express siRNA of the invention are discussed above. Such recombinant plasmids can also be administered directly or in conjunction with a suitable delivery reagent, including the Minis Transit LT1 lipophilic reagent; lipofectin; lipofectamine; cellfectin; polycations (e.g., polylysine) or liposomes. Recombinant viral vectors which express siRNA of the invention are also discussed above, and methods for delivering such vectors to a tumor area in a patient are within the skill in the art.

The siRNA of the invention can be administered to the subject by any means suitable for delivering the siRNA to the cells of the tissue at or near the tumor area. For example, the siRNA can be administered by gene gun, electroporation, or by other suitable parenteral or enteral administration routes.

Suitable enteral administration routes include oral, rectal, or intranasal delivery.

Suitable parenteral administration routes include intravascular administration (e.g. intravenous bolus injection, intravenous infusion, intra-arterial bolus injection, intra-arterial infusion, and catheter instillation into the vasculature); peri- and intra-tissue injection (e.g., peri-tumoral and intra-tumoral injection, intra-retinal injection, or subretinal injection); subcutaneous injection or deposition including subcutaneous infusion (such as by osmotic pumps); direct application to the area at or near the site of neovascularization, for example by a catheter or other placement device (e.g., a suppository or an implant comprising a porous, non-porous, or gelatinous material); and inhalation. It is preferred that injections or infusions of the siRNA be given at or near the tumor site.

The siRNA of the invention can be administered in a single dose or in multiple doses. Where the administration of the siRNA of the invention is by infusion, the infusion can be a single sustained dose or can be delivered by multiple infusions. Injection of the agent directly into the tissue is at or near the tumor site. Multiple injections of the agent into the tissue at or near the tumor site are particularly preferred.

One skilled in the art can also readily determine an appropriate dosage regimen for administering the siRNA of the invention to a given subject. For example, the siRNA can be administered to the subject once, for example as a single injection or deposition at or near the tumor site. Alternatively, the siRNA can be administered once or twice daily to a subject for a period of from about three to about twenty-eight days, more preferably from about seven to about ten days. In a preferred dosage regimen, the siRNA is injected at or near the site of tumor once a day for seven days. Where a dosage regimen comprises multiple administrations, it is understood that the effective amount of siRNA administered to the subject can comprise the total amount of siRNA administered over the entire dosage regimen.

The siRNA of the invention are preferably formulated as pharmaceutical compositions prior to administering to a subject, according to techniques known in the art. Pharmaceutical compositions of the present invention are characterized as being at least sterile and pyrogen-free. As used herein, "pharmaceutical formulations" include formulations for human and veterinary use. Methods for preparing pharmaceutical compositions of the invention are within the skill in the art, for example as described in Remington's Pharmaceutical Science, 17th ed., Mack Publishing Company, Easton, Pa. (1985), the entire disclosure of which is herein incorporated by reference.

The present pharmaceutical formulations comprise an siRNA of the invention (e.g., 0.1 to 90% by weight), or a physiologically acceptable salt thereof, mixed with a physiologically acceptable carrier medium. Preferred physiologically acceptable carrier media are water, buffered water, normal saline, 0.4% saline, 0.3% glycine, hyaluronic acid, and the like.

Pharmaceutical compositions of the invention can also comprise conventional pharmaceutical excipients and/or additives. Suitable pharmaceutical excipients include stabilizers, antioxidants, osmolality adjusting agents, buffers, and pH adjusting agents. Suitable additives include physiologically biocompatible buffers (e.g., tromethamine hydrochloride), additions of chelants (such as, for example, DTPA or DTPA-bisamide) or calcium chelate complexes (as for example calcium DTPA, CaNaDTPA-bisamide), or, optionally, additions of calcium or sodium salts (for example, calcium chloride, calcium ascorbate, calcium gluconate or calcium lactate). Pharmaceutical compositions of the invention can be packaged for use in liquid form, or can be lyophilized.

For solid compositions, conventional nontoxic solid carriers can be used; for example, pharmaceutical grades of mannitol, lactose, starch, magnesium stearate, sodium saccharin, talcum, cellulose, glucose, sucrose, magnesium carbonate, and the like.

For example, a solid pharmaceutical composition for oral administration can comprise any of the carriers and excipients listed above and 10-95%, preferably 25%-75%, of one or more siRNA of the invention. A pharmaceutical composition for aerosol (inhalational) administration can comprise 0.01-20% by weight, preferably 1%-10% by weight, of one or more siRNA of the invention encapsulated in a liposome as described above, and propellant. A carrier can also be included as desired; e.g., lecithin for intranasal delivery.

Methods of Using the Polypeptides

The polypeptides (such as antibodies) of the present invention are useful in a variety of applications including, but not limited to, diagnostic methods and therapeutic treatment methods, diagnosing methods, a method of lysing malignant cell, and a method of screening a substance for treating malignant disorders. Methods of inhibiting proliferation of cells expressing CD26 are also provided.

Antibodies and polypeptides of the invention can be used in the detection, diagnosis and/or monitoring of a condition (such as a disease or disorder) associated with CD26 expression. In some embodiments, the condition associated with CD26 expression is a condition associated with abnormal CD26 expression. For instance, in some embodiments, the condition associated with CD26 expression is a condition associated with altered or aberrant CD26 expression (in some embodiments, increased or decreased CD26 expression (relative to a normal sample), and/or inappropriate expression, such as presence of expression in tissue(s) and/or cell(s) that normally lack CD26 expression, or absence of CD26 expression in tissue(s) or cell(s) that normally possess CD26 expression). In some embodiments, the condition associated with CD26 expression is a condition associated with CD26 overexpression. Overexpression of CD26 is understood to include both an increase in expression of CD26 in cell(s) or tissue(s) which normally expresses CD26 relative to the normal level of expression of CD26 in those cell(s) or tissue(s), as well as the presence of expression of CD26 in tissue(s) or cell(s) that normally lack CD26 expression. In some embodiments, the condition associated with CD26 expression is mediated, at least in part, by CD26. In some embodiments, the condition associated with CD26 expression is a condition associated with cells expressing CD26. In some embodiments, the condition associated with CD26 expression is a condition associated with the proliferation of cells expressing CD26. In some embodiments, the proliferation of the cells expressing CD26 is an abnormal proliferation. The diagnostic method may be in vitro or in vivo.

Exemplary reference is made in this discussion to antibodies, with the understanding that this discussion also pertains to the polypeptides of the invention.

For diagnostic applications, the antibody typically will be labeled with a detectable moiety including but not limited to radioisotopes, fluorescent labels, and various enzyme-substrate labels. Methods of conjugating labels to an antibody are known in the art. In other embodiment of the invention, antibodies of the invention need not be labeled, and the presence thereof can be detected using a labeled antibody which binds to the antibodies of the invention.

The antibodies of the present invention may be employed in any known assay method, such competitive binding assays, direct and indirect sandwich assays, and immunoprecipitation assays. Zola, Monoclonal Antibodies: A Manual of Techniques, pp. 147-158 (CRC Press, Inc. 1987).

The antibodies may also be used for in vivo diagnostic assays, such as in vivo imaging. Generally, the antibody is labeled with a radionuclide (such as $^{111}In$, $^{99}Tc$, $^{14}C$, $^{131}I$, $^{125}I$, or $^{3}H$) so that the cells or tissue of interest can be localized using immunoscintiography.

The antibody may also be used as staining reagent in pathology, following techniques well known in the art.

In another aspect, the invention provides a method of inhibiting proliferation of a cell expressing CD26. Inhibition of proliferation of a cell expressing CD26 encompasses any observable level of inhibition, including partial to complete inhibition of proliferation. In some embodiments, proliferation of the cells is inhibited at least about 10%, at least about 25%, at least about 50%, at least about 75%, at least about 90%, or at least about 95%, or least about 98%, or about 100%. The method may be in vitro or in vivo. In some embodiments, the method comprises contacting the cell with a polypeptide (e.g., antibody) described herein. Generally, the cell will be contacted with an amount of the polypeptide sufficient to inhibit proliferation of the cell.

In some embodiments of the aspects described herein, a cell expressing CD26 is a human cell. In some embodiments, a cell expressing CD26 is a cancer cell. In some embodiments, a cell expressing CD26 is a malignant mesothelioma, lung cancer, renal cancer, liver cancer, or other malignancies associated with CD26 expression. In some embodiments, the tumor cell is malignant or benign.

The antibody of the present invention may be used in combination with an effector cells specific to the antibody for treating, diagnosing, or inhibiting malignant mesothelioma, lung cancer, renal cancer, liver cancer, or other malignancies associated with CD26 expression.

Methods of assessing the inhibition of proliferation of a cell are known in the art and include MTT assays. (See, e.g., Aytac et al. (2003) British Journal of Cancer 88:455-462, Ho et al. (2001) Clinical Cancer Research 7:2031-2040, Hansen et al. (1989) J. Immunol. Methods, 119:203-210, and Aytac et al. (2001) Cancer Res. 61:7204-7210.) Examples of MTT assays are also provided in the specific examples Examples 2(G), 3(D), and 5 below.

The invention further provides methods for treating a condition associated with CD26 expression in a subject. In some embodiments, the method of treating a condition associated with CD26 expression in a subject, comprises administering an effective amount of a composition comprising a polypeptide, such as an antibody, described herein to the subject. In some embodiments, the condition associated with CD26 expression is associated with abnormal expression of CD26. In some embodiments, the condition associated with CD26 expression is a condition associated with altered or aberrant CD26 expression (in some embodiments, increased or decreased CD26 expression (relative to a normal sample), and/or inappropriate expression, such as presence of expression in tissue(s) and/or cell(s) that normally lack CD26 expression, or absence of CD26 expression in tissue(s) or cell(s) that normally possess CD26 expression). In some embodiments, the condition associated with CD26 expression is a condition associated with CD26 overexpression. In some embodiments, the condition associated with CD26 expression is mediated, at least in part, by CD26. In some embodiments, the condition associated with CD26 expression is a condition associated with cells expressing CD26. In some embodiments, the condition associated with CD26 expression is a condition associated with the proliferation of cells expressing CD26. In some embodiments, the proliferation of CD26-expressing cells is abnormal. In some embodiments, the cell expressing CD26 is a T-cell. In some embodiments, the cell expressing CD26 is a tumor cell, which may be malignant or benign. (Additional cells expressing CD26 are described above.)

In some embodiments, the condition associated with CD26 expression in a subject is a proliferative disorder. In some embodiments, the condition associated with CD26 expression in a subject is a cancer. In some embodiments, the cancer is a malignant mesothelium, lung cancer, renal cancer, liver cancer, or other malignancies associated with CD26 expression.

The methods described herein (including therapeutic methods) can be accomplished by a single direct injection at a single time point or multiple time points to a single or multiple sites. Administration can also be nearly simultaneous to multiple sites. Frequency of administration may be determined and adjusted over the course of therapy, and is based on accomplishing desired results. In some cases, sustained continuous release formulations of polypeptides (including antibodies), polynucleotides, and pharmaceutical compositions of the invention may be appropriate. Various formulations and devices for achieving sustained release are known in the art.

Patients, subjects, or individuals include mammals, such as human, bovine, equine, canine, feline, porcine, and ovine animals. The subject is preferably a human, and may or may not be afflicted with disease or presently show symptoms.

The antibody is preferably administered to the mammal in a carrier; preferably a pharmaceutically-acceptable carrier. Suitable carriers and their formulations are described in *Remington's Pharmaceutical Sciences,* 18th edition, A. Gennaro, ed., Mack Publishing Co., Easton, Pa., 1990; and *Remington, The Science and Practice of Pharmacy* 20th Ed. Mack Publishing, 2000. Typically, an appropriate amount of a pharmaceutically-acceptable salt is used in the formulation to render the formulation isotonic. Examples of the carrier include saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of antibody being administered.

The antibody can be administered to the mammal by injection (e.g., systemic, intravenous, intraperitoneal, subcutaneous, intramuscular, intraportal), or by other methods, such as infusion, which ensure its delivery to the bloodstream in an effective form. The antibody may also be administered by isolated perfusion techniques, such as isolated tissue perfusion, to exert local therapeutic effects. Intravenous injection is preferred.

Effective dosages and schedules for administering the polypeptide (e.g., antibody) may be determined empirically, and making such determinations is within the skill in the art. Those skilled in the art will understand that the dosage of antibody that must be administered will vary depending on, for example, the mammal that will receive the antibody, the route of administration, the particular type of antibody used, and other drugs being administered to the mammal. Guidance in selecting appropriate doses for antibody is found in the literature on therapeutic uses of antibodies, e.g., *Handbook of Monoclonal Antibodies*, Ferrone et al., eds., Noges Publications, Park Ridge, N.J., 1985, ch. 22 and pp. 303-357; Smith et al., *Antibodies in Human Diagnosis and Therapy*, Haber et al., eds., Raven Press, New York, 1977, pp. 365-389. A typical daily dosage of the antibody used alone might range from about 1 μg/kg to up to 100 mg/kg of body weight or more per day, depending on the factors mentioned above. Generally, any of the following doses may be used: a dose of at least about 50 mg/kg body weight; at least about 10 mg/kg body weight; at least about 3 mg/kg body weight; at least about 1 mg/kg body weight; at least about 750 μg/kg body weight; at least about 500 μg/kg body weight; at least about 250 μg/kg body weight; at least about 100 μg/kg body weight; at least about 50 μg/kg body weight; at least about 10 μg/kg body weight; at least about 1 μg/kg body weight, or more, is administered.

In some embodiments, more than one antibody may be present. Such compositions may contain at least one, at least two, at least three, at least four, or at least five different antibodies (including polypeptides) of the invention.

The polypeptide may also be administered to the mammal in combination with effective amounts of one or more other therapeutic agents. The polypeptide may be administered sequentially or concurrently with the one or more other therapeutic agents. The amounts of polypeptide and therapeutic agent depend, for example, on what type of drugs are used, the pathological condition being treated, and the scheduling and routes of administration but would generally be less than if each were used individually.

Following administration of antibody to the mammal, the mammal's physiological condition can be monitored in various ways well known to the skilled practitioner.

The above principles of administration and dosage can be adapted for polypeptides described herein.

A polynucleotide encoding a polypeptide (including an antibody) of the invention may also be used for delivery and expression of the antibody or the polypeptide in a desired cell. It is apparent that an expression vector can be used to direct expression of the antibody. The expression vector can be administered systemically, intraperitoneally, intravenously, intramuscularly, subcutaneously, intrathecally, intraventricularly, orally, enterally, parenterally, intranasally, dermally, or by inhalation. For example, administration of expression vectors includes local or systemic administration, including injection, oral administration, particle gun or catheterized administration, and topical administration. One skilled in the art is familiar with administration of expression vectors to obtain expression of an exogenous protein in vivo. See, e.g., U.S. Pat. Nos. 6,436,908; 6,413,942; and 6,376,471.

Targeted delivery of therapeutic compositions comprising a polynucleotide encoding a polypeptide or antibody of the invention can also be used. Receptor-mediated DNA delivery techniques are described in, for example, Findeis et al., *Trends Biotechnol.* (1993) 11:202; Chiou et al., *Gene Therapeutics: Methods And Applications Of Direct Gene Transfer* (J. A. Wolff, ed.) (1994); Wu et al., *J. Biol. Chem.* (1988) 263:621; Wu et al., *J. Biol. Chem.* (1994) 269:542; Zenke et al., *Proc. Natl. Acad. Sci.* (USA) (1990) 87:3655; Wu et al., *J. Biol. Chem.* (1991) 266:338. Therapeutic compositions containing a polynucleotide are administered in a range of about 100 ng to about 200 mg of DNA for local administration in a gene therapy protocol. Concentration ranges of about 500 ng to about 50 mg, about 1 μg to about 2 mg, about 5 μg to about 500 μg, and about 20 μg to about 100 μg of DNA can also be used during a gene therapy protocol. The therapeutic polynucleotides and polypeptides of the present invention can be delivered using gene delivery vehicles. The gene delivery vehicle can be of viral or non-viral origin (see generally, Jolly, *Cancer Gene Therapy* (1994) 1:51; Kimura, *Human Gene Therapy* (1994) 5:845; Connelly, *Human Gene Therapy* (1995) 1:185; and Kaplitt, *Nature Genetics* (1994) 6:148). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740; 4,777,127; GB Patent No. 2,200,651; and EP 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, *Hum. Gene Ther.* (1992) 3:147 can also be employed.

Non-viral delivery vehicles and methods can also be employed, including, but not limited to, polycationic condensed DNA linked or unlinked to killed adenovirus alone (see, e.g., Curiel, *Hum. Gene Ther* (1992) 3:147); ligand-linked DNA(see, e.g., Wu, *J. Biol. Chem.* (1989) 264:16985); eukaryotic cell delivery vehicles cells (see, e.g., U.S. Pat. No. 5,814,482; PCT Publication Nos. WO 95/07994; WO 96/17072; WO 95/30763; and WO 97/42338), and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP 0 524 968. Additional approaches are described in Philip, *Mol. Cell. Biol.* (1994) 14:2411, and in Woffendin, *Proc. Natl. Acad. Sci.* (1994) 91:1581.

The invention will now be illustrated with the following non-limiting examples.

Examples

Materials and Methods

Reagents and Antibodies

Anti-CD26 mouse mAb (IgG1)14D10, 5F8, and anti-CD45 RA mouse mAb (IgG1) 2H4 were developed in our laboratory as described previously (20, 21), with the last one being used as control. Normal human IgG (Sigma Aldrich, St. Louis, Mo.) was also used as a control. Humanized anti-CD26 mAb was generated from 14D10 coding sequence. In brief, several Fab clones which posses high binding affinity to the epitope were selected. They were tested for biological efficacies using in vitro proliferation assay. One was selected for generation of a humanized anti-CD26 mAb (humAb). Mouse mAb to PKBα/Akt, CDK2, CDK4, CDK6, cyclinE, and β-actin were from Cell Signaling Technology Inc. (Beverly, Mass.), and mouse mAb to $p27^{kip1}$, $p21^{cip1/waf1}$, cyclinD1, and activated caspase 3 were from BD PharMingen™ (Lexington, Ky.). Anti-human IgG, Fcγ fragment specific $F(ab')_2$ fragment of goat, anti-mouse IgG, and Fcγ fragment specific F(ab')2 fragment of goat were from Jackson ImmunoResearch (West Grove, Pa.).

Cell Culture and Transfection

JMN cells were a kind gift from Dr. Brenda Gerwin (Laboratory of Human Carcinogenesis, National Institutes of Health, Bethesda, Md.). NCI-H2452 cells and 293T cells were obtained from the American Type Culture Collection (Rockville, Md.). JMN cell line and NCI-H2452 cell line were derived from patients with malignant mesothelioma. All cells were grown in RPMI medium (Life Technologies Inc., Grand Island, N.Y.) supplemented with 10% heat-inactivated fetal bovine serum (FBS), penicillin (100 units/ml), and streptomycin (100 μg/ml) (Life Technologies Inc., Gaithersburg, Md.), or G418 (500 μg/ml) (Sigma-Aldrich, St. Louis, Mo.). 293T cells were transfected with full length CD26 subcloned into a pEB6 vector (22) using FuGENE6 reagent (Roche Diagnostics, Indianapolis, Ind.). pEB6 vector was a kind gift from Dr Y. Miwa (University of Tsukuba, Ibaraki, Japan).

2-(2-methoxy-4-nitrophenyl)-3-(4-nitrophenyl)-5-(2,4-disulfophenyl)-2H-tetrazolium assay Cells were incubated in 96-well plates in media alone or in the presence of humAb (0.1, 1.0, or 10 μg/ml), or 2H4 (0.1, 1.0, or 10 μg/ml) in a total volume of 1004 ($5\times10^3$ cells per well). After 24 h of incubation in 37° C., 2-(2-methoxy-4-nitrophenyl)-3-(4-nitrophenyl)-5-(2,4-disulfophenyl)-2H-tetrazolium (Seikagaku, Tokyo, Japan) was added to each well. After another 2 h of incubation, water soluble formazan dye upon bioreduction in the presence of an electron carrier, 1-methoxy-5-methylphenazinium, was measured at 450 nm using a microplate reader (BioRad, Hercules, Calif.). All samples were tested in triplicate. Values reported represent the means of triplicate wells, and the standard error (SE) of mean was within 15.

Immunohistochemistry

For immunohistochemistry, surgical specimens from twelve patients consisting of seven MM, three reactive mesothelial cells, and two adenomatoid tumors were evaluated. For each, 10% formalin-fixed, paraffin-embedded specimens containing both the carcinoma and its adjacent non-neoplastic tissue were prepared. Paraffin-embedded tissue were dewaxed and rehydrated using xylene and ethanol, respectively. Slides were deparaffinized, then heated in a microwave processor for antigen retrieval in 10 mM citrate buffer (pH 6.0) for 10 min. After blocking in 3% (vol/vol) BSA, slides were incubated at 4° C. overnight with the primary antibody (anti-CD26 mAb), washed with PBS, and the secondary antibody was labeled with biotin and applied for 30 min. Streptavidin-LSA amplification method was carried out for 30 min followed by peroxidase/diaminobenzidine substrate/chromagen. The slides were counterstained with hematoxylin. Two different pathologists checked the validity of the obtained results. All human specimens were obtained from Department of Pathology, Keio University (Tokyo, Japan), and informed consent was obtained from all patients in accordance with requirements of the institutional review board (IRB).

Depletion of Endogenous CD26

To deplete endogenous CD26, siRNA-oligo targeting CD26 cDNA (accession no. NM_001935) was made according to the design site of TAKARA BIO (http://www.takara-bio.co.jp/RNAi.htm); sense: 5'-GAAAGGUGUCAGUAC-UAUU TT-3' (SEQ ID NO: 30), antisense: 3'-TT CUUUCCACAGUCAUGAUAA-5' (SEQ ID NO: 31), with scrambled control siRNA-oligo targeting human Cas-L; sense: 5'-UAAUUAGGGUCGGGUAAAC TT-3' (SEQ ID NO: 32), antisense: 3'-TT AUUAAUCCCAGCCCAUUUG-5' (SEQ ID NO: 33), being used as control. CD26 siRNA oligo (siCD26) was transfected using TransIT-TKO® transfection reagent (Minis Bio Corporation, Madison, Wis.) according to the manufacturer's protocol.

SDS-PAGE and Immuno-Blotting

Preparation of whole cell lysates and cell fractionations were performed as described elsewhere (23). The protein samples were subjected to SDS-PAGE and transferred to polyvinylidene difluoride membrane (Immobilon-P; Millipore, Bedford, Mass.). Specific antigens were probed using the corresponding mAbs, followed by HRP-conjugated secondary Ig (Amersham Pharmacia Biotech, Piscataway, N.J.). Western blots were visualized by the enhanced chemiluminescence technique (NEN, Boston, Mass.).

Antibody-Dependent Cell-Mediated Cytotoxicity (ADCC)

The capacity of mAb to induce effector cell-dependent lysis of tumor cells was evaluated with the Calcein-AM-release assay. Healthy donor NK cells were isolated from PBMCs with the NK Cell Isolation Kit II Miltenyi Biotec (Bergisch Gladbach, Germany), and used as effector cells. Target cells ($1\times10^6$ cells) were labeled with 10 μM Calcein-AM (Dojindo, Kumamoto, Japan) under shaking conditions at 37° C. for 1 h. Cells were washed three times with PBS and resuspended in culture medium ($1\times10^5$ cells/ml). Labeled cells were dispensed in 96-well U-bottom plates ($5\times10^3$, in 50 μl/well) and preincubated (37° C., 30 min) with 50 μl of 7-fold serial dilutions of humAb or 14D10, in culture medium, ranging from 0.1 pg/ml to 0.1 mg/ml (final concentrations). Culture medium was added instead of mAb to determine spontaneous Calcein-AM release, with Triton X-100 (1% final concentration) being added to determine maximal Calcein-AM release. Thereafter, human effector cells were added to the wells ($5\times10^5$ cells/well) and cells were incubated at 37° C. overnight. Supernatants were then collected for measurement of the Calcein-AM release. Percentage of specific lysis was calculated using the following formula: % specific lysis=(experimental release−spontaneous release)/(maximal release spontaneous release)×100; where maximal release was determined by adding Triton X-100 to target cells, and spontaneous release was measured in the absence of sensitizing Abs and effector cells.

Complement-Dependent Cytotoxicity (CDC)

CDC assay was performed as described previously (24). Target cells were dispensed in 96-well U-bottom plates at $1\times10^5$ cells/well, and incubated with various concentrations of mAbs at 4° C. for 30 min. Subsequently, human serum was added and cells were incubated at 37° C. for 2 h. Evaluation of CDC specific cell death along with ADCC specific cell death was assessed with the Annexin V-F1TC Apoptosis Detection Kit (BioVision, Mountain View, Calif.) and detection of activated caspase 3.

Assessment of Antitumor Activity of Humanized Anti-CD26 mAb in Effector-Depleted SCID Mice All in vivo studies were approved by the Institute Animal Care and Use Committee. 6 week old female NOD-SCID mice were purchased from Charles River (Kanagawa, Japan), and were pre-treated with anti-asialo-GM1 polyclonal antisera 25% (v/v, WAKO, Osaka, Japan) i.p. 1 day before mAb treatment.

To assess the effect of humAb against tumorigenicity, JMN cells ($1\times10^6$) were inoculated subcutaneously into the left flank of mice. Mice were treated with intratumoral injection of isotype matched control mAb, 5F8, 14D10, or humanized anti-CD26 mAb (10 μg/each injection) on the $14^{th}$ day after cancer cell inoculation when the tumor mass became visible (5 mm in size). Each mAb was administered three times per week. Tumor-bearing mice were then monitored for tumor development and progression. Tumor size was determined by caliper measurement of the largest (x) and smallest (y) perpendicular diameters, and was calculated according to the formula $V=\pi/6\times xy^2$.

To assess the effect of humAb against tumor dissemination, JMN cells ($1\times10^5$) were injected intravenously via tail vein. Thereafter, mice were treated with intra-venous injection of isotype matched control mAb, 5F8, 14D10, or humanized anti-CD26 mAb (10 μg/each injection), starting on the day of cancer cell injection. Each mAb was administered three times per week. Cumulative proportion survival was assessed by Kaplan-Meier.

Assessment of Antitumor Activity of Humanized Anti-CD26 mAb in Effector-Present Balb Mice 6 week old female Balb mice were purchased from Charles River (Kanagawa, Japan), and treatment with anti-asialo-GM1 polyclonal antisera was not introduced to preserve the binding of the mouse effector system.

To assess the effect of humAb against tumorigenicity, JMN cells ($1\times10^6$) were inoculated subcutaneously into the left flank of mice. Mice were treated with intratumoral injection of isotype matched control mAb, 5F8, 14D10, or humanized anti-CD26 mAb (10 μg/each injection) on the 14th day after cancer cell inoculation when the tumor mass became visible (5 mm in size). Each mAb was administered three times per week. Tumor-bearing mice were then monitored for tumor development and progression. Tumor size was determined by caliper measurement of the largest (x) and smallest (y) perpendicular diameters, and was calculated according to the formula $V=\pi/6\times xy^2$. On the 35th day after the first mAb treatment, all mice were euthanized to assess the microscopic feature of resected specimens in subcutaneous tumorigenicity model.

To assess the effect of humAb against tumor dissemination, JMN cells ($1\times10^5$) were intravenously injected via tail vein. Thereafter, mice were treated with intra-venous injection of isotype matched control mAb, or humanized anti-CD26 mAb (10 μs/each injection) starting on the day of cancer cell injection. Each mAb was administered three times per week. Cumulative proportion of survival was assessed by Kaplan-Meier. To further assess the effect of humanized anti-CD26 in Ab on distant metastasis formation, treated mice were euthanized and multiple metastasis formation in the lung and liver was calculated in another tumor dissemination model. JMN cells ($1\times10^5$) were injected intravenously into mice in each group. Mice were treated with intra-venous injection of isotype matched control mAb (lane 1, n=4), 5F8 (lane 2, n=4), 14D10 (lane 3, n=4), or humanized anti-CD26 mAb (lane 4, n=4) on the day of cancer cell injection. Each mAb was administered three times per week. On the 35th day after cancer cell injection, mice were euthanized and multiple metastasis formation in the lung and liver was calculated.

Construction of Human Effector Cell (HuEC)-Engrafted Mice and Assessment Of Antitumor Activity in NOD/Shi-scid, IL-R$\gamma^{null}$ Mice NOD/Shi-scid, IL-R$\gamma^{null}$ (NOG mice) were obtained from Central Institute for Experimental Animals (CIEA) (Kanagawa, Japan). Human PBMCs were isolated from the peripheral blood of a healthy donor using Lymphoprep (AXIS-SHIELD, Oslo, Norway) and used as HuEC. Thereafter, HuEC ($5\times10^6$) were injected intraperitoneally (i.p.) in a volume of 0.2 ml suspended in PBS into NOG-SCID mice under sterile conditions. The mice were pretreated with a 0.2 mL anti-asialo-GM1 polyclonal antisera 25% (v/v, WAKO, Osaka, Japan) given i.p. 1 day before HuEC injection. NCI-H2452 cells ($5\times10^4$) were injected i.p. into SCID mice engrafted with human HuEC, 1 days after HuEC injection. One, 3, and 5 days later, humAb were injected i.p. Mice were observed daily to monitor for death due to ascites tumor development. Cumulative proportion of survival was assessed by Kaplan-Meier.

Results

Cell Surface CD26 is Highly Expressed on Human MM Tissue.

Figure 1A:
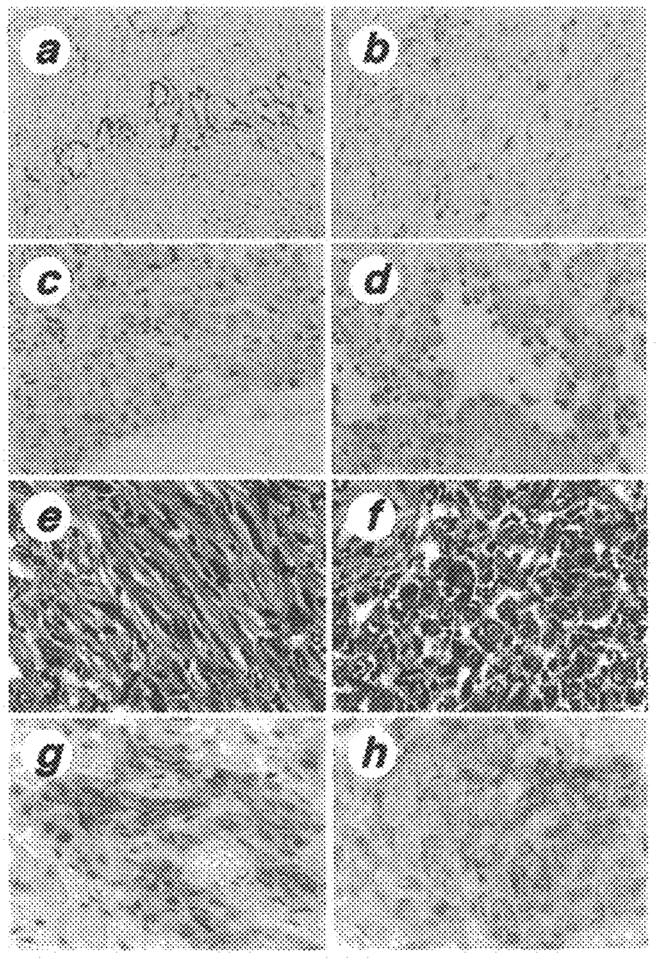
FIG. 1A. Expression and functional role of CD26 in MM.

We first evaluated the level of CD26 expression on surgically resected human MM tissues from patients. Twelve consecutive surgically resected specimens from the primary sites were examined for cell surface CD26 expression. CD26 was highly expressed on all MM tissues (FIG. 1A). In adenomatoid tumor, or reactive mesothelial cells, CD26 expression was very weak (FIG. 1A-a,b). In contrast, CD26 was highly expressed in various pathological types of MM, including localized MM, well-differentiated papillary MM, and diffuse MM (FIG. 1A-*c* to h). These results suggested that CD26 is highly expressed in MM, but not in benign mesothelial tissues.

CD26 Plays a Role in Cell Adhesion to Extracellular Matrix.

MM cell lines, JMN and NCI-H2452, exhibited high levels of surface CD26 expression (FIG. 1B).

Since CD26 has been described previously to play a role in cell adhesion to extracellular matrix (ECM) proteins (13, 25), we examined whether CD26 plays a role in cellular interaction with the ECM. As seen in FIG. 1C, NCI-H2452 depleted of endogenous CD26 using siRNA oligo showed significant loss of CD26 binding to extracellular matrix proteins including fibronectin and collagen I. In contrast to these results, depletion of CD26 did not alter binding to laminin (an ECM protein lacking binding ability to CD26), or hyaluronan (a ligand for CD44) (FIG. 1C). In further support of these findings, 293T cells transfected with full length CD26 cDNA subcloned into pEB6 vector showed higher binding ability to fibronectin and collagen I than control pEB6 transfected 293T cells (FIG. 1C). Moreover, depletion of CD26 was associated with the upregulation of p27$^{kip1}$ (FIG. 1D). These findings thus suggested that CD26 serves as a binding molecule to distinct ECM proteins and that contact inhibition may play a contributing role to the observed CD26-depletion-mediated upregulation of p27$^{kip1}$ associated with CD26 depletion (26, 27).

Anti-CD26 mAb Perturbs Cellular Binding to ECM.

Since CD26 proved to be an ECM binding protein, we further evaluated whether anti-CD26 mAbs disrupt cellular adhesion to ECM. For this purpose, isotype matched control mAb, 5F8, 14D10, and humanized anti-CD26 mAb (humAb) were evaluated for potential disruption to cellular adhesion to ECM. As seen in FIG. 2A, JMN cells treated with 14D10 and humAb had decreased binding to fibronectin and collagen I, while control mAb and 5F8 (anti-CD26 mAb without biological function) did not influence binding to fibronectin and collagen I. Moreover, 14D10 and humAb conferred direct growth inhibition to JMN cells by in vitro proliferation assay in a dose dependent manner, with humAb having a stronger antiproliferative effect than 14D10 (FIG. 2B). Importantly, 14D10 and humAb induced upregulation of p27$^{kip1}$ and downregulation of CDK2. These results suggested that both 14010 and humAb dynamically confer contact inhibition-related growth inhibition via upregulation of p27$^{kip1}$ and downregulation of CDK2.

Humanization of Anti-CD26 mAb Results in Antibody-Dependent Cell-Mediated Cytotoxicity.

While both 14D10 and humAb had similar direct effects on cancer cells, our present studies revealed different biological effects of humAb as compared to 14D10, through the use of ADCC assay with human effector cells. When effector/target (E/T) ratio was held constant at 50, JMN cells treated with humAb showed specific lysis via ADCC in an antibody-dose dependent manner (FIG. 3A, left panel). Importantly, JMN cells treated with 14D10 did not show ADCC specific lysis (FIG. 3A, left panel), suggesting that humanization of 14D10 to humAb results in the induction of potent ADCC activity via engagement of the human effector system. Moreover, as seen in FIG. 3A, right panel, humAb provoked ADCC specific lysis in an effector-dose dependent manner. These results were also observed when other CD26-positive MM lines besides JMN (NCI-H2452) were used as target cells. These data suggested that humAb possesses a novel biological function other than the direct effect on target cells seen with 14010, namely ADCC specific lysis. To better characterize the humAb-mediated ADCC, apoptosis assays using PI-annexinV staining and detection of cleaved caspase 3 were employed. In these assays, a cross-linking method using anti-human IgG, Fcγ fragment specific F(ab')2 fragment of goat, anti-mouse IgG, and Fcγ fragment specific F(ab')2 fragment of goat were used to mimic human effectors to humAb and 14D10, respectively. As seen FIG. 3B, upper three panels, cross-linked humAb induced late apoptosis, while cross-linked 14D10 did not induce late or early apoptosis. Importantly, neither humAb nor 14D10 induced CDC using human complement (FIG. 3B, lower three panels; Supplementary FIG. 1). To further support these findings, only cross-linked humAb induced activation of caspase 3 in JMN cells, while cross-linked 14D10, humAb plus human complement, and 14D10 plus human complement did not (FIG. 3C). These results therefore indicated that humAb elicits ADCC specific lysis, but not CDC specific lysis.

Humanized Anti-CD26 mAb Exhibits a Direct In Vivo Anti-Tumor Effect on MM Cells.

Since we recently demonstrated that 14D10 exhibits direct in vivo anti-tumor effect on solid tumors (24), we further examined whether humAb has a similar in vivo anti-tumor effect. For this purpose, we utilized NOD-SCID mice, which lack functional B and T cells as well as most natural killer (NK) cell activity (28). To minimize the effect of mouse effector cells, NOD-SCID mice were pre-treated by anti-asialo-GM1 polyclonal antisera, prior to being subjected to humAb functional evaluation. As seen in FIGS. 4A and B, humAb and 14D10 reduced the tumorigenicity of subcutaneously inoculated JMN, with humAb being more potent in reducing tumor formation. These observed results suggested that humAb possesses a stronger direct anti-tumor effect than 14D10. To further examine the direct anti-tumor activity of humAb on tumor dissemination, we examined the effect of intravenously administered antibodies in a JMN xenograft model. As seen in FIG. 4C, humAb and 14D10 enhanced mouse survival when both antibodies were administered intravenously, with humAb being more efficient in promoting survival. All together, these observed results suggested that humAb is more potent than 14D10 in its direct anti-tumor activity.

Mouse Effector System May Potentiate the Anti-Tumor Effect of Anti-CD26 mAb.

While both humAb and 14D10 showed a direct in vivo anti-tumor effect, we next examined the potential involvement of mouse effector system in the anti-CD26 mAb activity induced anti-tumor effect. For this purpose, we utilized Balb mice, which possesses robust NK cell activity. As seen in FIG. 5A, humAb and 14D10 reduced the tumorigenicity of subcutaneously inoculated JMN. It should be noted that both 14D10 and humAb reduced tumor formation in the presence of the mouse effector system (FIG. 5A). As seen in FIG. 5B, both humAb and 14D10-treated tumors showed resultant dead tissues upon microscopic analyses. These results suggested that both humAb and 14D10 utilized the mouse effector system, in marked contrast to the observed differences between humAb and 14D10 in the mouse effector-depleted xenograft model. Additional studies using intravenous administration of JMN cells showed that intravenous injection of humAb effectively enhanced mouse survival in the presence of the mouse effector system (FIG. 5C). Importantly, formation of distant JMN was similarly inhibited by both humAb and 14D10 (FIG. 5D). These data indicated that the mouse effector system potentiates the anti-CD26 mAb-mediated direct anti-tumor effect.

Human Effector System May Potentiate Anti-Tumor Effect of Humanized Anti-CD26 mAb.

We next evaluated the potential involvement of human effector system in the anti-CD26 mAb-induced anti-tumor effect. For this purpose, NOD/Shi-scid, IL-R$\gamma^{null}$ (NOG mice) which have significant defects in T, B, and NK cell activity, were employed in a NCI-H2452 xenograft model construction. Human PBMCs were used as human effector cells (HuEC) in this in vivo model. To completely deplete the mouse effector system, NOG mice were pretreated with anti-asialo-GM1 antisera one day prior to intraperitoneal HuEC implantation. As seen in FIG. 6, intraperitoneal administration of humAb drastically enhanced NCI-H2452 xenograft mouse survival in the absence of HuEC. It should be noted that while 14D10 also enhanced mouse survival, its effect was much weaker than humAb in the absence of HuEC (FIG. 6). These results suggested that humAb possesses a stronger direct anti-tumor effect. Importantly, in the presence of HuEC, the anti-tumor effect of humAb was exaggerated, while the anti-tumor effect of 14D10 was not altered significantly (FIG. 6). All together these observed results suggested that CD26 is an appropriate molecular target for mesothelioma therapy and humAb regulates tumor growth by at least two distinct mechanisms of action, through its direct anti-tumor activity as well as its ability to engaze human effector system.

Discussion

In this study, we demonstrate the anti-tumor effect of anti-CD26 mAb in an in vitro and in vivo model. Importantly, our study suggests that humanization of anti-CD26 mAb yields additive anti-tumor effect to contact inhibition associated with p27$^{kip1}$ induction. Our study also indicates the functional role of CD26 as a binding protein to ECM in human MM.

Immunohistological analysis indicated that human MM cells express high levels of surface CD26 than non-malignant tissue, suggesting that CD26 may play a role in cancer growth and progression. It should be noted that depletion of endogenous CD26 in NCI-H2452 using siRNA oligo results in significant loss of binding to ECM, including fibronectin and collagen I. Moreover, 293T cells transfected with full length CD26 cDNA exhibit higher binding affinity to fibronectin and collagen I than control mock transfected 293T cells. Moreover, depletion of CD26 leads to the upregulation of p27$^{kip1}$. These findings thus suggest that CD26 is involved in cancer cell adhesion to ECM and that contact inhibition may play a contributing role to the observed CD26-depletion-mediated upregulation of p27$^{kip1}$. It has been previously reported that p27$^{kip1}$ is up-regulated during contact inhibition (26).

Both humAb and 14D10 display direct inhibition of MM growth via p27$^{kip1}$ upregulation and disruption of binding to ECM. Hence, our results with these anti-CD26 monoclonal antibodies are consistant with those obtained from above siRNA study, showing that both humAb and 14D10 have an antagonistic effect on the adhesive property of MM.

Further examination of their effector functions associated with anti-CD26 mAb mediated anti-tumor effect indicates that humAb, but not 14D10, elicits ADCC induced cell lysis. Cross-linking of humAb results in an accumulation of annexinV-positive and PI-positive population, and cleavage of activated caspase 3. These data suggest that humanization of anti-CD26 mAb elicits greater contribution from ADCC in addition to a direct anti-tumor effect. Meanwhile, the reason why humAb does not induce CDC activity is not clear at the moment. One potential reason is the high surface expression of DAF and CD59, which are antagonistic to human complement proteins (data not shown). Alternatively, our in vitro system may not be appropriate for the induction of CDC activation.

In vivo study with NOD-SCID mice showed that humAb and 14D10 reduce the tumorigenicity of subcutaneously inoculated JMN cells, suggesting that humAb possesses a direct anti-tumor effect as well. Our results also suggest that humAb is more potent in reducing tumor formation, possibly due to its higher binding affinity to CD26 than 14D10.

Meanwhile, in vivo study with Balb mice showed that humAb and 14D10 are equally effective in reducing the tumorigenicity of subcutaneously inoculated JMN cells. These data suggest that the mouse effector system may potentiate the anti-tumor effect of 14D10 more than humAb. In fact, not only humAb but also 14D10-treated tumor specimens from these mice exhibit a reduction of viable cells in tumor mass. It is also noteworthy that both humAb and 14D10 reduce the formation of distant metastasis, findings which may be partly explained by our in vitro results that CD26 serves as a binding protein to distinct ECM proteins.

In vivo study with NOG-SCID mice which lack functional mice effectors showed that dual-xenograft of human effector cells plus target cells results in greater mouse survival than single xenograft of target when combined with humAb. These data clearly corroborate the in vitro data suggesting that humAb induces a biphasic anti-tumor action with a human effector system.

CD26 status may be altered in cancer and may have an effect on the growth and metastatic potential of various tumors. CD26 absence is associated with the development of some cancers while CD26 presence is associated with a more aggressive phenotype in other neoplasms. For example, in non small cell lung cancer cell lines, cells transfected with CD26 develop morphologic changes, altered contact inhibition, and reduced ability for anchorage-independent growth (29). CD26 reexpression also correlates with increased p21 expression, leading to induction of apoptosis and cell cycle arrest in G1 stage. Wesley et al reported that CD26/DPPIV up-regulates the expression of CDKI $p27^{kip1}$ by 4 to 6 fold in CD26 transfected DU-145 metastatic prostate cancer cells compared with the parent and vector transfected DU-145 cells (30). It is also reported that overexpression of CD26 in ovarian cancer leads to increased E-cadherin and tissue inhibitors of MMPs resulting in decreased invasive potential (31). CD26/DPPIV thus functions as a tumor suppressor in the cases described above and its downregulation may contribute to the loss of growth control. In contrast, CD26 expression is associated with a more aggressive clinical course in T-cell large granular lymphocyte leukemia (T-LGLL) (32).

In non-Hodgkin Lymphoma (NHL), CD26 expression is found mainly in aggressive subtypes such as T-lymphoblastic lymphoma (LBL)/T-acute lymphoblastic leukemia (ALL) and T-cell CD30+ anaplastic large cell lymphoma (ALCL). An earlier report indicated that CD26 and CD40L expression is mutually exclusive, with CD40L expressed on cells from more indolent diseases. Of note is that CD26 expression on T-cell LBL/ALL is associated with a worse survival (33). In renal cell carcinoma, CD26 is highly expressed on the cell surface of RCC tissues and many cell lines derived from RCC such as Caki-2, VMRC-RCW, and Caki-1. Moreover, anti-CD26 mAb-mediated growth inhibition of the Caki-2 cell line is associated with G1/S cell cycle arrest, enhanced $p27^{kip1}$ expression, and down regulation of CDK2 (18). We now show that CD26 is highly expressed in MM tissues, and ani-CD26 mAb treatment and CD26 downregulaton by RNAi in CD26 positive MM cell lines lead to contact inhibition and $p27^{kip1}$ upregulation.

Therefore in case of malignant tumors such as T-cell lymphoma, renal cell carcinoma, and malignant mesothelioma, CD26 plays a role in tumor growth and may be involved in invasion and metastasis. In view of its complex historical effect, the role of CD26 in cancers needs to be evaluated individually for each tumor type.

Malignant mesothelioma is an aggressive neoplasm with a dismal prognosis and is relatively unpresponsive to chemotherapy. One study systematically reviewed evidence for chemotherapy effect from 1965 through June 2001, and found 83 studies with 88 treatment arms (34). Cisplatin was the most active single drug, and cisplatin with doxorubicin had the highest response rate (28.5% response rate, confidence interval 21.3-35.7%). Since this report, results of a phaseIII randomized trial (using 448 chemotherapy naive patients with unresectable mesothelioma) involving the combination cisplatis/pemetrexed (an antimetabolite) or cisplatin alone have demonstrated that medium survival is extended from 9.3 months in those treated with cisplatin to 12.1 months in those treated with both agents (35). However standard treatments for MM are still not satisfactory in term of survival, hence there is an urgent need for novel therapeutic approaches for MM.

Our data therefore indicate that the novel humanized anti-CD26 mAb humAb is an effective therapeutic tool for cancer treatment including MM, as it can utilize the human effector system to target cancer cells in addition to its direct anti-tumor effect.

REFERENCES

1. Britton M. The epidemiology of mesothelioma. Semin Surg Oncol 2002; 29:18-25.
2. Connelly R R, Spirtas R, Myers M H, Percy C L, Fraumeni J F Jr. Demographic patterns for mesothelioma in the United States. J. Natl Cancer Inst. 1987; 78:1053-60.
3. Ismaril-Khan R, Robinson L A, Williams Jr C C, Garrett C R, Bepler G, Simon G R. Malignant Pleural Mesothelioma, a comprehensive review. Cancer control 2006; 13:255-263.
4. Pass H. Malignant pleural mesothelioma, surgical roles and novel therapies. Clin Lung Cancer 2001; 3:102-117.
5. Morimoto C, Schlossman S F. The structure and function of CD26 in the T-cell immune response. Immunol Rev 1998; 161:55-70.
6. Ishii T, Ohnuma K, Murakami A, et al. CD26-mediated signaling for T cell activation occurs in lipid rafts through its association with CD45RO. Proc Natl Acad Sci USA 2001; 98:12138-43.
7. Ohnuma K, Yamochi T, Uchiyama M, et al. CD26 up-regulates expression of CD86 on antigen-presenting cells by means of caveolin-1. Proc Natl Acad Sci USA 2004; 101:14186-91.
8. Yamochi T, Yamochi T, Aytac U, et al. Regulation of p38 phosphorylation and topoisomerase II alpha expression in the B-cell lymphoma line Jiyoye by CD26/dipeptidyl peptidase IV is associated with enhanced in vitro and in vivo sensitivity to doxorubicin. Cancer Res 2005; 65:1973-83.
9. Pro B, Dang N H. CD26/dipeptidyl peptidase IV and its role in cancer. Histol Histopathol 2004; 19:1345-51.
10. Iwata S, Morimoto C. CD26/dipeptidyl peptidase IV in context. The different roles of a multifunctional ectoenzyme in malignant transformation. J Exp Med 1999; 190: 301-6.
11. Kehlen A, Lendeckel U, Dralle H, Langner J, Hoang-Vu C. Biological significance of aminopeptidase N/CD13 in thyroid carcinomas. Cancer Res 2003; 63:8500-6.
12. Kajiyama H, Kikkawa F, Suzuki T, Shibata K, Ino K, Mizutani S. Prolonged survival and decreased invasive activity attributable to dipeptidyl peptidase IV overexpression in ovarian carcinoma. Cancer Res 2002; 62:2753-7.
13. Cheng H C, Abdel-Ghany M, Pauli B U. A novel consensus motif in fibronectin mediates dipeptidyl peptidase IV adhesion and metastasis. J Biol Chem 2003; 278:24600-7.
14. Johnson R C, Zhu D, Augustin-Voss H G, Pauli B U. Lung endothelial dipeptidyl peptidase IV is an adhesion molecule for lung-metastatic rat breast and prostate carcinoma cells. J Cell Biol 1993; 121:1423-32.
15. Dang N H, Torimoto Y, Schlossman S F, Morimoto C. Human CD4 helper T cell activation:functional involvement of two distinct collagen receptors. J. Exp Med 1990; 172:649-52
16. Ohnuma K, Ishii T, Iwata S, et al. G1/S cell cycle arrest provoked in human T cells by antibody to CD26. Immunology 2002; 107:325-33.
17. Ho L, Aytac U, Stephens L C, et al. In vitro and in vivo antitumor effect of the anti-CD26 monoclonal antibody 1F7 on human CD30+ anaplastic large cell T-cell lymphoma Karpas 299. Clinical Cancer Research 2001; 7:2031-40.
18. Inamoto T, Yamochi T, Ohnuma K, et al. Anti-CD26 monoclonal antibody-mediated G1-S arrest of human renal clear cell carcinoma Caki-2 is associated with retinoblastoma substrate dephosphorylation, cyclin-dependent kinase 2 reduction, p27(kip1) enhancement, and disruption of binding to the extracellular matrix. Clin Canc Res 2006; 12:3470-7.

19. Usami N, Fukui T, Kondo M, et al. Establishment and characterization of four malignant pleural mesothelioma cell lines from Japanese patients. Cancer Sci 2006; 97:387-94.

20. Morimoto C, Torimoto Y, Levinson G, et al. 1F7, a novel cell surface molecule, involved in helper function of CD4 cells. J Immunol 1989; 143:3430-9.

21. Kobayashi S, Ohnuma K, Uchiyama M, et al. Association of CD26 with CD45RA outside lipid rafts attenuates cord blood T-cell activation. Blood 2004; 103:1002-10.

22. Tanaka J, Miwa Y, Miyoshi K, Ueno A, Inoue H. Construction of Epstein-Barr virus-based expression vector containing mini-oriP. Biochem Biophys Res Commun 1999; 264:938-43.

23. Sato K, Aytac U, Yamochi T, et al. CD26/dipeptidyl peptidase IV enhances expression of topoisomerase II alpha and sensitivity to apoptosis induced by topoisomerase II inhibitors. Br J Cancer 2003; 89:1366-74.

24. Prang N, Preithner S, Brischwein K, et al. Cellular and complement-dependent cytotoxicity of Ep-CAM-specific monoclonal antibody MT201 against breast cancer cell lines. Br J Cancer 2005; 92:342-9.

25. Dang N H, Torimoto Y, Schlossman S F, Morimoto C. Human CD4 helper T cell activation: functional involvement of two distinct collagen receptors, 1F7 and VLA integrin family. J Exp Med 1990; 172:649-52.

26. Suzuki E, Nagata D, Yoshizumi M, et al. Reentry into the cell cycle of contact-inhibited vascular endothelial cells by a phosphatase inhibitor. Possible involvement of extracellular signal-regulated kinase and phosphatidylinositol 3-kinase. J Biol Chem 2000; 275:3637-44.

27. Levenberg S, Yarden A, Kam Z, Geiger B. p27 is involved in N-cadherin-mediated contact inhibition of cell growth and S-phase entry. Oncogene 1999; 18:869-76.

28. Shultz L D, Schweitzer P A, Christianson S W, et al. Multiple defects in innate and adaptive immunologic function in NOD/LtSz-scid mice. J Immunol 1995; 154:180-91.

29. Wesley U V, Tiwari S, Hoghton A N. Role for dipeptidyl peptidase IV in tumor suppression of human non small cell lung carcinoma cells (NSCLC). Int J Cancer 2004; 109: 855-66.

30. Wesley U V, McGroarty M, Homoyouni A. Dipeptidyl peptidase inhibits malignant phenotype of prostate cancer cells by blocking basic fibroblast growth factor signaling pathway Cancer Res. 2005; 65:1325-1334.

31. Kajiyama H, Kikkawa F, Khin E, Shibata K, Ino K, Mizutani S. Dipeptidyl peptidase IV overexpression induces up-regulation of E-cadherin and tissue inhibitors of matrix metalloproteinases, resulting in decreased invasive potential in ovarian carcinoma cells. Cancer Res. 2003; 63:2278-83.

32. Dang N H, Aytac U, Sato K, O'Brien S, Melenhorst J, Morimoto C, Barrett A J, Molldrem J J. T-large granular lymphocyte lymphoproliferative disorder:expression of CD26 as a marker of clinically aggressive disease and characterization of marrow inhibition. Br J. Haematol. 2003; 121:857-65.

33. Canbon A, Gloghini A, Zagonel V, Aldinucci D, Gattei V, Degan M, Improta S, Sorio R, Monfardini S, Pinto A, The expression of CD26 and CD40 ligand is mutually exclusive in human T-cell non-Hodgkin's lymphomas/leukemias Blood. 1995; 86:4617-4626.

34. Berghmans T, Paesmans M, Lalami Y, Lovviauxl, Luce S, Mascavx C, Meert A P, Sculier J P. Activity of chemotherapy and immunotherapy on malignant mesothelioma: a systemic review of the literature with meta-analysis. Lung Cancer 2002; 38:111-121.

35. Vogelzang N J, Rusthoven J J, Symanowski J, Denham C, Kaukel E, Ruffle P et al. PhaseIII study of pemetrexed in combination with cisplatin versus cisplatin alone in patients with malignant pleural mesothelioma. J. Clin Oncol 2003; 21:2629-2630.

The invention claimed is:

1. A method for the treatment of malignant mesothelioma, comprising a step of administering an effective amount of an anti-CD26 humanized antibody comprising a variable region of 14D10 to a subject in need thereof.

2. The method according to claim 1, wherein the humanized antibody is produced by a strain designated s604069YST-pABMC148 (x411) with American Type Culture Collection accession number PTA-7695.

3. The method according to claim 1, wherein an effective amount of an effector cell specific to the antibody is administered to the subject together with the antibody.

4. The method according to claim 1, wherein the antibody is administered in an amount ranging from 1 μg/kg to 100 mg/kg of body weight of the subject per day.

5. The method according to claim 1, wherein the antibody is administered in an amount of at least 1 μg/kg of body weight of the subject per day.

6. A method for inhibiting growth of a malignant mesothelioma cell, which comprises contacting a malignant mesothelioma cell with an anti-CD26 humanized antibody comprising a variable region of 14D10.

7. The method according to claim 6, wherein the humanized antibody is produced by a strain designated s604069YST-pABMC148 (x411) with American Type Culture Collection accession number PTA-7695.

8. A method for inhibiting growth of a malignant mesothelioma cell, which comprises contacting the malignant mesothelioma cell and an effector cell with an anti-CD26 humanized antibody comprising a variable region of 14D10, wherein the effector cell is a cell specific to the antibody.

9. The method according to claim 8, wherein the humanized antibody is produced by a strain designated s604069YST-pABMC148 (x411) with American Type Culture Collection accession number PTA-7695.

10. A method for lysing a malignant mesothelioma cell, which comprises contacting the malignant mesothelioma cell and an effector cell with an anti-CD26 humanized antibody comprising a variable region of 14D10, wherein lysis of the cell is caused by antibody-dependent cell-mediated cytotoxicity and wherein the effector cell is a cell specific to the antibody.

11. The method according to claim 10, wherein the humanized antibody is produced by a strain designated s604069YST-pABMC148 (x411) with American Type Culture Collection accession number PTA-7695.

12. A method for lysing a malignant mesothelioma cell, which comprises contacting the malignant mesothelioma cell and an effector cell with an anti-CD26 humanized antibody comprising a variable region of 14D10, wherein the effector cell is a cell specific to the antibody.

* * * * *

SEQUENCE LISTING

```
<160> NUMBER OF SEQ ID NOS: 33

<210> SEQ ID NO 1
<211> LENGTH: 107
<212> TYPE: PRT
<213> ORGANISM: Artificial
<220> FEATURE:
<223> OTHER INFORMATION: Synthetic Peptide

<400> SEQUENCE: 1

Asp Ile Leu Met Thr Gln Ser Pro Ser Ser Leu Ser Ala Ser Pro Gly
1               5                   10                  15

Asp Arg Val Thr Ile Ser Cys Arg Ala Ser Gln Asp Ile Arg Asn Asn
            20                  25                  30

Leu Asn Trp Tyr Gln Gln Lys Pro Gly Gln Ala Pro Arg Leu Leu Ile
        35                  40                  45

Tyr Tyr Ser Ser Asn Leu His Ser Gly Val Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Ala Tyr Tyr Cys Gln Gln Ser Ile Lys Leu Pro Leu
                85                  90                  95

Thr Phe Gly Ser Gly Thr Lys Val Glu Ile Lys
            100                 105
```

```
<210> SEQ ID NO 2
<211> LENGTH: 107
<212> TYPE: PRT
<213> ORGANISM: Artificial
<220> FEATURE:
<223> OTHER INFORMATION: Synthetic Peptide

<400> SEQUENCE: 2

Glu Ile Glu Leu Thr Gln Ser Pro Ser Ser Leu Ser Val Ser Leu Gly
1               5                   10                  15

Asp Arg Val Thr Ile Ser Cys Ser Ala Ser Gln Asp Ile Arg Asn Asn
            20                  25                  30

Leu Asn Trp Tyr Gln Gln Lys Pro Gly Gln Ala Pro Arg Leu Leu Ile
        35                  40                  45

Tyr Tyr Ser Ser Asn Leu Gln Thr Gly Val Pro Ala Arg Phe Ser Gly
    50                  55                  60

Ser Gly Ser Gly Thr Asp Phe Thr Leu Thr Ile Ser Arg Leu Glu Pro
65                  70                  75                  80

Glu Asp Val Ala Ala Tyr Tyr Cys Gln Gln Ser Ile Lys Leu Pro Phe
                85                  90                  95

Thr Phe Gly Ser Gly Thr Lys Val Glu Ile Lys
            100                 105


<210> SEQ ID NO 3
<211> LENGTH: 107
<212> TYPE: PRT
<213> ORGANISM: Artificial
<220> FEATURE:
<223> OTHER INFORMATION: Synthetic Peptide

<400> SEQUENCE: 3

Asp Ile Glu Met Thr Gln Ser Pro Ser Ser Leu Ser Ala Ser Ala Gly
1               5                   10                  15

Glu Arg Val Thr Ile Ser Cys Arg Ala Ser Gln Gly Ile Arg Asn Ser
            20                  25                  30

Leu Asn Trp Tyr Gln Gln Lys Pro Gly Gln Ala Pro Arg Leu Leu Ile
        35                  40                  45

Tyr Tyr Ser Ser Asn Leu Gln Thr Gly Val Pro Ser Arg Phe Ser Gly
    50                  55                  60

Ser Gly Ser Gly Thr Asp Phe Thr Leu Thr Ile Ser Arg Leu Gln Ala
65                  70                  75                  80

Glu Asp Phe Ala Thr Tyr Tyr Cys Gln Gln Ser Asn Lys Leu Pro Phe
                85                  90                  95

Thr Phe Gly Ser Gly Thr Lys Val Glu Ile Lys
            100                 105


<210> SEQ ID NO 4
<211> LENGTH: 107
<212> TYPE: PRT
<213> ORGANISM: Artificial
<220> FEATURE:
<223> OTHER INFORMATION: Synthetic Peptide

<400> SEQUENCE: 4

Asp Ile Leu Leu Thr Gln Ser Pro Ser Ser Leu Ser Ala Thr Pro Gly
1               5                   10                  15

Glu Arg Ala Thr Ile Thr Cys Arg Ala Ser Gln Gly Ile Arg Asn Asn
            20                  25                  30
```

```
Leu Asn Trp Tyr Gln Gln Lys Pro Gly Gln Ala Pro Arg Leu Leu Ile
        35                  40                  45

Tyr Tyr Ser Ser Asn Leu Gln Ser Gly Val Pro Ser Arg Phe Ser Gly
    50                  55                  60

Ser Gly Ser Gly Thr Asp Phe Thr Leu Thr Ile Ser Arg Leu Gln Pro
65                  70                  75                  80

Glu Asp Val Ala Ala Tyr Tyr Cys Gln Gln Ser Ile Lys Leu Pro Phe
                85                  90                  95

Thr Phe Gly Ser Gly Thr Lys Val Glu Ile Lys
            100                 105


<210> SEQ ID NO 5
<211> LENGTH: 107
<212> TYPE: PRT
<213> ORGANISM: Artificial
<220> FEATURE:
<223> OTHER INFORMATION: Synthetic Peptide

<400> SEQUENCE: 5

Glu Ile Glu Met Thr Gln Ser Pro Ser Ser Leu Ser Val Ser Ala Gly
1               5                   10                  15

Glu Arg Ala Thr Ile Ser Cys Ser Ala Ser Gln Asp Ile Arg Asn Ser
            20                  25                  30

Leu Asn Trp Tyr Gln Gln Lys Pro Gly Gln Ala Pro Arg Leu Leu Ile
        35                  40                  45

Tyr Tyr Ser Ser Asn Leu His Thr Gly Val Pro Ala Arg Phe Ser Gly
    50                  55                  60

Ser Gly Ser Gly Thr Asp Phe Thr Leu Thr Ile Ser Arg Leu Glu Pro
65                  70                  75                  80

Glu Asp Val Ala Ile Tyr Tyr Cys Gln Gln Ser Asn Lys Leu Pro Leu
                85                  90                  95

Thr Phe Gly Ser Gly Thr Lys Val Glu Ile Lys
            100                 105


<210> SEQ ID NO 6
<211> LENGTH: 107
<212> TYPE: PRT
<213> ORGANISM: Artificial
<220> FEATURE:
<223> OTHER INFORMATION: Synthetic Peptide

<400> SEQUENCE: 6

Glu Ile Glu Leu Thr Gln Ser Pro Ser Ser Leu Ser Val Ser Pro Gly
1               5                   10                  15

Asp Arg Val Thr Ile Ser Cys Ser Ala Ser Gln Gly Ile Arg Asn Ser
            20                  25                  30

Leu Asn Trp Tyr Gln Gln Lys Pro Gly Gln Ala Pro Arg Leu Leu Ile
        35                  40                  45

Tyr Tyr Ser Ser Asn Leu His Thr Gly Val Pro Ala Arg Phe Ser Gly
    50                  55                  60

Ser Gly Ser Gly Thr Asp Phe Thr Leu Thr Ile Ser Arg Leu Gln Ala
65                  70                  75                  80

Glu Asp Phe Ala Thr Tyr Tyr Cys Gln Gln Ser Ile Lys Leu Pro Leu
                85                  90                  95

Thr Phe Gly Ser Gly Thr Lys Val Glu Ile Lys
            100                 105


<210> SEQ ID NO 7
```

```
<211> LENGTH: 107
<212> TYPE: PRT
<213> ORGANISM: Artificial
<220> FEATURE:
<223> OTHER INFORMATION: Synthetic Peptide

<400> SEQUENCE: 7

Asp Ile Leu Met Thr Gln Ser Pro Ser Ser Leu Ser Ala Ser Pro Gly
1               5                   10                  15

Asp Arg Val Thr Ile Ser Cys Arg Ala Ser Gln Asp Ile Arg Asn Asn
            20                  25                  30

Leu Asn Trp Tyr Gln Gln Lys Pro Gly Gln Ala Pro Arg Leu Leu Ile
        35                  40                  45

Tyr Tyr Ser Ser Asn Leu Gln Thr Gly Val Pro Ala Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Ala Tyr Tyr Cys Gln Gln Ser Ile Lys Leu Pro Leu
                85                  90                  95

Thr Phe Gly Ser Gly Thr Lys Val Glu Ile Lys
            100                 105


<210> SEQ ID NO 8
<211> LENGTH: 116
<212> TYPE: PRT
<213> ORGANISM: Artificial
<220> FEATURE:
<223> OTHER INFORMATION: Synthetic Peptide

<400> SEQUENCE: 8

Glu Val Gln Leu Val Glu Ser Gly Ala Gly Val Lys Gln Pro Gly Gly
1               5                   10                  15

Thr Leu Arg Leu Thr Cys Thr Ala Ser Gly Phe Ser Leu Thr Thr Tyr
            20                  25                  30

Gly Val His Trp Val Arg Gln Ala Pro Gly Lys Gly Leu Glu Trp Val
        35                  40                  45

Gly Val Ile Trp Gly Asp Gly Arg Thr Asp Tyr Asp Ala Ala Phe Met
    50                  55                  60

Ser Arg Val Thr Ile Ser Lys Asp Thr Ser Lys Ser Thr Val Tyr Leu
65                  70                  75                  80

Gln Met Asn Ser Leu Arg Ala Glu Asp Thr Ala Val Tyr Tyr Cys Met
                85                  90                  95

Arg Asn Arg His Asp Trp Phe Asp Tyr Trp Gly Gln Gly Thr Thr Val
            100                 105                 110

Thr Val Ser Ser
        115


<210> SEQ ID NO 9
<211> LENGTH: 116
<212> TYPE: PRT
<213> ORGANISM: Artificial
<220> FEATURE:
<223> OTHER INFORMATION: Synthetic Peptide

<400> SEQUENCE: 9

Glu Val Gln Leu Val Gln Ser Gly Gly Gly Val Lys Gln Pro Gly Glu
1               5                   10                  15

Thr Leu Arg Leu Thr Cys Thr Ala Ser Gly Phe Ser Leu Thr Thr Tyr
            20                  25                  30
```

-continued

```
Gly Val His Trp Val Arg Gln Ala Pro Gly Lys Gly Leu Glu Trp Val
        35                  40                  45

Gly Val Ile Trp Gly Asp Gly Arg Thr Asp Tyr Asp Ala Ala Phe Met
    50                  55                  60

Ser Arg Val Thr Ile Ser Lys Asp Thr Ser Lys Ser Thr Ala Tyr Leu
65                  70                  75                  80

Gln Met Asn Ser Leu Arg Ala Glu Asp Thr Ala Val Tyr Tyr Cys Met
                85                  90                  95

Arg Asn Arg His Asp Trp Phe Asp Tyr Trp Gly Gln Gly Thr Thr Val
            100                 105                 110

Thr Val Ser Ser
        115
```

<210> SEQ ID NO 10
<211> LENGTH: 116
<212> TYPE: PRT
<213> ORGANISM: Artificial
<220> FEATURE:
<223> OTHER INFORMATION: Synthetic Peptide

<400> SEQUENCE: 10

```
Glu Val Gln Leu Val Glu Ser Gly Ala Gly Val Glu Gln Pro Gly Gly
1               5                   10                  15

Thr Leu Arg Leu Thr Cys Thr Ala Ser Gly Phe Ser Leu Thr Thr Tyr
            20                  25                  30

Gly Val His Trp Val Arg Gln Ala Pro Gly Lys Gly Leu Glu Trp Met
        35                  40                  45

Gly Val Ile Trp Gly Asp Gly Arg Thr Asp Tyr Asp Ala Ala Phe Met
    50                  55                  60

Ser Arg Val Thr Ile Ser Arg Asp Thr Ser Lys Ser Thr Ala Tyr Leu
65                  70                  75                  80

Gln Leu Asn Ser Leu Arg Ala Glu Asp Thr Ala Val Tyr Tyr Cys Val
                85                  90                  95

Arg Asn Arg His Asp Trp Phe Asp Tyr Trp Gly Gln Gly Thr Thr Val
            100                 105                 110

Thr Val Ser Ser
        115
```

<210> SEQ ID NO 11
<211> LENGTH: 116
<212> TYPE: PRT
<213> ORGANISM: Artificial
<220> FEATURE:
<223> OTHER INFORMATION: Synthetic Peptide

<400> SEQUENCE: 11

```
Glu Val Gln Leu Val Glu Ser Gly Ala Glu Leu Val Gln Pro Gly Gly
1               5                   10                  15

Ser Leu Arg Leu Thr Cys Lys Ala Ser Gly Phe Thr Leu Asn Thr Tyr
            20                  25                  30

Gly Val His Trp Val Arg Gln Ala Pro Gly Lys Gly Leu Glu Trp Met
        35                  40                  45

Gly Val Ile Trp Gly Gly Gly Arg Thr Asp Tyr Asp Ala Ser Phe Met
    50                  55                  60

Ser Arg Val Thr Ile Ser Lys Asp Asn Ser Lys Asn Thr Ala Tyr Leu
65                  70                  75                  80

Gln Leu Asn Ser Leu Arg Ala Glu Asp Thr Ala Val Tyr Tyr Cys Thr
                85                  90                  95
```

```
Arg Ser Arg His Asp Trp Phe Asp Tyr Trp Gly Gln Gly Thr Thr Val
            100                 105                 110

Thr Val Ser Ser
        115


<210> SEQ ID NO 12
<211> LENGTH: 116
<212> TYPE: PRT
<213> ORGANISM: Artificial
<220> FEATURE:
<223> OTHER INFORMATION: Synthetic Peptide

<400> SEQUENCE: 12

Glu Val Gln Leu Val Gln Ser Gly Gly Gly Leu Lys Gln Pro Gly Glu
1               5                   10                  15

Thr Leu Arg Leu Ser Cys Thr Ala Ser Gly Tyr Ser Leu Thr Thr Tyr
            20                  25                  30

Gly Val His Trp Val Arg Gln Ala Pro Gly Lys Gly Leu Glu Trp Met
        35                  40                  45

Gly Val Ile Trp Gly Asp Gly Arg Thr Asp Tyr Asp Ser Ser Phe Met
    50                  55                  60

Ser Arg Val Thr Ile Ser Lys Asp Thr Ser Lys Ser Thr Ala Tyr Leu
65                  70                  75                  80

Gln Leu Asn Ser Leu Arg Ala Glu Asp Thr Ala Val Tyr Tyr Cys Thr
                85                  90                  95

Arg Asn Arg His Asp Trp Phe Asp Tyr Trp Gly Gln Gly Thr Thr Val
            100                 105                 110

Thr Val Ser Ser
        115


<210> SEQ ID NO 13
<211> LENGTH: 116
<212> TYPE: PRT
<213> ORGANISM: Artificial
<220> FEATURE:
<223> OTHER INFORMATION: Synthetic Peptide

<400> SEQUENCE: 13

Glu Val Gln Leu Val Gln Ser Gly Gly Gly Val Lys Gln Pro Gly Glu
1               5                   10                  15

Thr Leu Arg Leu Thr Cys Thr Ala Ser Gly Phe Ser Leu Ser Thr Tyr
            20                  25                  30

Gly Val His Trp Val Arg Gln Ala Pro Gly Lys Gly Leu Glu Trp Val
        35                  40                  45

Gly Val Ile Trp Gly Asp Gly Arg Thr Asp Tyr Asp Ala Ala Phe Met
    50                  55                  60

Ser Arg Val Thr Ile Ser Lys Asp Thr Ser Lys Ser Thr Val Tyr Leu
65                  70                  75                  80

Gln Met Asn Ser Leu Arg Ala Glu Asp Thr Ala Val Tyr Tyr Cys Met
                85                  90                  95

Arg Asn Arg His Asp Trp Phe Asp Tyr Trp Gly Gln Gly Thr Thr Val
            100                 105                 110

Thr Val Ser Ser
        115


<210> SEQ ID NO 14
<211> LENGTH: 116
<212> TYPE: PRT
```

-continued

<213> ORGANISM: Artificial
<220> FEATURE:
<223> OTHER INFORMATION: Synthetic Peptide

<400> SEQUENCE: 14

```
Glu Val Gln Leu Val Glu Ser Gly Gly Gly Val Lys Gln Pro Gly Glu
1               5                   10                  15

Thr Leu Arg Leu Thr Cys Thr Ala Ser Gly Phe Ser Leu Ser Thr Tyr
            20                  25                  30

Gly Val His Trp Val Arg Gln Ala Pro Gly Lys Gly Leu Glu Trp Val
        35                  40                  45

Gly Val Ile Trp Gly Asp Gly Arg Thr Asp Tyr Asp Ala Ala Phe Met
    50                  55                  60

Ser Arg Val Thr Ile Ser Lys Asp Thr Ser Lys Ser Thr Val Tyr Leu
65                  70                  75                  80

Gln Met Asn Ser Leu Arg Ala Glu Asp Thr Ala Val Tyr Tyr Cys Met
                85                  90                  95

Arg Asn Arg His Asp Trp Phe Asp Tyr Trp Gly Gln Gly Thr Thr Val
            100                 105                 110

Thr Val Ser Ser
        115
```

<210> SEQ ID NO 15
<211> LENGTH: 116
<212> TYPE: PRT
<213> ORGANISM: Artificial
<220> FEATURE:
<223> OTHER INFORMATION: Synthetic Peptide
<220> FEATURE:
<221> NAME/KEY: misc_feature
<222> LOCATION: (6)..(6)
<223> OTHER INFORMATION: Xaa is Glu or Gln
<220> FEATURE:
<221> NAME/KEY: misc_feature
<222> LOCATION: (9)..(9)
<223> OTHER INFORMATION: Xaa is Ala or Gly
<220> FEATURE:
<221> NAME/KEY: misc_feature
<222> LOCATION: (10)..(10)
<223> OTHER INFORMATION: Xaa is Gly or Glu
<220> FEATURE:
<221> NAME/KEY: misc_feature
<222> LOCATION: (11)..(11)
<223> OTHER INFORMATION: Xaa is Leu or Val
<220> FEATURE:
<221> NAME/KEY: misc_feature
<222> LOCATION: (12)..(12)
<223> OTHER INFORMATION: Xaa is Val, Lys or Glu
<220> FEATURE:
<221> NAME/KEY: misc_feature
<222> LOCATION: (16)..(16)
<223> OTHER INFORMATION: Xaa is Gly or Glu
<220> FEATURE:
<221> NAME/KEY: misc_feature
<222> LOCATION: (17)..(17)
<223> OTHER INFORMATION: Xaa is Thr or Ser
<220> FEATURE:
<221> NAME/KEY: misc_feature
<222> LOCATION: (21)..(21)
<223> OTHER INFORMATION: Xaa is Thr or Ser
<220> FEATURE:
<221> NAME/KEY: misc_feature
<222> LOCATION: (23)..(23)
<223> OTHER INFORMATION: Xaa is Thr or Lys
<220> FEATURE:
<221> NAME/KEY: misc_feature
<222> LOCATION: (27)..(27)
<223> OTHER INFORMATION: Xaa is Phe or Tyr
<220> FEATURE:
<221> NAME/KEY: misc_feature -continued
<222> LOCATION: (28)..(28)
<223> OTHER INFORMATION: Xaa is Ser or Thr
<220> FEATURE:
<221> NAME/KEY: misc_feature
<222> LOCATION: (30)..(30)
<223> OTHER INFORMATION: Xaa is Thr, Asn or Ser
<220> FEATURE:
<221> NAME/KEY: misc_feature
<222> LOCATION: (48)..(48)
<223> OTHER INFORMATION: Xaa is Val or Met
<220> FEATURE:
<221> NAME/KEY: misc_feature
<222> LOCATION: (54)..(54)
<223> OTHER INFORMATION: Xaa is Gly or Asp
<220> FEATURE:
<221> NAME/KEY: misc_feature
<222> LOCATION: (61)..(61)
<223> OTHER INFORMATION: Xaa is Ala or Ser
<220> FEATURE:
<221> NAME/KEY: misc_feature
<222> LOCATION: (62)..(62)
<223> OTHER INFORMATION: Xaa is Ala or Ser
<220> FEATURE:
<221> NAME/KEY: misc_feature
<222> LOCATION: (71)..(71)
<223> OTHER INFORMATION: Xaa is Lys or Arg
<220> FEATURE:
<221> NAME/KEY: misc_feature
<222> LOCATION: (73)..(73)
<223> OTHER INFORMATION: Xaa is Asn or Thr
<220> FEATURE:
<221> NAME/KEY: misc_feature
<222> LOCATION: (76)..(76)
<223> OTHER INFORMATION: Xaa is Ser or Asn
<220> FEATURE:
<221> NAME/KEY: misc_feature
<222> LOCATION: (78)..(78)
<223> OTHER INFORMATION: Xaa is Val or Ala
<220> FEATURE:
<221> NAME/KEY: misc_feature
<222> LOCATION: (82)..(82)
<223> OTHER INFORMATION: Xaa is Met or Leu
<220> FEATURE:
<221> NAME/KEY: misc_feature
<222> LOCATION: (96)..(96)
<223> OTHER INFORMATION: Xaa is Val, Met or Thr
<220> FEATURE:
<221> NAME/KEY: misc_feature
<222> LOCATION: (98)..(98)
<223> OTHER INFORMATION: Xaa is Asn or Ser

<400> SEQUENCE: 15

```
Glu Val Gln Leu Val Xaa Ser Gly Xaa Xaa Xaa Xaa Gln Pro Gly Xaa
1               5                   10                  15

Xaa Leu Arg Leu Xaa Cys Xaa Ala Ser Gly Xaa Xaa Leu Xaa Thr Tyr
            20                  25                  30

Gly Val His Trp Val Arg Gln Ala Pro Gly Lys Gly Leu Glu Trp Xaa
        35                  40                  45

Gly Val Ile Trp Gly Xaa Gly Arg Thr Asp Tyr Asp Xaa Xaa Phe Met
    50                  55                  60

Ser Arg Val Thr Ile Ser Xaa Asp Xaa Ser Lys Xaa Thr Xaa Tyr Leu
65                  70                  75                  80

Gln Xaa Asn Ser Leu Arg Ala Glu Asp Thr Ala Val Tyr Tyr Cys Xaa
                85                  90                  95

Arg Xaa Arg His Asp Trp Phe Asp Tyr Trp Gly Gln Gly Thr Thr Val
            100                 105                 110

Thr Val Ser Ser
        115
```

<210> SEQ ID NO 16

<211> LENGTH: 107
<212> TYPE: PRT
<213> ORGANISM: Artificial
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Xaa is Asp or Glu
<220> FEATURE:
<221> NAME/KEY: misc_feature
<222> LOCATION: (3)..(3)
<223> OTHER INFORMATION: Xaa is Leu or Glu
<220> FEATURE:
<221> NAME/KEY: misc_feature
<222> LOCATION: (4)..(4)
<223> OTHER INFORMATION: Xaa is Met or Leu
<220> FEATURE:
<221> NAME/KEY: misc_feature
<222> LOCATION: (13)..(13)
<223> OTHER INFORMATION: Xaa is Ala or Val
<220> FEATURE:
<221> NAME/KEY: misc_feature
<222> LOCATION: (14)..(14)
<223> OTHER INFORMATION: Xaa is Ser or Thr
<220> FEATURE:
<221> NAME/KEY: misc_feature
<222> LOCATION: (15)..(15)
<223> OTHER INFORMATION: Xaa is Leu, Pro or Ala
<220> FEATURE:
<221> NAME/KEY: misc_feature
<222> LOCATION: (17)..(17)
<223> OTHER INFORMATION: Xaa is Asp or Glu
<220> FEATURE:
<221> NAME/KEY: misc_feature
<222> LOCATION: (19)..(19)
<223> OTHER INFORMATION: Xaa is Val or Ala
<220> FEATURE:
<221> NAME/KEY: misc_feature
<222> LOCATION: (22)..(22)
<223> OTHER INFORMATION: Xaa is Thr or Ser
<220> FEATURE:
<221> NAME/KEY: misc_feature
<222> LOCATION: (24)..(24)
<223> OTHER INFORMATION: Xaa is Ser or Arg
<220> FEATURE:
<221> NAME/KEY: misc_feature
<222> LOCATION: (28)..(28)
<223> OTHER INFORMATION: Xaa is Gly or Asp
<220> FEATURE:
<221> NAME/KEY: misc_feature
<222> LOCATION: (32)..(32)
<223> OTHER INFORMATION: Xaa is Ser or Asn
<220> FEATURE:
<221> NAME/KEY: misc_feature
<222> LOCATION: (55)..(55)
<223> OTHER INFORMATION: Xaa is His or Gln
<220> FEATURE:
<221> NAME/KEY: misc_feature
<222> LOCATION: (56)..(56)
<223> OTHER INFORMATION: Xaa is Ser or Thr
<220> FEATURE:
<221> NAME/KEY: misc_feature
<222> LOCATION: (60)..(60)
<223> OTHER INFORMATION: Xaa is Ser, Asp or Ala
<220> FEATURE:
<221> NAME/KEY: misc_feature
<222> LOCATION: (79)..(79)
<223> OTHER INFORMATION: Xaa is Glu or Gln
<220> FEATURE:
<221> NAME/KEY: misc_feature
<222> LOCATION: (80)..(80)
<223> OTHER INFORMATION: Xaa is Pro or Ala
<220> FEATURE:
<221> NAME/KEY: misc_feature
<222> LOCATION: (83)..(83)
<223> OTHER INFORMATION: Xaa is Phe or Val
<220> FEATURE:
<221> NAME/KEY: misc_feature
<222> LOCATION: (85)..(85)
<223> OTHER INFORMATION: Xaa is Thr, Ala or Ile
<220> FEATURE:
<221> NAME/KEY: misc_feature
<222> LOCATION: (92)..(92)
<223> OTHER INFORMATION: Xaa is Ile or Asn
<220> FEATURE:
<221> NAME/KEY: misc_feature
<222> LOCATION: (96)..(96)
<223> OTHER INFORMATION: Xaa is Phe or Leu

<400> SEQUENCE: 16

```
Xaa Ile Xaa Xaa Thr Gln Ser Pro Ser Ser Leu Ser Xaa Xaa Xaa Gly
1               5                   10                  15

Xaa Arg Xaa Thr Ile Xaa Cys Xaa Ala Ser Gln Xaa Ile Arg Asn Xaa
            20                  25                  30

Leu Asn Trp Tyr Gln Gln Lys Pro Gly Gln Ala Pro Arg Leu Leu Ile
        35                  40                  45

Tyr Tyr Ser Ser Asn Leu Xaa Xaa Gly Val Pro Xaa Arg Phe Ser Gly
    50                  55                  60

Ser Gly Ser Gly Thr Asp Phe Thr Leu Thr Ile Ser Arg Leu Xaa Xaa
65                  70                  75                  80

Glu Asp Xaa Ala Xaa Tyr Tyr Cys Gln Gln Ser Xaa Lys Leu Pro Xaa
                85                  90                  95

Thr Phe Gly Ser Gly Thr Lys Val Glu Ile Lys
            100                 105
```

<210> SEQ ID NO 17
<211> LENGTH: 465
<212> TYPE: PRT
<213> ORGANISM: Artificial
<220> FEATURE:
<223> OTHER INFORMATION: Synthetic Peptide

<400> SEQUENCE: 17

```
Met Glu Trp Ser Trp Val Phe Leu Phe Phe Leu Ser Val Thr Thr Gly
1               5                   10                  15

Val His Ser Glu Val Gln Leu Val Glu Ser Gly Ala Gly Val Lys Gln
            20                  25                  30

Pro Gly Gly Thr Leu Arg Leu Thr Cys Thr Ala Ser Gly Phe Ser Leu
        35                  40                  45

Thr Thr Tyr Gly Val His Trp Val Arg Gln Ala Pro Gly Lys Gly Leu
    50                  55                  60

Glu Trp Val Gly Val Ile Trp Gly Asp Gly Arg Thr Asp Tyr Asp Ala
65                  70                  75                  80

Ala Phe Met Ser Arg Val Thr Ile Ser Lys Asp Thr Ser Lys Ser Thr
                85                  90                  95

Val Tyr Leu Gln Met Asn Ser Leu Arg Ala Glu Asp Thr Ala Val Tyr
            100                 105                 110

Tyr Cys Met Arg Asn Arg His Asp Trp Phe Asp Tyr Trp Gly Gln Gly
        115                 120                 125

Thr Thr Val Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190
```

```
Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220

Ser Asn Thr Lys Val Asp Lys Lys Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Arg Asp Glu Leu Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
    450                 455                 460

Lys
465
```

<210> SEQ ID NO 18
<211> LENGTH: 234
<212> TYPE: PRT
<213> ORGANISM: Artificial
<220> FEATURE:
<223> OTHER INFORMATION: Synthetic Peptide

<400> SEQUENCE: 18

```
Met Ser Val Pro Thr Gln Val Leu Gly Leu Leu Leu Leu Trp Leu Thr
1               5                   10                  15

Asp Ala Arg Cys Asp Ile Leu Leu Thr Gln Ser Pro Ser Ser Leu Ser
            20                  25                  30

Ala Thr Pro Gly Glu Arg Ala Thr Ile Thr Cys Arg Ala Ser Gln Gly
        35                  40                  45

Ile Arg Asn Asn Leu Asn Trp Tyr Gln Gln Lys Pro Gly Gln Ala Pro
    50                  55                  60

Arg Leu Leu Ile Tyr Tyr Ser Ser Asn Leu Gln Ser Gly Val Pro Ser
65                  70                  75                  80
```

```
Arg Phe Ser Gly Ser Gly Ser Gly Thr Asp Phe Thr Leu Thr Ile Ser
                85                  90                  95

Arg Leu Gln Pro Glu Asp Val Ala Ala Tyr Tyr Cys Gln Gln Ser Ile
            100                 105                 110

Lys Leu Pro Phe Thr Phe Gly Ser Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230


<210> SEQ ID NO 19
<211> LENGTH: 13
<212> TYPE: PRT
<213> ORGANISM: Artificial
<220> FEATURE:
<223> OTHER INFORMATION: Synthetic Peptide

<400> SEQUENCE: 19

Tyr Ser Leu Arg Trp Ile Ser Asp His Glu Tyr Leu Tyr
1               5                   10


<210> SEQ ID NO 20
<211> LENGTH: 13
<212> TYPE: PRT
<213> ORGANISM: Artificial
<220> FEATURE:
<223> OTHER INFORMATION: Synthetic Peptide

<400> SEQUENCE: 20

Leu Glu Tyr Asn Tyr Val Lys Gln Trp Arg His Ser Tyr
1               5                   10


<210> SEQ ID NO 21
<211> LENGTH: 13
<212> TYPE: PRT
<213> ORGANISM: Artificial
<220> FEATURE:
<223> OTHER INFORMATION: Synthetic Peptide

<400> SEQUENCE: 21

Thr Trp Ser Pro Val Gly His Lys Leu Ala Tyr Val Trp
1               5                   10


<210> SEQ ID NO 22
<211> LENGTH: 13
<212> TYPE: PRT
<213> ORGANISM: Artificial
<220> FEATURE:
<223> OTHER INFORMATION: Synthetic Peptide

<400> SEQUENCE: 22
```

-continued

Leu Trp Trp Ser Pro Asn Gly Thr Phe Leu Ala Tyr Ala
1 5 10

<210> SEQ ID NO 23
<211> LENGTH: 13
<212> TYPE: PRT
<213> ORGANISM: Artificial
<220> FEATURE:
<223> OTHER INFORMATION: Synthetic Peptide

<400> SEQUENCE: 23

Arg Ile Ser Leu Gln Trp Leu Arg Arg Ile Gln Asn Tyr
1 5 10

<210> SEQ ID NO 24
<211> LENGTH: 13
<212> TYPE: PRT
<213> ORGANISM: Artificial
<220> FEATURE:
<223> OTHER INFORMATION: Synthetic Peptide

<400> SEQUENCE: 24

Tyr Val Lys Gln Trp Arg His Ser Tyr Thr Ala Ser Tyr
1 5 10

<210> SEQ ID NO 25
<211> LENGTH: 13
<212> TYPE: PRT
<213> ORGANISM: Artificial
<220> FEATURE:
<223> OTHER INFORMATION: Synthetic Peptide

<400> SEQUENCE: 25

Glu Glu Glu Val Phe Ser Ala Tyr Ser Ala Leu Trp Trp
1 5 10

<210> SEQ ID NO 26
<211> LENGTH: 13
<212> TYPE: PRT
<213> ORGANISM: Artificial
<220> FEATURE:
<223> OTHER INFORMATION: Synthetic Peptide

<400> SEQUENCE: 26

Asp Tyr Ser Ile Ser Pro Asp Gly Gln Phe Ile Leu Leu
1 5 10

<210> SEQ ID NO 27
<211> LENGTH: 13
<212> TYPE: PRT
<213> ORGANISM: Artificial
<220> FEATURE:
<223> OTHER INFORMATION: Synthetic Peptide

<400> SEQUENCE: 27

Ser Ile Ser Pro Asp Gly Gln Phe Ile Leu Leu Glu Tyr
1 5 10

<210> SEQ ID NO 28
<211> LENGTH: 13
<212> TYPE: PRT
<213> ORGANISM: Artificial
<220> FEATURE:
<223> OTHER INFORMATION: Synthetic Peptide

<400> SEQUENCE: 28

-continued

```
Ile Tyr Val Lys Ile Glu Pro Asn Leu Pro Ser Tyr Arg
1               5                   10


<210> SEQ ID NO 29
<211> LENGTH: 15
<212> TYPE: PRT
<213> ORGANISM: Artificial
<220> FEATURE:
<223> OTHER INFORMATION: Synthetic Peptide

<400> SEQUENCE: 29

Gly Gly Gly Gly Ser Gly Gly Gly Gly Ser Gly Gly Gly Gly Ser
1               5                   10                  15


<210> SEQ ID NO 30
<211> LENGTH: 21
<212> TYPE: DNA
<213> ORGANISM: Artificial
<220> FEATURE:
<223> OTHER INFORMATION: Synthetic RNA

<400> SEQUENCE: 30

gaaagguguc aguacuauut t                                               21


<210> SEQ ID NO 31
<211> LENGTH: 21
<212> TYPE: DNA
<213> ORGANISM: Artificial
<220> FEATURE:
<223> OTHER INFORMATION: Synthetic RNA

<400> SEQUENCE: 31

ttcuuuccac agucaugaua a                                               21


<210> SEQ ID NO 32
<211> LENGTH: 21
<212> TYPE: DNA
<213> ORGANISM: Artificial
<220> FEATURE:
<223> OTHER INFORMATION: Synthetic RNA

<400> SEQUENCE: 32

uaauuagggu cggguaaact t                                               21


<210> SEQ ID NO 33
<211> LENGTH: 21
<212> TYPE: DNA
<213> ORGANISM: Artificial
<220> FEATURE:
<223> OTHER INFORMATION: Synthetic RNA

<400> SEQUENCE: 33

ttauuaaucc cagcccauuu g                                               21
```